US011821900B2

(12) United States Patent
Bremer

(10) Patent No.: US 11,821,900 B2
(45) Date of Patent: *Nov. 21, 2023

(54) METHOD OF SELECTION FOR TREATMENT OF SUBJECTS AT RISK OF INVASIVE BREAST CANCER

(71) Applicant: Prelude Corporation, Laguna Hills, CA (US)

(72) Inventor: Troy M. Bremer, Irvine, CA (US)

(73) Assignee: Prelude Corporation, Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,471

(22) Filed: Feb. 24, 2022

(65) Prior Publication Data
US 2022/0260569 A1 Aug. 18, 2022

Related U.S. Application Data

(63) Continuation of application No. 17/275,406, filed as application No. PCT/US2019/051128 on Sep. 13, 2019.

(60) Provisional application No. 62/731,316, filed on Sep. 14, 2018.

(51) Int. Cl.
G01N 33/00 (2006.01)
A61K 39/00 (2006.01)
G01N 33/574 (2006.01)

(52) U.S. Cl.
CPC ... *G01N 33/57415* (2013.01); *G01N 2333/82* (2013.01); *G01N 2333/9108* (2013.01)

(58) Field of Classification Search
CPC ......... G01N 33/57415; G01N 2333/82; G01N 2333/9108; G01N 33/57484; G01N 2800/52; G01N 33/574
See application file for complete search history.

(56) References Cited

U.S. PATENT DOCUMENTS

| | | |
|---|---|---|
| 4,318,846 A | 3/1982 | Khanna et al. |
| 4,415,732 A | 11/1983 | Caruthers et al. |
| 4,458,066 A | 7/1984 | Caruthers et al. |
| 4,591,570 A | 5/1986 | Chang |
| 4,605,735 A | 8/1986 | Miyoshi et al. |
| 4,683,195 A | 7/1987 | Mullis et al. |
| 4,683,202 A | 7/1987 | Mullis |
| 4,757,141 A | 7/1988 | Fung et al. |
| 4,889,818 A | 12/1989 | Gelfand et al. |
| 4,947,210 A | 8/1990 | Nagata et al. |
| 5,091,652 A | 2/1992 | Mathies et al. |
| 5,143,854 A | 9/1992 | Pirrung et al. |
| 5,171,695 A | 12/1992 | Ekins |
| 5,185,439 A | 2/1993 | Arnold, Jr. et al. |
| 5,223,409 A | 6/1993 | Ladner et al. |
| 5,242,828 A | 9/1993 | Bergstrom et al. |
| 5,283,174 A | 2/1994 | Arnold et al. |
| 5,288,644 A | 2/1994 | Beavis et al. |
| 5,292,658 A | 3/1994 | Cormier et al. |
| 5,313,264 A | 5/1994 | Ivarsson et al. |
| 5,322,770 A | 6/1994 | Gelfand |
| 5,324,633 A | 6/1994 | Fodor et al. |
| 5,399,491 A | 3/1995 | Kacian et al. |
| 5,403,484 A | 4/1995 | Ladner et al. |
| 5,409,818 A | 4/1995 | Davey et al. |
| 5,418,144 A | 5/1995 | Cormier et al. |
| 5,432,049 A | 7/1995 | Fischer et al. |
| 5,445,934 A | 8/1995 | Fodor et al. |
| 5,470,710 A | 11/1995 | Weiss et al. |
| 5,486,452 A | 1/1996 | Gordon et al. |
| 5,492,806 A | 2/1996 | Drmanac et al. |
| 5,498,538 A | 3/1996 | Kay et al. |
| 5,503,980 A | 4/1996 | Cantor |
| 5,510,270 A | 4/1996 | Fodor et al. |
| 5,516,637 A | 5/1996 | Huang et al. |
| 5,525,464 A | 6/1996 | Drmanac et al. |
| 5,532,128 A | 7/1996 | Eggers et al. |
| 5,538,848 A | 7/1996 | Livak et al. |
| 5,545,531 A | 8/1996 | Rava et al. |
| 5,547,732 A | 8/1996 | Edwards et al. |
| 5,547,839 A | 8/1996 | Dower et al. |
| 5,554,517 A | 9/1996 | Davey et al. |
| 5,556,752 A | 9/1996 | Lockhart et al. |
| 5,571,698 A | 11/1996 | Ladner et al. |

(Continued)

FOREIGN PATENT DOCUMENTS

| | | |
|---|---|---|
| AU | 2007273055 | 1/2008 |
| AU | 2011/248632 | 12/2012 |

(Continued)

OTHER PUBLICATIONS

NCT00470236 (first posted 2007) (Year: 2007).*
Chan et al (Breast Cancer Research 2011, 13: R19) (Year: 2011).*
Linke et al (Cancer Res 75, (9-supplement): P4-11-18, 2015) (Year: 2015).*
Bremer et al (J Clin Oncology 34: No. 15_suppl, p. 1019, 2016 (Year: 2016).*
U.S. Appl. No. 17/275,406, filed Mar. 11, 2021, Bremer.
Extended European Search Report dated Sep. 21, 2018, Received In European Patent Appl. No. 15865163.8.

(Continued)

*Primary Examiner* — Lei Yao

(74) *Attorney, Agent, or Firm* — KNOBBE, MARTENS, OLSON & BEAR, LLP

(57) ABSTRACT

The present disclosure provides compositions and methods for the treatment of subjects having a risk of invasive breast cancer. In some embodiments, these aspects allow for the pairing of the proper treatment option for the particular subject. In some embodiments, this allows for identifying subjects who, while at risk for invasive breast cancer, will not normally respond to radiation therapy, and can instead receive an alternative therapy, such as a HER2 antibody.

13 Claims, 3 Drawing Sheets

(56) References Cited

U.S. PATENT DOCUMENTS

| | | |
|---|---|---|
| 5,578,832 A | 11/1996 | Trulson et al. |
| 5,580,732 A | 12/1996 | Grossman et al. |
| 5,585,481 A | 12/1996 | Arnold, Jr. et al. |
| 5,593,839 A | 1/1997 | Hubbell et al. |
| 5,599,695 A | 2/1997 | Pease et al. |
| 5,625,033 A | 4/1997 | Kay et al. |
| 5,631,734 A | 5/1997 | Stern et al. |
| 5,648,211 A | 7/1997 | Fraiser et al. |
| 5,658,727 A | 8/1997 | Barbas et al. |
| 5,661,028 A | 8/1997 | Foote |
| 5,667,988 A | 9/1997 | Barbas et al. |
| 5,683,888 A | 11/1997 | Campbell |
| 5,723,591 A | 3/1998 | Livak et al. |
| 5,736,330 A | 4/1998 | Fulton |
| 5,741,668 A | 4/1998 | Ward et al. |
| 5,744,312 A | 4/1998 | Mamone et al. |
| 5,760,951 A | 6/1998 | Dixon et al. |
| 5,777,079 A | 7/1998 | Tsien et al. |
| 5,786,146 A | 7/1998 | Herman et al. |
| 5,800,992 A | 9/1998 | Fodor et al. |
| 5,804,387 A | 9/1998 | Cormack et al. |
| 5,807,522 A | 9/1998 | Brown et al. |
| 5,849,481 A | 12/1998 | Urdea et al. |
| 5,851,829 A | 12/1998 | Marasco et al. |
| 5,874,304 A | 2/1999 | Zolotukhin et al. |
| 5,876,146 A | 3/1999 | Deaver et al. |
| 5,876,930 A | 3/1999 | Livak et al. |
| 5,876,995 A | 3/1999 | Bryan |
| 5,904,915 A | 5/1999 | Fujibayashi et al. |
| 5,925,558 A | 7/1999 | Tsien et al. |
| 5,948,899 A | 9/1999 | Arnold et al. |
| 5,965,371 A | 10/1999 | Marasco et al. |
| 5,981,180 A | 11/1999 | Chandler et al. |
| 6,004,745 A | 12/1999 | Arnold et al. |
| 6,007,996 A | 12/1999 | McNamara et al. |
| 6,057,107 A | 5/2000 | Fulton |
| 6,063,603 A | 5/2000 | Davey et al. |
| 6,171,797 B1 | 1/2001 | Perbost |
| 6,180,351 B1 | 1/2001 | Cattell |
| 6,197,599 B1 | 3/2001 | Chin et al. |
| 6,225,047 B1 | 5/2001 | Hutchens et al. |
| 6,232,072 B1 | 5/2001 | Fisher |
| 6,242,266 B1 | 6/2001 | Schleifer et al. |
| 6,320,196 B1 | 11/2001 | Dorsel et al. |
| 6,323,043 B1 | 11/2001 | Caren et al. |
| 6,329,209 B1 | 12/2001 | Wagner et al. |
| 6,331,393 B1 | 12/2001 | Laird et al. |
| 6,355,934 B1 | 3/2002 | Osgood et al. |
| 6,579,684 B2 | 6/2003 | Price et al. |
| 6,610,484 B1 | 8/2003 | Hung |
| 6,797,393 B2 | 9/2004 | Qiao et al. |
| 6,919,211 B1 | 7/2005 | Fodor et al. |
| 7,011,949 B2 | 3/2006 | Amorese et al. |
| 7,081,340 B2 | 7/2006 | Baker et al. |
| 7,112,404 B2 | 9/2006 | Laird et al. |
| 7,186,512 B2 | 3/2007 | Martienssen et al. |
| 7,446,185 B2 | 11/2008 | Nelson |
| 7,452,727 B2 | 11/2008 | Henning et al. |
| 11,543,411 B2 | 1/2023 | Bremer et al. |
| 2002/0197676 A1 | 12/2002 | Lukyanov et al. |
| 2003/0225528 A1 | 12/2003 | Baker |
| 2003/0225529 A1 | 12/2003 | Ecker et al. |
| 2005/0032085 A1 | 2/2005 | Labas et al. |
| 2006/0063190 A1 | 3/2006 | Fischer et al. |
| 2006/0129331 A1 | 6/2006 | Akilesh et al. |
| 2006/0275844 A1 | 12/2006 | Linke et al. |
| 2007/0009915 A1 | 1/2007 | Wang |
| 2007/0077582 A1 | 4/2007 | Slepnev |
| 2007/0105133 A1 | 5/2007 | Clarke et al. |
| 2010/0003189 A1 | 1/2010 | Tlsty et al. |
| 2010/0068717 A1 | 3/2010 | Badve et al. |
| 2010/0158894 A1 | 6/2010 | Umemura |
| 2011/0183333 A1 | 7/2011 | Martin et al. |
| 2012/0003639 A1 | 1/2012 | Kerlikowske et al. |
| 2013/0317083 A1 | 11/2013 | Rigoutsos |
| 2017/0184601 A1 | 6/2017 | Tlsty et al. |
| 2017/0350895 A1* | 12/2017 | Bremer ............ G01N 33/57415 |
| 2022/0187301 A1 | 6/2022 | Bremer |
| 2023/0136619 A1 | 5/2023 | Bremer et al. |
| 2023/0204591 A1 | 6/2023 | Tlsty et al. |

FOREIGN PATENT DOCUMENTS

| | | |
|---|---|---|
| AU | 2013205536 | 5/2013 |
| AU | 2013205531 | 11/2016 |
| CA | 2657576 | 1/2008 |
| EP | 0244210 | 11/1989 |
| EP | 0204187 | 10/1990 |
| EP | 0245071 | 1/1992 |
| EP | 0329822 | 6/1994 |
| EP | 0373203 | 8/1994 |
| EP | 0721 016 | 7/1996 |
| EP | 0728520 | 5/2001 |
| EP | 0785280 | 4/2003 |
| EP | 0799897 | 6/2006 |
| EP | 2041574 | 4/2009 |
| EP | 2442108 | 4/2012 |
| EP | 2442109 | 4/2012 |
| EP | 2450710 | 5/2012 |
| EP | 2564200 | 3/2013 |
| EP | 3508854 | 7/2019 |
| WO | WO 1991/02814 | 3/1991 |
| WO | WO 1992/15673 | 9/1992 |
| WO | WO 1995/00669 | 1/1995 |
| WO | WO 1995/07463 | 3/1995 |
| WO | WO 1995/21265 | 8/1995 |
| WO | WO 1995/22058 | 8/1995 |
| WO | WO 1995/35505 | 12/1995 |
| WO | WO 1996/31622 | 10/1996 |
| WO | WO 1997/02357 | 1/1997 |
| WO | WO 1997/10365 | 3/1997 |
| WO | WO 1997/27317 | 7/1997 |
| WO | WO 1997/29212 | 8/1997 |
| WO | WO 1998/14605 | 4/1998 |
| WO | WO 1998/26277 | 6/1998 |
| WO | WO 1999/39210 | 8/1999 |
| WO | WO 1999/49019 | 9/1999 |
| WO | WO 1999/51773 | 10/1999 |
| WO | WO 2000/04382 | 1/2000 |
| WO | WO 2000/04389 | 1/2000 |
| WO | WO 2000/04390 | 1/2000 |
| WO | WO 2000/54046 | 9/2000 |
| WO | WO 2000/56934 | 9/2000 |
| WO | WO 2001/14425 | 3/2001 |
| WO | WO 2001/40803 | 6/2001 |
| WO | WO 2002/019767 | 3/2002 |
| WO | WO 2000/63701 | 6/2002 |
| WO | WO 2005/038051 | 4/2005 |
| WO | WO 2005/083429 | 9/2005 |
| WO | WO 2008/008284 | 1/2008 |
| WO | WO 2011/139721 | 11/2011 |
| WO | WO 2016/090323 | 6/2016 |
| WO | WO 2020/056338 | 3/2020 |

OTHER PUBLICATIONS

Office Action dated Dec. 21, 2020 Received In European Patent Application No. Ep15865163.8 In 3 Pages.

Office Action, dated Nov. 25, 2019, For European Patent Application No. 15 865 163.8.

Partial European Search Report, dated May 23, 2018, In European Patent Application No. Ep 15 865 163.8

International Search Report & Written Opinion, dated Feb. 16, 2016, In International Application PCT/Us2015/064115.

International Search Report And Written Opinion, dated Dec. 5, 2019, For International Application No. PCT/Us2019/051128.

International Search Report dated Sep. 19, 2008, From International Application No. PCT/US07/15584, Filed Apr. 26, 2011.

Office Action dated Jan. 3, 2019 In U.S. Appl. No. 15/284,349.

Office Action dated Jul. 28, 2017 In U.S. Appl. No. 15/248,349.

Office Action dated Sep. 16, 2019 in U.S. Appl. No. 15/284,349.

Office Action dated May 31, 2018 in Canadian Patent Application Np. 2,657,576.

(56) References Cited

OTHER PUBLICATIONS

Office Action dated Nov. 29, 2018 in European Patent Application No. 11188923.4.
Office Action dated Sep. 16, 2019 in European Patent Application No. 11188923.4.
Office Action dated Nov. 10, 2014 in Australian Patent Application No. 2013205531.
Office Action dated Nov. 10, 2014 in Australian Patent Application No. 2013205536.
Final Office Action dated Dec. 21, 2020 in U.S. Appl. No. 15/284,349.
Office Action dated Feb. 12, 2018 in U.S. Appl. No. 15/248,349.
Office Action received in U.S. Appl. No. 15/284,349 dated Sep. 23, 2021.
U.S. Office Action dated Jun. 24, 2020, in U.S. Appl. No. 15/284,349.
Office Action dated Apr. 10, 2012 in U.S. Appl. No. 12/373,047.
Office Action dated Jun. 23, 2011 in U.S. Appl. No. 12/373,047.
Office Action dated Jun. 3, 2016 in U.S. Appl. No. 12/373,047.
Office Action dated May 29, 2015 in U.S. Appl. No. 12/373,047.
Office Action dated Sep. 24, 2014 in U.S. Appl. No. 12/373,047.
Office Action dated Jul. 25, 2012, received in Australian Patent Application No. 2007273055, filed on Jul. 3, 2007.
Office Action dated Mar. 25, 2014, received in Australian Application No. 2007273055.
Office Action dated Dec. 15, 2014 in Canadian Application No. 2657576.
Office Action dated Dec. 19, 2016 in Canadian Application No. 2,657,576.
Office Action dated Jun. 21, 2017 in Canadian Application 2,657,576.
Office Action dated Nov. 20, 2013, received in Canadian Appl. No. 2,657,576.
European Office Action dated Aug. 5, 2009, received in European Patent Appl. No. 07810252.2.
Office Action dated Aug. 11, 2014, received in European Application No. 07810252.2.
Office Action dated Dec. 12, 2012 received in European Patent Appl. No. 07810252.2-2401.
Office Action dated Dec. 8, 2010, received in European Patent Appl. No. 07810252.2.
Office Action dated Feb. 9, 2012 received in European Patent Application No. 07 810 252.
Office Action dated Jul. 18, 2011, received in European Patent Application No. 07810252.2.
Office Action dated Jun. 16, 2015 in European Patent Application No. 07810252.2.
Office Action dated May 31, 2010, received in European Patent Appl. No. 07810252.2.
Office Action dated Oct. 17, 2013 in European Patent Application No. 07810252.2.
European Search Report received in European Patent Application No. EP 11 18 8923, filed Jul. 3, 2007.
Office Action dated Feb. 18, 2013, received in European Application No. 11188923.4, 6 pages.
Office Action dated Jul. 15, 2014, received in European Application No. 11188923.4.
Office Action dated Jun. 12, 2017 in European Application No. 11188923.4.
Office Action dated May 12, 2016 in European Application No. 11188923.4.
Office Action dated May 18, 2015 in European Patent Application No. 11188923.4.
Office Action dated Sep. 20, 2013 in European Application No. 11188923.4.
European Search Report received dated Jun. 27, 2012 received in European Patent Application No. 11188923.4, filed on Jul. 3, 2007.
European Publication received in European Patent Application No. EP 11 18 8925, filed Jul. 3, 2007.
Office Action dated Jul. 15, 2014, received in European Application No. 11188925.9.
Office Action dated Mar. 4, 2013, received in European Application No. 11188925.9, 6 pages.
Office Action dated May 18, 2015 in European Patent Application No. 11188925.9.
Office Action dated Sep. 26, 2013 in European Application No. 11188925.9.
European Search Report dated Mar. 20, 2012 in European Patent Application No. EP 11 18 8926, filed Jul. 3, 2007.
Office Action dated Jul. 15, 2014, received in European Application No. 11188926.7.
Office Action dated Mar. 4, 2013, received in European Application No. 11188926.7, 5 pages.
Office Action dated May 18, 2015 in European Patent Application No. 11188926.7.
Office Action dated Sep. 26, 2013 in European Patent Application No. 11188926.7.
Extended European Search Report dated Jan. 20, 2021, received in European Patent Appl. No. 20190672.4.
Office Action dated Mar. 10, 2014, received in Japanese Appl. No. 2009-520751 (with English translation).
Office Action dated Oct. 24, 2014, received in Japanese Appl. No. 2009-520751 (with English translation).
Office Action, dated Jan. 8, 2013, received in Japanese Patent Appl. No. 2009-520751, and translation.
Final Office Action dated Mar. 15, 2021 in U.S. Appl. No. 13/094,729.
Office Action dated Apr. 11, 2014, received in U.S. Appl. No. 13/094,729.
Office Action dated Apr. 27, 2016, received in U.S. Appl. No. 13/094,729.
Office Action dated Aug. 3, 2021 received in U.S. Appl. No. 13/094,729 in 32 pages.
Office Action dated Dec. 5, 2016, received in U.S. Appl. No. 13/094,729.
Office Action dated Jul. 23, 2015 in U.S. Appl. No. 13/094,729.
Office Action dated Mar. 24, 2017, received in U.S. Appl. No. 13/094,729.
Office Action dated Mar. 29, 2019 in U.S. Appl. No. 13/094,729.
Office Action dated Oct. 8, 2019 in U.S. Appl. No. 13/094,729.
Office Action dated Sep. 17, 2013, received in U.S. Appl. No. 13/094,729.
Office Action dated Sep. 26, 2018 in U.S. Appl. No. 13/094,729.
Office Action, dated Mar. 16, 2018, in U.S. Appl. No. 13/094,729.
U.S. Office Action dated Jan. 18, 2022, received in U.S. Appl. No. 13/094,729.
U.S. Office Action dated Jun. 8, 2020, received in U.S. Appl. No. 13/094,729.
Office Action dated Sep. 19, 2013 in Australian Application No. 2011248632.
Canadian Office Action dated Dec. 1, 2017, Canadian Application No. 2,797,585.
Canadian Office Action dated Dec. 9, 2015, received in Canadian Appl. No. 2,657,576.
Canadian Office Action dated Jun. 14, 2021, received in Canadian Appl. No. 2,657,576.
Canadian Office Action dated Jun. 30, 2020, received in Canadian Appl. No. 2,657,576.
Canadian Office Action dated Jun. 7, 2019, Canadian Application No. 2,797,585.
Canadian Office Action dated May 1, 2020, Canadian Application No. 2,797,585.
Office Action dated Apr. 21, 2017 in Canadian Application 2,797,585.
Office Action dated Apr. 7, 2021 in Canadian Application No. 2,797,585.
Office Action, dated Feb. 23, 2018, in European Patent Application No. 11 188 923.4.
Office Action, dated Jun. 7, 2019, in Canadian Application 2,797,585.
Office Action, dated May 1, 2020, in Canadian Application 2,797,585.
Communication pursuant to Rules 161 (1) and 162 EPC dated Dec. 7, 2012 in European Application No. 11721599.6.
Office Action dated Apr. 15, 2016 in European Application No. 11721599.6.
Office Action dated Dec. 7, 2012 in European Application No. 11721599.6.
Office Action Dated Mar. 6, 2017 in European Application No. 11721599.6.

(56) References Cited

OTHER PUBLICATIONS

Office Action dated Sep. 30, 2014 in European Application No. 11721599.6.
Office Action, dated Apr. 19, 2018, in European Patent Application Np. 11 721 599.6.
European Office Action dated Jun. 11, 2021 in European Patent Application No. 18209239.5.
European Search Reported dated Mar. 19, 2019 in European Patent Application No. 18209239.5.
International Search Report and Written Opinion dated Sep. 14, 2011, from International Application No. PCT/US2011/034005, filed Apr. 26, 2011.
Affymetrix Genechip U133 Plus 2.0 Array Dated Sheet (2004-2005).
Albergaria, et al. Expression of FOXA1 and GATA-3 in Breast Cancer: The Prognostic Significance in Hormone Receptor-Negative Tumors, Breast Cancer Research, vol. 11 No. 3, pp. 1-15 (2009).
Allred, D. C., et al., Adjuvant tamoxifen reduces subsequent breast cancer in women with estrogen receptor-positive ductal carcinoma in situ: a study based on NSABP protocol B-24, Journal of clinical oncology : official journal of the American Society of Clinical Oncology, vol. 30, No. 12, pp. 1268-1273, 2012.
Annual Meeting Of Japanese Society Of National Medical Service, 2005, 59th, 357-763.
Arbiser, JI. "Molecular Regulation Of Angiogenesis And Tumorigenesis By Signal Transduction Pathways: Evidence Of Predictable And Reproducible Patterns Of Synergy In Diverse Neoplasms", Semin Cancer Biol. 14 (2004) 81-91.
Badve Et Al, FOXA 1 Expression 1 N Breast Cancer Correlation With Luminal Subtype A And Survival, Clin Cancer Res, vol. 13, pp. 4415-4421, Aug. 1, 2007.
Bartova, M, et al., COX-2, P16 And Ki67 Expression In DCIS, Microinvasive And Early Invasive Breast Carcinoma With Extensive Intraductal Component, Bratislava Medical Journal, vol. 115, No. 7, pp. 445-451, (2014).
Baughey et al. Current Treatment And Clinical Trial Developments For Ductal Carcinoma In Situ Of The Breast Baughey Et Al. The Oncologist; 2007;12:1276-1287.
Behling, K Et Al., Increased SIAH Expression Predicts Ductal Carcinoma In Situ (DCIS) Progression To Invasive Carcinoma, Breast Cancer Research And Treatment, vol. 129, No. 3, pp. 717-724, (2011).
Belvisi, M. Et Al., "Induction Of Cyclo-Oxygenase-2 By Cytokines In Human Cultured Airway Smooth Muscle Cells: Novel Inflammatory Role Of This Cell Type," British Journal Of Pharmacology, 1997, vol. 120, pp. 910-916.
Boland, G. Et Al, Cox-2 Expression Is Associated With An Aggressive Phenotype In Ductal Carcinoma In Situ, British Journal Of Cancer, vol. 90, pp. 423-429, (2004).
Bouvier-Labit, C. et al., P16ink4 And P19ink4d Mrna Expression In Neurological Tumours: Correlation With Ki67 Proliferation Index, Neuropathology And Applied Neurobiology, vol. 25, pp. 408-416, (1999).
Breastcancer.Org (Apr. 2, 2014) available at https://www.breastcancer.org/research-news/20110402. This reference is a webpage and the date apparent on the webpage is listed herewith. However, the webpage may have been available, in some form, prior to this date.
Breastcancer.Org 2011 (Mar. 16, 2011) available at https://www.breastcancer.org/research-news/20110316. This reference is a webpage and the date apparent on the webpage is listed herewith. However, the webpage may have been available, in some form, prior to this date.
Breastcancer.Org 2013 (Oct. 4, 2013) available at https://www.breastcancer.org/research-news/20131004. This reference is a webpage and the date apparent on the webpage is listed herewith. However, the webpage may have been available, in some form, prior to this date.
Burstein, H. Et Al. Ductal Carcinoma In Situ Of The Breast, The New England Journal Of Medicine, vol. 350, No. 14, pp. 1430-1441, (2004).
Chan Et Al., The Expression Of The Ublquitin Ligase SIAH2 (Seven In Absentia Homolog 2) Is Mediated Through Gene Copy Number In Breast Cancer And Is Associated With A Basal-Like Phenotype And P53 Expression, Breast Cancer Res vol. 13, R19, Feb. 9, 2011.
Chan, E. Integrating Transcriptomics And Proteomics. Drug Discovery And Development, Apr. 1, 2006, 6(3) 20-26.
Cheng Et Al (Journal Of The National Cancer Institute, 1997, 89: 1356-1360).
Chivukula Et Al (Ductal Carcinoma In Situ: One Size Does Not Fit All. Women's Health. Sep. 2010:669-672).
Chow, L.W.C., Et Al., "Study Of Cox-2, Ki67, And P53 Expression To Predict Effectiveness Of 5-Flurouracil, Epirubicin And Cyclophosphamide With Celecoxib Treatment In Breast Cancer Patients", Biomedicine & Pharmacotherapy, vol. 59, pp. S298-S301, 2005.
Crawford Et Al., "Histologically Normal Human Mammary Epithelia With Silenced P16(Ink4a) Overexpress Cox-2, Promoting A Premalignant Program," Cancer Cell 2004;5(3):263-73.
Cuzick, I. S., et al., Effect of tamoxifen and radiotherapy in women with locally excised ductal carcinoma in situ: long-term results from the UK/ANZ DCIS trial, The Lancet Oncology, vol. 12, Issue 1, pp. 21-29, 2011.
Darling, Maria L. Rosenfield et al., "Atypicalductal Hyperplasia And Ductal Carcinoma In Situ As Revealed By Large-Core Needle Breast Biopsy: Results Of Surgical Excision," American Journal Of Roentgenology, 2000, vol. 175, pp. 1341-1346.
Davies Et Al., "Correlation Between Cyclooxygenase-2 Expression And Angiogenesis In Human Breast Cancer", Clinical Cancer Research, vol. 9, pp. 2651-2656, Jul. 2003.
Declaration By Troy Bremer And Exhibits (A-G) In U.S. Appl. No. 13/094,729, Dated Nov. 9, 2020.
Declaration By Troy Bremer in U.S. Appl. No. 15/529,966, dated Feb. 2, 2021.
Dedeoglu, Analysis Of Differentially Expressed Genes In Breast Cancer: Brca1-Induced Gene Expression Profiles And Meta-Analysis Gene Signature, Thesis Submitted To Bilkent University, (2009).
Di Vinci Et Al., "P16ink4a Promoter Methylation And Protein Expression In Breast Fibroadenoma And Carcinoma," Int. J. Cancer, 2005, pp. 414-421, vol. 114.
Dunne Et Al., Effect Of Margin Status On Local Recurrence After Breast Conservation And Radiation Therapy For Ductal Carcinoma In Situ, Journal Of Clinical Oncology, vol. 27, No. 10, 2009.
Dwek Et Al. Proteome And Glycosylation Mapping Identifies Post-Translational Modifications Associated With Aggressive Breast Cancer. Proteomics 2001, 1, 756-762.
Ernster, V., Et Al., Detection Of Ductal Carcinoma In Situ In Women Undergoing Screening Mammography, Journal Of The National Cancer Institute, vol. 94, No. 20, (2002).
Expression Probeset Details For HG-U133A:201930_S_AT (This Document Was Printed From The World Wide Web At Www.Affymetrix.Com/Analysis/Netaffx/Fullrecord.Affx?Pk=HG-U133A:210930_S_AT On Sep. 11, 2013. The Original Publication Date Is Unknown.).
Faratian Et Al., "Membranous And Cytoplasmic Staining Of Ki67 Is Associated With HER2 And ER Status In Invasive Breast Carcinoma." Histopathology 54.2 (Jan. 2009): 254-257.
File History, U.S. Appl. No. 12/373,047, filed May 13, 2009.
File History, U.S. Appl. No. 13/094,729, filed Apr. 26, 2011.
File History, U.S. Appl. No. 15/248,349, filed Oct. 3, 2016.
File History, U.S. Appl. No. 15/529,966, filed May 25, 2017.
File History, U.S. Appl. No. 17/275,406, filed Mar. 11, 2021.
Fisher et al. Prevention of invasive breast cancer in women with ductal carcinoma in situ: An update of the National Surgical Adjuvant Breast and Bowel Project experience, Seminars in Oncology, vol. 28, Issue 4, pp. 400-418, 2001.

(56) References Cited

OTHER PUBLICATIONS

Gauthier Et Al., "Abrogated Response To Cellular Stress Identifies Dcis Associated With Subsequent Tumor Events And Defines Basal-Like Breast Tumors." Cancer Cell. 12.5 (Nov. 2007): 479-491.
Gauthier Et Al., "P38 Regulates Cycloxygenase-2 In Human Mammary Epithelial Cells And Is Activated In Premalignant Tissue", Cancer Res , vol. 65, No. 5, pp. 1792-1799, Mar. 1, 2005.
Gorringe, K, Et Al. Ductal Carcinoma In Situ Biology, Biomarkers And Diagnosis, Frontiers In Oncology, vol. 7, Article, 248, pp. 1-14, (2017).
Hammond Et Al., American Society Of Clinical Oncology/College Of American Pathologists Guideline Recommendations For Immunohistochemical Testing Of Estrogen And Progesterone Receptors In Breast Cancer /Unabridged Version) Arch Pathol Lab Med. vol. 134. E48 Jul. 1, 2010.
Horimoto Et Al., Low Foxa 1 Expression Predicts Good Response To Neo-Adjuvant Chemotherapy Resulting In Good Outcomes For Luminal Her2-Negative Breast Cancer Cases, British Journal Of Cancer, vol. 112, Nn. 345-351, Eoub Nov. 25, 2014.
Hoshikawa Et Al. Hypoxia Induces Different Genes In The Lungs Of Rats Compared With Mice. Physiol. Genomics 12: 209-219, 2003.
Iorio Et Al., "Microrna Gene Expression Deregulation In Human Breast Cancer", Cancer Res, vol. 65, No. 16, pp. 7065-7070, Aug. 15, 2005.
Joyce Et Al., Effect Of Overexpressing The Transcription Factor E2f2 On Cell Cycle Progression In Rabbit Corneal Endothelial Cells, Investigative Ophthalmology & Visual Science, May 2004, vol. 45, No. 5.
Kenny Et Al., "Quantification Of Cellular Proliferation In Tumor And Normal Tissues Of Patients With Breast Cancer By [18f]Fluorothymidine-Positron Emission Tomography Imaging: Evaluation Of Analytical Methods", Cancer Res, vol. 65, No. 21, pp. 10104-10112, Nov. 1, 2005.
Kepple, J Et Al., "The Receptor Expression Pattern In Ductal Carcinoma In Situ Predicts Recurrence", The American Journal Of Surgery, 192 (2006) 68-71.
Kerlikowske Et Al., "Biomarker Expression And Risk Of Subsequent Tumors After Initial Ductal Carcinoma In Situ Diagnosis", J Natl Cancer Inst, vol. 102 No. 9, pp. 627-637 (May 5, 2010).
Kerlikowske Et Al., "Characteristics Associated With Recurrence Among Women With Ductal Carcinoma In Situ Treated By Lumpectomy", J. Natl Cancer Inst, vol. 95 No. 22, pp. 1692-1702 (2003).
Lari Et Al. Biological Markers in DCIS and Risk of Breast Recurrence: A Systematic Review, Journal of Cancer, vol. 2, pp. 232-261,2011.
Lee Et Al., Context-Specific Regulation Of Nf-Kb Target Gene Expression By Ezh2 In Breast Cancers, Mol Cell, vol. 43, pp. 798-810, Sep. 2, 2011.
Marsh, K, Et Al. Frequent Alterations Of Cell Cycle Regulators In Early-Stage Breast Lesions As Detected By Immunohistochemistry, British Journal Of Cancer, vol. 77, No. 9, pp. 1460-1468, (1998).
Marsh, KL Et Al., "Loss Of Heterozygosity At Chromosome 9p In Ductal Carcinoma In Situ And Invasive Carcinoma Of The Breast," British Journal Of Cancer, 1998, vol. 77, No. 9, pp. 1439-1447.
Mohsin, S. Et Al. Progesterone Receptor By Immunohistochemistry And Clinical Outcome In Breast Cancer: A Validation Study, Modern Pathology, vol. 17, pp. 1545-1554, (2004).
Muggerud, A., Et Al, Molecular Diversity In Ductal Carcinoma In Situ (Dcis) And Early Invasive Breast Cancer, Molecular Oncology, vol. 4, No. 4, pp. 357-368, (2010).
Mylonas Et Al., "Expression Of Her2/Neu, Steroid Receptors (Er And Pr), Ki67 And P53 In Invasive Mammary Ductal Carcinoma Associated With Ductal Carcinoma In Situ (Dcis) Versus Invasive Breast Cancer Alone." Anticancer Research. 25.3a (May 2005): 1719-1723.

Nofech-Mozes Et Al., "Biological Markers Predictive Of Invasive Recurrence In Dcis", Clinical Medicine: Oncology, vol. 2, pp. 7-18, 2008.
Patani Et Al., "Current Management Of Dcis: A Review", Breast Cancer Res Treat, vol. 111, pp. 1-10, 2008.
Perrone Et Al., "Cox-2 Expression In Dcis: Correlation With Vegf, Her-2/Neu, Prognostic Molecular Markers And Clinicopathological Features." Histopathology. 46.5 (May 2005): 561-568.
Picarsic Et Al. Predictors of invasive breast cancer or DCIS recurrence in estrogen receptor positive (ER+) and estrogen receptor negative (ER−) ductal carcinoma in situ (DCIS) patients with and without associated invasive carcinoma (IC) (Journal Of Clinical Oncology, 2009, 27, No. 15_Suppl; Abstract E11523).
Picarsic et al., Role of Transcription Factors [FOXA1,GATA-3] in Predicting Outcomes in Recurrent Ductal Carcinoma-In-Situ (DCIS) or Invasive Carcinoma (IC) in DCIS Patients on Core Needle Biopsies of Breast. Cancer Res (2009) 69 (24_Supplement): 2115.
Plon, S.E., "Screening And Clinical Implications For Brca1 And Brca2 Mutation Carriers", Journal Of Mammary Gland Biology And Neoplasia, vol. 3, No. 4, pp. 377-387, 1998.
Prelude Press Release Dated Aug. 2, 2018 Entitled Journal Of Clinical Cancer Research Publication Demonstrates That Dcisionrt® Provides Prognostic And Predictive Power For Assessing A Patient's Dcls Risk.
Provenzano Et Al., "Biological Markers That Predict Clinical Recurrence In Ductal Carcinoma In Situ Of The Breast", European Journal Of Cancer 39, pp. 622-630, 2003.
Ruiz Et Al., "Tissue Microarrays For Comparing Molecular Features With Proliferation Activity In Breast Cancer," Int. J. Cancer, 2006, pp. 2190-2194, vol. 118.
Salido, M. Et Al., Polysomy Of Chromosome 17 In Breast Cancer Tumors Showing An Overexpression Of Erbb2: A Study Of 175 Cases Using Fluorescence In Situ Hybridization And Immunohistochemistry, Breast Cancer Res, vol. 7, No. 2, pp. R267-R273, (2005).
Schorr Et Al., "Are The Pure In Situ Breast Ductal Carcinomas And Those Associated With Invasive Carcinoma The Same?" Applied Immunohistochemistry And Molecular Morphology 18.1 (Jan. 2010): 51-54.
Sendur, M.A.N., Et Al., Cadiotoxicity Of Novel Her2-Targeted Therapies, Current Medical Research And Opinion, vol. 29, No. 8, pp. 1015-1024, 2013.
Shah, Et Al., The Clinical Utility Of Dcisionrt On Radiation Therapy Decision Making In Patients With Ductal Carcinoma In Situ Following Breast-Conserving Surgery. Ann Surg Oncol, vol. 28, pp. 5974-5984, 2021.
Steinman, S. Et Al, Expression Of Cytokeratin Markers, Er-Alpha, Pr, Her-2/New, And Egfr In Pure Ductal Carcinoma In Situ (Dcis) And Dcis With Co-Existing Invasive Ductal Carcinoma (Idc) Of The Breast, Annals Of Clinical & Laboratory Science, vol. 37, No. 2, pp. 127-134, (2007).
Stoll, B.A., "Premalignant Breast Lesions: Role For Biological Markers In Predicting Progression To Cancer", European Journal Of Cancer, vol. 35, No. 5, pp. 693-697, 1999.
Tlsty Et Al., "Genetic And Epigenetic Changes In Mammary Epithelial Cells May Mimic Early Events In Carcinogenesis", Journal Of Mammary Gland Biology And Neoplasia, vol. 9, No. 3, pp. 263-274, Jul. 2004.
Tuomisto Et Al., "Analysis Of Gene And Protein Expression During Monocyte-Macrophage Differentiation And Cholesterol Loading-Cdna And Protein Array Study", Atherosclerosis, vol. 180, pp. 283-291, 2005.
Ushijima Et Al. Genes Involved In Breast Cancers. Nippon Rinsho, Mar. 2006, 64(3): 432-436.
Van Der Groep Et Al., "Molecular Profile Of Ductal Carcinoma In Situ Of The Breast In Brca1 And Brca2 Germline Mutation Carriers." Journal Of Clinical Pathology. 62.10 (Oct. 2009): 926-930.
Vicini, 2021, American Society Of Radiation Oncology Annual Meeting.
Whitehead et al. Variation In Tissue-Specific Gene Expression Among Natural Populations. Genome Biology 2005, 6:R13, In 14 Pages.

(56) References Cited

OTHER PUBLICATIONS

Wiechmann, L Et Al., "The Molecular Journey From Ductal Carcinoma In Situ To Invasive Breast Cancer," American Cancer Society, 2008, vol. 112, pp. 2130-2142.
Witkiewicz, A. Et Al., "Associate Of Rb/P16-Pathway Perturbations With Dcis Recurrence" The American Journal Of Psychology, vol. 179, No. 3, Sep. 2011.
Wolf et al., FOXA1: Growth Inhibitor and a Favorable Prognostic Factor in Human Breast Cancer, Int. J. Cancer, vol. 120, pp. 1013-1022, (2006).
Wood, The Role Of Clinical Trials In Changing Therapy For Ductal Carcinoma In Situ. Annals Of Surgical Oncology, 2004; 11 (1):24s-27s.
Yu, K. Et Al. Gene Expression Patterns Of Tumor Progression In Different Breast Cancer Molecular Subtypes From An Asian-Chinese Population, Proc. Amer. Association Cancer Res., vol. 25, (2004).
Zhou Et Al., "A Comparison Of Tumor Biology In Primary Ductal Carcinoma In Situ Recurring As Invasive Carcinoma Versus A New In Situ", International Journal Of Breast Cancer, vol. 2013, Jan. 1, 2013.
Zhou, W, Aspects Of Progression In Breast Carcinoma, From Ductal Carcinoma In Situ To Invasive Cancer, Acta Universitatis Upsaliensis Uppsala, Uppsala University, Department Of Surgical Sciences, Akademiska Sjukhuset, Se-751 85, Uppsala, Sweden, *Digital Comprehensive Summaries Of Uppsala Dissertations From The Faculty Of Medicine* 735. 38 Pp. Uppsala (2012).
Zhou, W. et al., "Tumor Markers Predicting Recurrence Type After A Primary Ductal Carcinoma In Situ., Cancer Research", Cancer Research, vol. 71, No. 24, P4-10-01, Dec. 1, 2012.
Office Action dated Dec. 7, 2021 in U.S. Appl. No. 15/529,966 in 35 pages.
Office Action dated Mar. 2, 2020 in U.S. Appl. No. 15/529,966 in 37 pages.
Office Action dated Mar. 18, 2019 in U.S. Appl. No. 15/529,966 in 31 pages.
Office Action dated Oct. 23, 2017 in U.S. Appl. No. 15/529,966 in 14 pages.
U.S. Office Action dated Nov. 9, 2022 in U.S. Appl. No. 15/284,349.
Response to U.S. Office Action dated Nov. 9, 2022, filed Mar. 2, 2023 in U.S. Appl. No. 15/284,349.
U.S. Office Action dated May 9, 2023 in U.S. Appl. No. 15/284,349.
U.S. Office Action dated Jan. 12, 2023 in U.S. Appl. No. 17/664,006.
Response to U.S. Office Action dated Jan. 12, 2023, filed Mar. 23, 2023 in U.S. Appl. No. 17/664,006.
U.S. Office Action dated Apr. 4, 2023 in U.S. Appl. No. 17/664,006.
Response to European Office Action dated Nov. 2, 2022, filed Mar. 10, 2023 in EP Application No. EP15865163.8.
EP Communication pursuant to Rules 70(2) and 70a(2) EPC, dated Nov. 8, 2022 in European Patent Appl. No. 19859855.9.
Response to EP Communication 70(2) dated Nov. 8, 2022, filed May 12, 2023 in European Patent Appl. No. 19859855.9.
U.S. Appl. No. 17/664,006, filed May 18, 2022, Tlsty.
U.S. Appl. No. 17/652,466, filed Feb. 24, 2022, Bremer.
Marsh et al., "Frequent alterations of cell cycle regulators in early-stage breast lesions as detected by immunohistochemistry," Br J Cancer, 1998, vol. 77, No. 9, pp. 1460-1468.
Siewertsz van Reesema L. et al., "SIAH and EGFR; Two RAS Pathway Biomarkers are Highly Prognostic in Locally Advanced and Metastatic Breast Cancer". EBioMedicine. Sep. 1, 2016;11: 183-198.
Solin, L. J. et al., "A Multigene Expression Assay to Predict Local Recurrence Risk for Ductal Carcinoma In Situ of the Breast". J Nat Cancer Inst., May 15, 2013; 105(10): 701-710.
Tsikitis et al., "Biology of Ductal Carcinoma in Situ Classification Based on Biologic Potential," Am J Clin Oncol. 2006; 29: 305-310.
Wärnberg et al., "Abstract GS5-08: A Validation of DCIS Biiological Risk Profile in a Randomised Study for Radiation Therapy with 20 Year Follow-up (SweDCIS)". Cancer Res. Feb. 15, 2018; Abstract.
Yang M. et al., "Microinvasive ductal carcinoma {T1 mic) of the breast. The clinicopathological profile and immunohistochemical features of 28 cases". Pathol Inter'l. 2003; vol. 53, pp. 422-428.
Response to U.S. Office Action dated Jun. 23, 2011, filed Sep. 23, 2011 in U.S. Appl. No. 12/373,047.
Response to U.S. Office Action dated Apr. 10, 2012, filed Jul. 9, 2012 in U.S. Appl. No. 12/373,047.
Response to U.S. Office Action dated Sep. 24, 2014, filed Mar. 23, 2015 in U.S. Appl. No. 12/373,047.
Response to U.S. Office Action dated May 29, 2015, filed Nov. 20, 2015 in U.S. Appl. No. 12/373,047.
Response to U.S. Office Action dated Jul. 28, 2017, filed Oct. 30, 2017 in U.S. Appl. No. 15/284,349.
Response to U.S. Office Action dated Feb. 12, 2018, filed Jun. 11, 2018 in U.S. Appl. No. 15/284,349.
Response to U.S. Office Action dated (Jan. 3, 2019), filed Jul. 1, 2019 in U.S. Appl. No. 15/284,349.
Response to U.S Office Action dated Sep. 16, 2019, filed Dec. 13, 2019 in U.S. Appl. No. 15/284,349.
Response to U.S. Office Action dated Jun. 24, 2020, filed Sep. 24, 2020 in U.S. Appl. No. 15/284,349.
Response to U.S. Office Action dated Dec. 21, 2020 filed May 20, 2021 in U.S. Appl. No. 15/284,349.
U.S. Advisory Action dated Jun. 1, 2021 in U.S. Appl. No. 15/284,349.
Response to U.S. Office Action dated Sep. 23, 2021 filed Dec. 17, 2021 in U.S. Appl. No. 15/284,349.
U.S. Office Action dated Mar. 11, 2022 in U.S. Appl. No. 15/284,349.
Response to U.S. Office Action dated Mar. 11, 2022, filed Aug. 5, 2022 in U.S. Appl. No. 15/284,349.
Response to Office Action dated Sep. 17, 2013, filed on Mar. 14, 2014 in U.S. Appl. No. 13/094,729.
U.S. Office Action dated Apr. 11, 2014 in U.S. Appl. No. 13/094,729.
Response to Office Action dated Apr. 11, 2014, filed on Jul. 11, 2014 in U.S. Appl. No. 13/094,729.
Response to Office Action dated Jul. 23, 2015 filed on Jan. 21, 2016 in U.S. Appl. No. 13/094,729.
Response (Supplemental) to Office Action dated Jul. 23, 2015, filed on Apr. 14, 2016 in U.S. Appl. No. 13/094,729.
Response to Office Action dated Apr. 27, 2016 filed on Sep. 27, 2016 in U.S. Appl. No. 13/094,729.
Response to Office Action dated Dec. 5, 2016 filed on Mar. 6, 2017 in U.S. Appl. No. 13/094,729.
Response to Office Action dated Mar. 24, 2017 filed on Jun. 26, 2017 in U.S. Appl. No. 13/094,729.
Response to Office Action dated Mar. 16, 2018, filed on Jun. 14, 2018 in U.S. Appl. No. 13/094,729.
Response to Office Action dated Sep. 26, 2018 filed on Feb. 25, 2019 in U.S. Appl. No. 13/094,729.
Response to Office Action dated Mar. 29, 2019, filed on Jul. 1, 2019 in U.S. Appl. No. 13/094,729.
Response to Office Action dated Oct. 8, 2019, filed Feb. 11, 2020 in U.S. Appl. No. 13/094,729.
Response to Office Action dated Jun. 8, 2020, filed on Nov. 9, 2020 in U.S. Appl. No. 13/094,729.
Response to Office Action dated Mar. 15, 2021, filed Jun. 14, 2021 in U.S. Appl. No. 13/094,729.
Response to Office Action dated Aug. 3, 2021, filed on Dec. 2, 2021 in U.S. Appl. No. 13/094,729.
Response to Office Action dated Jan. 18, 2022, filed Jun. 21, 2022 in U.S. Appl. No. 13/094,729.
U.S. Office Action dated Aug. 15, 2022, received in U.S. Appl. No. 13/094,729.
Response to Office Action dated Aug. 15, 2022, filed on Feb. 14, 2023 in U.S. Appl. No. 13/094,729.
Declaration By Troy Bremer in U.S. Appl. No. 13/094,729, dated Feb. 13, 2023.
Response to Office Action dated Oct. 23, 2017, filed Feb. 22, 2018 in U.S. Appl. No. 15/529,966.
U.S. Office Action dated Mar. 16, 2018 in U.S. Appl. No. 15/529,966.
Response to Office Action dated Mar. 16, 2018, filed Aug. 16, 2018 in U.S. Appl. No. 15/529,966.
Response to U.S. Office Action dated Mar. 18, 2019, filed Jun. 28, 2019 in U.S. Appl. No. 15/529,966.

(56) References Cited

OTHER PUBLICATIONS

U.S. Office Action dated Jul. 17, 2019 in U.S. Appl. No. 15/529,966.
Response to U.S. Office Action dated Jul. 17, 2019, filed Oct. 17, 2019 in U.S. Appl. No. 15/529,966.
Response to U.S. Office Action dated Mar. 2, 2020, filed May 29, 2020 in U.S. Appl. No. 15/529,966.
U.S. Office Action dated Jun. 22, 2020 in U.S. Appl. No. 15/529,966.
Response to U.S. Office Action dated Jun. 22, 2020 filed Feb. 3, 2021 in U.S. Appl. No. 15/529,966.
U.S. Notice of Allowance dated Jun. 1, 2021 in U.S. Appl. No. 15/529,966.
Response to U.S. Office Action dated Dec. 7, 2021, filed Feb. 9, 2022 in U.S. Appl. No. 15/529,966.
U.S. Office Action dated Mar. 1, 2022 in U.S. Appl. No. 15/529,966.
Response to U.S. Office Action dated Mar. 1, 2022 filed Aug. 25, 2022 in U.S. Appl. No. 15/529,966.
U.S. Notice of Allowance dated Nov. 2, 2022 in U.S. Appl. No. 15/529,966.
Response to Australian Office Action dated Jul. 25, 2012, filed Mar. 14, 2014 in AU Application No. 2007273055.
Response to Australian Office Action dated Mar. 25, 2014, filed Apr. 9, 2014 in corresponding AU Application No. 2007273055.
Response to Australian Office Action dated Nov. 10, 2014, filed Jul. 19, 2016 in AU Application No. 2013205531.
Australian Office Action dated Nov. 10, 2014 in AU Application No. 2013205536.
Response to Australian Office Action dated Sep. 19, 2013, filed on Jun. 3, 2015 in AU Application No. 2011248632.
Response to Canadian Office Action dated Nov. 20, 2013, filed May 20, 2014 in CA Application No. 2657576.
Response to Canadian Office Action dated Dec. 15, 2014, filed Jun. 10, 2015 in CA Application No. 2,657,576.
Response to Canadian Office Action dated Dec. 9, 2015, filed Jun. 9, 2016 in CA Application No. 2657576.
Response to Canadian Office Action dated Dec. 19, 2016, filed Feb. 24, 2017 in CA Appl. No. 2657576.
Response to Canadian Office Action dated Jun. 21, 2017, filed Dec. 19, 2017 in Canadian Appl. No. 2657576.
Response to Canadian Office Action dated May 31, 2018, filed Nov. 27, 2019 in CA Application No. 2657576.
Response to Canadian Office Action dated Jun. 30, 2020, filed Oct. 30, 2020 in CA Application No. 2657576.
Response to Canadian Office Action dated Jun. 14, 2021, filed Nov. 8, 2021 in CA Application No. 2,657,576.
Canadian Office Action dated May 2, 2022 in CA Application No. 2657576.
Response to Canadian Office Action dated May 2, 2022, filed Sep. 2, 2022 and supplemental Response, filed Sep. 14, 2022 in CA Application No. 2657576.
Response to Canadian Office Action dated Apr. 21, 2017, filed Oct. 20, 2017 in CA Application No. 2797585.
Response to Canadian Office Action dated Dec. 1, 2017, filed Jun. 1, 2018 in CA Application No. 2797585.
Response to Canadian Office Action dated Jun. 7, 2019, filed Dec. 9, 2019 in CA Application No. 2797585.
Response to Canadian Office Action dated May 1, 2020, filed Nov. 2, 2020 in CA Application No. 2797585.
Response to Canadian Office Action dated Apr. 7, 2021, filed Oct. 7, 2021 in CA Application No. 2797585.
Response to European Extended Search Report dated Aug. 5, 2009, filed May 17, 2010 in EP Application No. 07810252.2.
Response to European Office Action dated May 31, 2010, filed Nov. 25, 2010 in EP Application No. 07810252.2.
Response to European Office Action dated Dec. 8, 2010, filed Jun. 14, 2011 in EP Application No. 07810252.2.
Response to European Office Action dated Jul. 18, 2011, filed Jan. 26, 2012 in EP Application No. 07810252.2.
Response to European Office Action dated Aug. 11, 2014, filed May 20, 2015 in EP Application No. 07810252.2.
Response to European Search Report dated Jun. 27, 2012, filed Jan. 24, 2013 in EP Application No. 11188923.4.
Response to Office Action dated Feb. 18, 2013, filed Aug. 26, 2013 in EP Application No. 11188923.4.
Response to European Office Action dated Sep. 20, 2013, filed Jun. 30, 2014 in EP Application No. 11188923.4.
Response to European Office Action dated Jul. 15, 2014, filed Apr. 29, 2015 in EP Application No. 11188923.4.
Response to European Office Action dated May 18, 2015, filed Sep. 18, 2015 in EP Application No. 11188923.4.
Response to European Office Action dated May 12, 2016, filed Nov. 22, 2016 in EP Application No. 11188923.4.
Response to European Office Action dated Jun. 12, 2017, filed Oct. 17, 2017 in EP Application No. 11188923.4.
Response to European Office Action dated Feb. 23, 2018, filed Sep. 4, 2018 in EP Application No. 11188923.4.
Response to European Office Action dated Nov. 29, 2018, filed Apr. 9, 2019 in EP Application No. 11188923.4.
Response to European Office Action dated Sep. 16, 2019, filed Jan. 21, 2020 in EP Application No. 11188923.4.
Response to Extended Search Report dated Mar. 20, 2012, filed Feb. 7, 2013 in EP Application No. 11188925.9.
Response to European Office Action dated Mar. 4, 2013, filed Sep. 13, 2013 in EP Application No. 11188925.9.
Response to European Office Action dated Sep. 26, 2013, filed Jul. 2, 2014 in EP Application No. 11188925.9.
European Search Report dated Mar. 20, 2012 in EP Application No. EP 11 18 8926.7.
Response to Extended Search Report dated Mar. 20, 2012, filed Feb. 7, 2013 in EP Application No. 11188926.7.
Response to European Office Action dated Mar. 4, 2013, filed Sep. 13, 2013 in European Application No. 11188926.7.
Response to European Office Action dated Sep. 26, 2013, filed Jul. 2, 2014 in EP Application No. 11188926.7.
Response to European Search Report dated Jan. 29, 2021, filed on Dec. 10, 2021 in EP Application No. 20190672.4.
European Office Action dated Apr. 13, 2022 in EP Application No. 20190672.4.
Response to European Office Action dated Apr. 13, 2022, filed Jan. 18, 2023 in EP Application No. 20190672.4.
Response to Office Action pursuant to Rules 161(1) and 162 EPC dated Dec. 7, 2012, filed Jun. 5, 2013 in EP Application No. 11721599.6.
Response to European Office Action dated Sep. 30, 2014 and Apr. 15, 2016, filed Aug. 16, 2016 in EP Application No. 11721599.6.
Response to European Office Action dated Mar. 6, 2017, filed Jul. 4, 2017 in EP Application No. 11721599.6.
Response to European Office Action dated Apr. 19, 2018, filed Jun. 18, 2018 in EP Application No. 11721599.6.
European Search Reported dated Mar. 19, 2019 in European Patent Application No. 1820939.5.
Response to European Search Reported dated Mar. 19, 2019 filed on Jan. 9, 2020 in European Patent Application No. 18209239.5.
Response to Office Action dated Jun. 11, 2021, filed Dec. 8, 2021 in EP Application No. 18209239.5.
Response to European Search Report dated May 23, and dated Sep. 21, 2018, filed Apr. 23, 2019 in EP Application No. EP15865163.8.
Response to European Office Action dated Nov. 25, 2019, filed May 28, 2020 in EP Application No. EP15865163.8.
Response to European Office Action dated Dec. 21, 2020, filed Jan. 18, 2021 in EP Application No. EP15865163.8.
Office Action dated Nov. 2, 2022 received in European Patent Application No. EP15865163.8 in 7 pages.
Partial European Search Report dated Jun. 30, 2022 in EP Application No. EP 19859855.9.
Extended European Search Report dated Oct. 20, 2022, received in European Patent Appl. No. 19859855.9.
Response to Japanese Office Action dated Jan. 8, 2013, filed Jul. 5, 2013 in JP Application No. 2009-520751.
Response to Japanese Office Action dated Apr. 8, 2014, filed Jul. 8, 2014 in JP Application No. 2009-520751.
Chen et al., Discordant Protein and mRNA Expression in Lung Adenocarcinomas. Mol Cell Proteo. Apr. 1, 2002;1(4): 304-313.

(56) References Cited

OTHER PUBLICATIONS

Fish et al., Assessment of Treatment for Patients with Primary Ductal Carcinoma in situ in the Breast. Annals Surg Oncol. Dec. 1998;5: 724-732.

Henriksen et al., Semi-quantitative Scoring of Potentially Predictive Markers for Endocrine Treatmentof Breast Cancer: A Comparison Between Whole Sections and Tissue Microarrays. J Clin Path. Apr. 1, 2007;60(4): 397-404.

Mack et al., Relationship of a New Histological Categorization of Ductal Carcinoma in situ of the Breast with Size and the Immunohistochemical Expression of p53, c-erb B2, bcl-2, and ki-67. Human Pathol. Aug. 1, 1997;28(8): 974-979.

Shah et al., The Clinical Utility of DCISionRT® on Radiation Therapy Decision Making in Patients with Ductal Carcinoma in situ Following Breast-conserving Surgery. Annals Surg Oncol. Oct. 1, 2021: 5974-5984.

Response to U.S. Office Action dated May 9, 2023, filed Aug. 9, 2023 in U.S. Appl. No. 15/284,349.

Response to U.S. Office Action dated Apr. 4, 2023, filed Jun. 15, 2023 in U.S. Appl. No. 17/664,006.

U.S. Office Action dated Jun. 15, 2023, received in U.S. Appl. No. 13/094,729.

Japanese Office Action with translation, dated Aug. 22, 2023 in JP Application No. 2021-539476.

U.S. Notice of Allowance dated Sep. 14, 2023 in U.S. Appl. No. 17/664,006, in 10 pages.

\* cited by examiner

METHOD OF SELECTION FOR TREATMENT OF SUBJECTS AT RISK OF INVASIVE BREAST CANCER

RELATED APPLICATIONS

This application is a continuation application of U.S. application Ser. No. 17/275,406, filed Mar. 11, 2021, which is a U.S. national phase application under 35 U.S.C. § 371 of International Application No. PCT/US2019/051128, filed Sep. 13, 2019, which claims priority to U.S. Provisional Application Ser. No. 62/731,316, filed Sep. 14, 2018. The contents of each of these related applications are hereby incorporated by reference in its entirety.

BACKGROUND

Field

The present technology generally relates to whether or not a subject who is at risk of invasive breast cancer will be responsive to various forms of cancer therapy.

Description of the Related Art

There are a variety of markers for the identification of tumors in subjects. In addition, there are various markers that can be used for the prediction of neoplastic progression. For example, U.S. Pat. Pub. Nos. 2010/0003189, 2012/0003639, and 20170350895 disclose a variety of markers that when examined in various combinations can predict the likelihood that a subject will have DCIS and/or invasive breast cancer.

SUMMARY OF VARIOUS EMBODIMENTS

In some embodiments, a method of treating a subject is provided, the method comprises identifying a subject with DCIS that has an elevated level of activity in a k-ras pathway; and administering an aggressive breast cancer therapy to the subject, wherein the aggressive breast cancer therapy is not radiation. In some embodiments, the k-ras pathway is elevated if there is an elevated level of at least one of: K-ras, RAF, MAPK, MEK, ETS or SIAH.

In some embodiments, a method of treating a subject is provided. The method comprises identifying a subject with DCIS, that is HER2 positive and SIAH2 positive; and administering an aggressive breast cancer therapy to the subject.

In some embodiments, a method of identifying a subject who will not be responsive to radiation therapy is provided. The method comprises identifying a subject with DCIS at an elevated risk of invasive breast cancer; and determining if the subject is HER2 (or EGFR) and SIAH2 positive, wherein if the subject is HER2 and SIAH2 positive, administering an aggressive therapy to the subject, wherein the aggressive therapy is not radiation therapy, and wherein the aggressive therapy is selected from the group consisting of: an antibody to HER2 or Trastuzumab.

In some embodiments, a method of identifying a subject for an aggressive cancer therapy is provided. The method comprises identifying a subject with DCIS at an elevated risk of invasive breast cancer; and determining if the subject is HER2 and SIAH2 positive, wherein if the subject is HER2 and SIAH2 positive, administering an aggressive therapy to the subject, wherein the aggressive therapy is not radiation therapy, and wherein the aggressive therapy is selected from the group consisting of: an antibody to HER2 or Trastuzumab.

In some embodiments, a method of determining which method of treatment to recommend to a subject is provided. The method comprises identifying a subject with DCIS at elevated risk of invasive breast cancer; and determining if the subject is HER2 and SIAH2 positive, wherein if the subject is HER2 and SIAH2 positive, recommending an aggressive therapy to the subject, wherein the aggressive therapy is not radiation therapy, and wherein the aggressive therapy is selected from the group consisting of: an antibody to HER2 or Trastuzumab.

In some embodiments, a method for treating a subject is provided. The method comprises providing a DCIS sample from a subject; analyzing the DCIS sample for a level of at least PR, and at least either: a) analyzing the sample for at least HER2 and SIAH2, or b) analyzing the sample for at least FOXA1; and providing a prognosis based upon at least PR, HER2 and SIAH2 or based upon at least PR and FOXA1, wherein if the sample is PR positive, further analyzing the sample for a level of COX2, wherein COX2 positive with at least FOXA1 positive indicates a high risk of invasive breast cancer, determining if the subject is HER2 positive; and administering an aggressive therapy to the subject if the subject is HER2 positive, wherein the aggressive therapy is not radiation therapy, and wherein the aggressive therapy is selected from the group consisting of: an antibody to HER2 or Trastuzumab.

In some embodiments, a method for decreasing a risk of an invasive breast cancer event in a subject is provided. The method comprises providing a DCIS sample from a subject; analyzing the DCIS sample for a level of at least PR, and at least either: analyzing the sample for at least HER2 and SIAH2, or analyzing the sample for at least FOXA1; and providing a prognosis based upon at least PR, HER2 and SIAH2 or based upon at least PR and FOXA1; further analyzing the sample for a level of Ki67, size, or a level of Ki67 and size, if the sample is PR positive and FOXA1 negative; and wherein if the sample is Ki67 positive, a size larger than 5 mm of DCIS, or both, indicates an elevated risk of invasive breast cancer; and administering an aggressive therapy to the subject if the subject is both: HER2 positive, and FOXA1 negative, when Ki67 positive, when a size larger than 5 mm of DCIS, or a combination thereof, wherein the aggressive therapy is not radiation therapy, and wherein the aggressive therapy is selected from the group consisting of: an antibody to HER2, or Trastuzumab.

In some embodiments, a method of providing a benefit of radiation therapy is provided. The method comprises: identifying a subject with DCIS at elevated risk of invasive breast cancer; and administering radiation therapy to the subject if the subject is HER2 negative and not administering radiation therapy to the subject if the subject tis HER2 positive.

In some embodiments, a method for reducing a risk of stage 1A invasive breast cancer event in a subject is provided. The method comprises providing a DCIS sample from a subject; analyzing the DCIS sample for a level of at least PR, and at least either: a) analyzing the sample for at least HER2 and SIAH2, or b) analyzing the sample for at least FOXA1; and providing a prognosis based upon at least PR, HER2 and SIAH2 or based upon at least PR and FOXA1, wherein if the sample is PR positive, further analyzing the sample for a level of COX2, wherein COX2 positive with at least FOXA1 positive indicates a high risk of invasive breast cancer, and wherein if the risk of the invasive breast cancer is high, providing the subject a more aggressive therapy than standard of care.

In some embodiments, a method of determining if insurance will cover the cost of radiation therapy is provided. The method comprises identifying a subject at elevated risk of invasive breast cancer and that has DCIS; determining if the subject is HER2 positive; and not covering a cost of radiation therapy to the subject if the subject is HER2 positive, and covering the cost of radiation therapy to the subject if the subject is HER2 negative.

In some embodiments, a method of providing reimbursement for a radiation therapy is provided. The method comprises identifying a subject that has DCIS and that is further at elevated risk of invasive breast cancer; determining if the subject is HER2 positive and SIAH2 positive; and providing reimbursement of a cost of radiation therapy to the subject if the subject is HER2 negative or SIAH2 negative.

In some embodiments, a method of providing a treatment to a subject who would not otherwise be treated under a current standard of care is provided. The method comprises identifying a subject having DCIS, wherein the subject has an elevated risk of developing invasive breast cancer; and administering to the subject chemotherapy, an antibody to HER2, and/or Trastuzumab to the subject if the subject is HER2+ and SIAH+.

In some embodiments, a method of selecting a therapy for a subject is provided. The method comprises identifying a subject with DCIS at an elevated risk of invasive breast cancer; and determining if the subject is HER2 positive or HER2 negative, wherein if the subject is HER2 positive, administering an aggressive therapy to the subject, wherein the aggressive therapy is not radiation therapy, and wherein the aggressive therapy is selected from the group consisting of: an antibody to HER2 or Trastuzumab; and wherein if the subject is HER2 negative, not administering an aggressive therapy to the subject, thereby reducing that subject's risk of a cardiovascular event.

In some embodiments, a method of treating a subject who will be refractory to radiotherapy is provided. The method comprises identifying a subject with DCIS, that is HER2 positive and SIAH2 positive; and administering to the subject a therapy other than radiotherapy.

BRIEF DESCRIPTION OF THE DRAWINGS

FIG. 3 are IHC assay images depicting some embodiments of a negative (top) and positive (bottom) staining result for SIAH2.

DETAILED DESCRIPTION OF VARIOUS EMBODIMENTS

Figure 1:
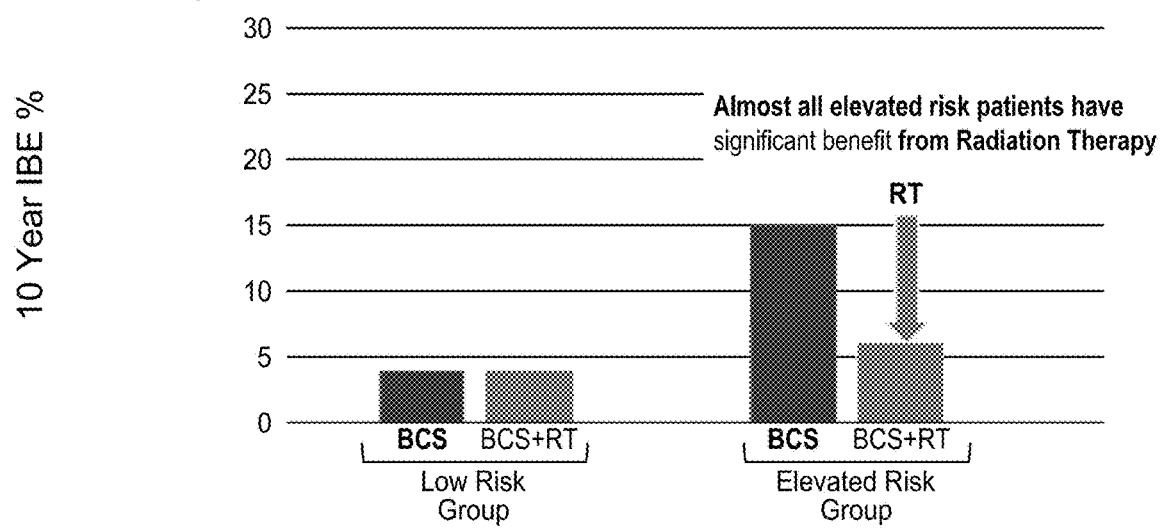
FIG. 1 is a set of graphs depicting that almost all elevated risk patients have a significant benefit from radiation therapy.

While there have been a number of developments in determining the risk that a subject may have in developing ductal carcinoma in situ (DCIS) and/or invasive breast cancer, the analysis often focuses on stratifying various subjects according to risk alone, rather than on how receptive a particular subject may be to a particular treatment. The present disclosure provides a method for taking the state of the art further, and allows one to properly match a particular subject with a particular therapy. In some embodiments, by providing a subject having DCIS, who is also at an elevated risk of invasive breast cancer, one can then test the subject for the subject's receptiveness to radiation therapy via one or more marker(s) provided herein. Thus, one can properly pair subjects at an elevated risk of invasive breast cancer, with a therapy that will work for the subject. This can be especially effective for determining which subjects should receive radiation therapy, as there are a significant number of non-responsive subjects who are in the elevated risk category for invasive breast cancer. Ideally, such subjects should not receive radiation therapy, but instead an alternative form of therapy to prevent and/or reduce the risk of the invasive breast cancer event, such as an anti-HER2 antibody therapy, ERBB therapies, and, for example ERBB1234. The present disclosure provides a brief set of definitions and embodiments, followed by a detailed description of the process and various embodiments around the process, and then concludes with a number of examples.

Definitions and Optional Embodiments

The term "and/or" shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Unless otherwise specified, the definitions provided herein control when the present definitions may be different from other possible definitions.

Unless explained otherwise, all technical and scientific terms used herein have the same meaning as commonly understood to one of ordinary skill in the art to which this disclosure belongs. All HUGO Gene Nomenclature Committee (HGNC) identifiers (IDs) mentioned herein are incorporated by reference in their entirety. Although methods and materials similar or equivalent to those described herein can be used in the practice or testing of the present disclosure, suitable methods and materials are described below. The materials, methods, and examples are illustrative only and not intended to be limiting.

"Antibody" denotes a polypeptide including at least a light chain or heavy chain immunoglobulin variable region which specifically recognizes and binds an epitope of an antigen. In some embodiments, antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. The term antibody includes intact immunoglobulins, as well the variants and portions thereof, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3.sup.rd Ed., W.H. Freeman & Co., New York, 1997. Various antibodies can be used for detecting a marker, including for example, those in the following table, Table 0.1.

TABLE 0.1

ANTIBODIES (FOR DETECTION)

| Antibody to Listed Protein | Antibody Clone (IVD or ASR), Unless Otherwise Noted | Manufacturer(s) |
| --- | --- | --- |
| PGR (PR) | mouse 16 | Leica Biosystems and Biocare Medical |
| PGR (PR) | mouse PgR 636 | Dako and Biocare Medical |
| PGR (PR) | mouse PgR 1294 | Dako |
| PGR (PR) | rabbit SP2 | Thermo Scientific and Biocare Medical |
| PGR (PR) | rabbit SP42 | Cell Marque |
| PGR (PR) | rabbit EP2 | BioGenex |
| PGR (PR) | rabbit 1E2 | Ventana Medical Systems |
| PGR (PR) | mouse PR88 | BioGenex |
| PGR (PR) | rabbit Y85 | Cell Marque |
| ERBB2 (HER2) | rabbit SP3 | Cell Marque, Thermo Scientific, and Diagnostic BioSystems |
| ERBB2 (HER2) | rabbit polyclonal HercepTest/A0485 | Dako |
| ERBB2 (HER2) | mouse CB11 | Leica Biosystems, Cell Marque, and Biocare Medical |
| ERBB2 (HER2) | rabbit EP3 | Cell Marque and BioGenex |
| ERBB2 (HER2) | rabbit 4B5 | Ventana Medical Systems |
| ERBB2 (HER2) | rabbit EP1045Y | Thermo Scientific |
| MKI67 (Ki-67) | mouse MIB-1 | Dako and Biocare Medical |
| MKI67 (Ki-67) | mouse MM1 | Leica Biosystems and Biocare Medical |
| MKI67 (Ki-67) | rabbit SP6 | Cell Marque, Thermo Scientific, Biocare Medical, and Diagnostic BioSystems |
| MKI67 (Ki-67) | mouse K2 | Leica Biosystems |
| MKI67 (Ki-67) | rabbit 30-9 | Ventana Medical Systems |
| MKI67 (Ki-67) | mouse 7B11 | ThermoFisher Scientific |
| MKI67 (Ki-67) | rabbit EPS | BioGenex |
| MKI67 (Ki-67) | mouse BGX-297 | BioGenex |
| MKI67 (Ki-67) | mouse Ki88 | BioGenex |
| PTGS2 (COX-2) | rabbit SP21 | Cell Marque, Ventana Medical Systems, Thermo Scientific, Biocare Medical, and Diagnostic BioSystems |
| PTGS2 (COX-2) | mouse CX-294 | Dako |
| PTGS2 (COX-2) | mouse COX 229 | ThermoFisher Scientific |
| PTGS2 (COX-2) | mouse 4H12 | Diagnostic BioSystems |
| FOXA1 | mouse 2F83 | Cell Marque and Ventana Medical Systems |
| FOXA1 | rabbit SP88 (RUO) | Spring Bioscience and ThermoFisher Scientific |
| FOXA1 | rabbit EP277 (RUO) | Epitomics |
| INK4A (p16) | mouse E6H4 | Ventana Medical Systems |
| INK4A (p16) | mouse G175-405 (RUO) | BioGenex and BD PharminGen |
| INK4A (p16) | mouse JC8 (RUO) | NA |
| INK4A (p16) | mouse 6H12 (RUO) | NA |
| SIAH2 | mouse MRQ-PRE | Cell Marque |
| SIAH2 | mouse 24E6H3 (RUO) | Santa Cruz Biotechnology and Novus Biologicals |

In some embodiments, any of the methods, kits, etc. provided herein that test for a presence or absence of any of the target proteins listed in table 0.1, can employ any one or more of the corresponding antibodies to that target protein.

In some embodiments, each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs."

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

The term "array" denotes an arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called chips or biochips.

The array of molecules makes it possible to carry out a very large number of analyses on a sample at one time. In some embodiments, arrays of one or more molecule (such as an oligonucleotide probe) will occur on the array a plurality of times (such as twice), for instance to provide internal controls. The number of addressable locations on the array can vary, for example from at least one, to at least 2, to at least 5, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect the markers noted herein, such as at least one of those in Tables 1-9, 11 and 13-15 provided herein.

In some embodiments, within an array, each arrayed sample can be addressable, in that its location can be reliably and consistently determined within at least two dimensions of the array. Addressable arrays can be computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to markers provided herein, such as at least one of those in Tables 1-9, 11 and 13-15.

As used herein, the term "gene" means nucleic acid in the genome of a subject capable of being expressed to produce a mRNA and/or protein in addition to intervening intronic sequences and in addition to regulatory regions that control the expression of the gene, e.g., a promoter or fragment thereof.

As used herein, the term "diagnosis", and variants thereof, such as, but not limited to "diagnose" or "diagnosing" shall include, but not be limited to, a primary diagnosis of a clinical state or any primary diagnosis of a clinical state. A diagnostic assay described herein is also useful for assessing the remission of a subject, or monitoring disease recurrence, or tumor recurrence, such as following surgery, radiation therapy, adjuvant therapy or chemotherapy, or determining the appearance of metastases of a primary tumor.

In some embodiments, a prognostic assay described herein is useful for assessing likelihood of treatment benefit, disease recurrence, tumor recurrence, or metastasis of a primary tumor, such as following surgery, radiation therapy, adjuvant therapy or chemotherapy. All such uses of the assays described herein are encompassed by the present disclosure. In some embodiments, the test can be used to predict if the patient will have an occurrence.

The term "breast tumor" denotes a neoplastic condition of breast tissue that can be benign or malignant. The term "tumor" is synonymous with "neoplasm" and "lesion". Exemplary breast tumors include invasive breast cancer, DCIS, lobular carcinoma in situ (LCIS), and atypical ductal hyperplasia (ADH).

The term "cancer" denotes a malignant neoplasm that has undergone characteristic anaplasia with loss of differentiation, increased rate of growth, invasion of surrounding tissue, and is capable of metastasis. The term "cancer" shall be taken to include a disease that is characterized by uncontrolled growth of cells within a subject, such as, but not limited to, invasive breast cancer.

The term "intraductal lesion" refers to tumors that are confined to the interior of the mammary ducts and are, therefore, not invasive breast cancers. Exemplary intraductal lesions include ADH and DCIS.

ADH is a neoplastic intraductal (non-invasive) lesion characterized by proliferation of evenly distributed, monomorphic mammary epithelial cells.

DCIS is a neoplastic intraductal (non-invasive) lesion characterized by increased mammary epithelial proliferation with subtle to marked cellular atypia. DCIS has been divided into grades (low, intermediate, and high) based on factors such as nuclear atypia, intraluminal necrosis, mitotic activity etc. Low-grade DCIS and ADH are morphologically identical, and ADH is distinguished from DCIS based on the extent of the lesion, as determined by its size and/or the number of involved ducts. DCIS is initially typically diagnosed from a tissue biopsy triggered by a suspicious finding (e.g., microcalcifications, unusual mass, tissue distortion or asymmetry, etc.) on a mammogram and/or ultrasound imaging test. It may be from routine screening imaging or, more rarely, from diagnostic imaging triggered by a positive physical examination (e.g., a palpable mass, nipple discharge, skin change, etc.) or by a significant change in a previously identified mass.

Cellular proliferation in DCIS is confined to the milk ducts. If the proliferating cells have invaded through the basement membrane of the myoepithelial cell (MEC) layer lining the duct, thus appearing in the surrounding stroma, then the lesion is considered an invasive breast cancer, even if DCIS is also present. In some cases, the invasion is very minimal (microinvasion) or the only evidence of invasion is disruption of the MEC layer (e.g., by observing discontinuities in MEC-specific protein marker stains such as SMMHC and/or p63). Typically, these microinvasive cases are treated as invasive breast cancers, although there is some controversy in the treatment of these cases.

Recurrence rates in DCIS with current treatments are difficult to estimate. However, it is likely that about 20% of patients who receive lumpectomies without any further treatment would experience recurrence events within 10 years, approximately evenly split between DCIS and invasive events, while <2% of patients who receive mastectomies would experience recurrence. Standard of care with lumpectomy is to receive adjuvant radiation therapy (RT). Several randomized clinical trials provide evidence that adjuvant radiation therapy following lumpectomy reduces recurrence risk by approximately half for both DCIS and invasive event types, and that current clinical and pathologic assessment techniques cannot identify a low-risk sub-group in which there is no benefit from radiation therapy. Radiation is not typically administered after mastectomy. Importantly, although radiation reduces the risk of recurrence events, a survival benefit has not been established with radiation like it has for invasive breast cancer.

LCIS is non-invasive lesion that originates in mammary terminal duct-lobular units generally composed of small and often loosely cohesive cells. When it has spread into the ducts, it can be differentiated from DCIS based on morphology and/or marker stains.

The term "invasive breast cancer" denotes a malignant tumor distinct from, and non-overlapping with, ADH and DCIS, in which the tumor cells have invaded adjacent tissue outside of the mammary duct structures. It can be divided into stages (I, IIA, IIB, IIIA, IIIB, and IV).

Surgery is a treatment for a breast tumor and is frequently involved in diagnosis. The type of surgery depends upon how widespread the tumor is when diagnosed (the tumor stage), as well as the type and grade of tumor. The term "treatment" as provided herein does not require the complete or 100% curing of the subject. Instead, it encompasses the broader concept or delaying the onset of one or more symptoms, extending the life and/or quality of life of the subject, reducing the severity of one or more symptoms, etc.

"Risk" herein is the likelihood for a subject diagnosed with DCIS to have a subsequent ipsilateral breast event after having a first DCIS event. Primary treatment for DCIS can include surgery, radiation, or an adjuvant chemotherapy. In some embodiments, the initial DCIS can be removed. The event can be a DCIS event or an invasive breast cancer event. "Risk of invasive breast cancer", denotes a risk of developing (or being diagnosed with) a subsequent invasive breast cancer in the same (a.k.a. ipsilateral) breast. That is also true for "risk of DCIS" or total risk. In some embodiments, the initial DCIS can be removed.

In some embodiments, surgery as a treatment for DCIS breast tumors and/or preventing or reducing the risk of subsequent ipsilateral invasive breast cancer can include a lumpectomy, mastectomy, and/or bilateral mastectomy.

Adjuvant chemotherapy is often used after surgery to treat any residual disease. Systemic chemotherapy often includes a platinum derivative with a taxane. Adjuvant chemotherapy is also used to treat subjects who have a recurrence or metastasis.

"Adjuvant DCIS treatment" denotes any treatment that is appropriate for a subject that is likely to have a subsequent DCIS event, which can include, less aggressive to more aggressive treatment options depending on the risk profile and perceived patient benefit, from frequent monitoring with planned subsequent lumpectomy upon early detection of a breast event, to lumpectomy without radiation, to an additional lumpectomy, to wide excision. In some embodiments, a subject at risk of DCIS recurrence, but not invasive breast cancer can receive adjuvant DCIS treatment (optionally, in combination with any of the embodiments provided herein).

"Adjuvant invasive breast cancer treatment" denotes any treatment that is appropriate for a subject that is likely to have an invasive breast cancer occurrence, which can include, lumpectomy with radiation, to lumpectomy with a receptor targeted chemotherapy, to lumpectomy with radiation with a receptor targeted chemotherapy, to mastectomy, to mastectomy with a receptor targeted chemotherapy, to mastectomy with radiation, to mastectomy with radiation and a receptor targeted chemotherapy, to surgery with a chemotherapy. In some embodiments, a subject at risk of DCIS recurrence, but not invasive breast cancer can receive adjuvant DCIS treatment (optionally, in combination with any of the embodiments provided herein).

A "marker" refers to a measured biological component such as a protein, mRNA transcript, or a level of DNA amplification. The risk of a subsequent ipsilateral breast event can be predicted through various sets or markers that in combination allow for the prediction of whether or not a subject who has DCIS is likely to experience an ipsilateral DCIS recurrence, a subsequent ipsilateral invasive breast cancer, both, or neither following treatment for DCIS.

The term "control" refers to a sample or standard used for comparison with a sample which is being examined, processed, characterized, analyzed, etc. In some embodiments, the control is a sample obtained from a healthy patient or a non-tumor tissue sample obtained from a patient diagnosed with a breast tumor. In some embodiments, the control is a historical control or standard reference value or range of values (such as a previously tested control sample, such as a group of breast tumor patients with poor prognosis, or group of samples that represent baseline or normal values, such as the level of cancer-associated genes in non-tumor tissue).

The "Cox hazard ratio" is derived from the Cox proportional hazards model. Proportional hazards models are a class of survival models in statistics. Survival models relate the time that passes before some event occurs to one or more covariates that may be associated with that quantity of time. In the Cox proportional hazards model, the unique effect of a unit increase in a covariate is multiplicative with respect to the hazard rate. A "Cox hazard ratio" is the ratio of the hazard rates corresponding to the conditions described by two levels of an explanatory variable—a covariate, that is calculated using the cox proportional hazards model. The cox hazard ratio is the ratio of survival hazards for a one-unit change in the covariate. For example, the Cox hazard ratio may be the ratio of survival hazards for a 1 unit change in the logarithmic gene expression level. Thus, a larger value has a greater effect on survival or the hazard rate of the event being assessed, such as disease recurrence. In some embodiments, a hazard ratio (HR) greater than 1 indicates that an increased covariate level is associated with a worse patient outcome, where the covariate level is a marker expression level. In some embodiments, a HR less than 1 indicates that a decreased covariate level is associated with a better patient outcome, where the covariate level is a marker expression level.

As used herein, the term "non-tumor tissue sample" shall be taken to include any sample from or including a normal or healthy cell or tissue, or a data set produced using information from a normal or healthy cell or tissue. For example, the non-tumor sample may be selected from the group comprising or consisting of: (i) a sample comprising a non-tumor cell; (ii) a sample from a normal tissue; (iii) a sample from a healthy tissue; (iv) an extract of any one of (i) to (iii); (v) a data set comprising measurements of modified chromatin and/or gene expression for a healthy individual or a population of healthy individuals; (vi) a data set comprising measurements of modified chromatin and/or gene expression for a normal individual or a population of normal individuals; and (vii) a data set comprising measurements of the modified chromatin and/or gene expression from the subject being tested wherein the measurements are determined in a matched sample having normal cells. Preferably, the non-tumor sample is (i) or (ii) or (v) or (vii).

As used herein, the term "subject" encompasses any animal including humans, preferably a mammal. Exemplary subjects include but are not limited to humans, primates, livestock (e.g. sheep, cows, horses, donkeys, pigs), companion animals (e.g. dogs, cats), laboratory test animals (e.g.

mice, rabbits, rats, guinea pigs, hamsters), captive wild animals (e.g. fox, deer). Preferably the mammal is a human or primate. More preferably the mammal is a human.

Detecting expression of a gene product denotes determining of a level expression in either a qualitative or quantitative manner can detect nucleic acid molecules or proteins. Exemplary methods include, but are not limited to: microarray analysis, RT-PCR, Northern blot, Western blot, next generation sequencing, and mass spectrometry.

The term "diagnosis" denotes the process of identifying a disease by its signs, symptoms and results of various tests. The conclusion reached through that process is also called "a diagnosis." Forms of testing commonly performed include biopsy for the collection of the DCIS. In some embodiments, a diagnosis includes determining whether a subject with DCIS has a good or poor prognosis. In some embodiments, the prognosis can be a high or low likelihood of a subsequent (within the next 10 years, 15, or 20 years) DCIS event. In some embodiments, the prognosis can be a high or low likelihood of a (within the next 10 years, 15, or 20 years) invasive breast cancer event. In some embodiments, the prognosis can be a high or low likelihood of a subsequent (within the next 10 years) DCIS event and a high or low likelihood of a (within the next 10 years) invasive breast cancer event.

"Differential or alteration in expression" denotes a difference or change, such as an increase or decrease, in the amount of RNA, the conversion of mRNA to a protein, level of protein in the system, or any combination thereof. In some examples, the difference is relative to a control or reference value or range of values, such as an amount of gene expression that is expected in a subject who does not have DCIS and/or an invasive breast cancer or in non-tumor tissue from a subject with a breast tumor. Detecting differential expression can include measuring a change in gene expression or a change in protein levels.

The term "expression" denotes the process by which the coded information of a gene is converted into an operational, non-operational, or structural part of a cell, such as the synthesis of an RNA and/or protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In some embodiments, gene expression can be monitored to determine the diagnosis and/or prognosis of a subject with DCIS, such as to determine or to predict a subject's likelihood to develop a subsequent DCIS or invasive breast cancer. In some embodiments, mRNA expression can be monitored to determine the diagnosis and/or prognosis of a subject with DCIS, such as to determine or to predict a subject's likelihood to develop a subsequent DCIS or invasive breast cancer. In some embodiments, protein expression can be monitored to determine the diagnosis and/or prognosis of a subject with DCIS, such as to determine or to predict a subject's likelihood to develop a subsequent DCIS or invasive breast cancer.

The expression of a nucleic acid molecule in a sample can be altered relative to a control sample, such as a normal or non-tumor sample. Alterations in gene expression, such as differential expression, include but are not limited to: (1) overexpression; (2) underexpression; or (3) suppression of expression. Alterations in the expression of a nucleic acid molecule can be associated with, and in fact cause, a change in expression of the corresponding protein.

In some embodiments, protein expression can also be altered in some manner to be different from the expression of the protein in a normal (e.g., non-DCIS) situation. This includes but is not necessarily limited to: (1) expression of an increased amount of the protein compared to a control or standard amount; (2) expression of a decreased amount of the protein compared to a control or standard amount; (3) alteration of the subcellular localization or targeting of the protein; (4) alteration of the temporally regulated expression of the protein (such that the protein is expressed when it normally would not be, or alternatively is not expressed when it normally would be); (5) alteration in stability of a protein through increased longevity in the time that the protein remains localized in a cell; and (6) alteration of the localized (such as organ or tissue specific or subcellular localization) expression of the protein (such that the protein is not expressed where it would normally be expressed or is expressed where it normally would not be expressed), each compared to a control or standard.

Controls or standards for comparison to a sample, for the determination of differential expression, include samples believed to be normal (in that they are not altered for the desired characteristic, for example a sample from a subject who does not have DCIS or who had DCIS but did not experience any DCIS and/or invasive breast cancer in the 10 years following the DCIS event, as well as laboratory values (e.g., range of values), even though possibly arbitrarily set, keeping in mind that such values can vary from laboratory to laboratory. Laboratory standards and values can be set based on a known or determined population value and can be supplied in the format of a graph or table that permits comparison of measured, experimentally determined values.

As will be appreciated by one of skill in the art, any of the above controls or standards can be provided for any of the methods (such as treatment, analysis, or prognosis) provided herein, and for any of the compositions or methods. These can be positive or negative controls or standards (showing, for example, what a high level or normal level of expression or presence of the molecule is). The controls can be matched for the relevant molecule type as well (e.g., RNA vs. protein). In some embodiments, the control and/or standard can be for COX-2, Ki-67, p16, PR, SIAH2, FOXA1, and/or HER2. In some embodiments, the control and/or standard can be for COX-2, Ki-67, p16, ER, SIAH2, FOXA1, and/or HER2. In some embodiments, any of the PR embodiments provided herein can be replaced with ER as a marker.

The phrase "gene expression profile" (or signature) denotes a differential or altered gene expression that can be detected by changes in the detectable amount of gene expression (such as cDNA, mRNA, or protein) or by changes in the detectable amount of proteins expressed by those genes. A distinct or identifiable pattern of gene expression, for instance a pattern of high and low expression of a defined set of genes or gene-indicative nucleic acids such as ESTs. In some examples, as few as two genes provides a profile, but more genes can be used in a profile, for example, at least 3, 4, 5, 6, or 7 markers (e.g., genes) can be employed to provide a prognosis in regard to risk of subsequent DCIS and/or risk of subsequent invasive breast cancer. Gene expression profiles can include relative as well as absolute expression levels of specific genes, and can be viewed in the context of a test sample compared to a baseline or control sample profile (such as a sample from the same tissue type from a subject who does not have a tumor). In some embodiments, a gene expression profile in a subject is read on an array (such as a nucleic acid or protein array). For example, a gene expression profile can be performed using a commercially available array such as Human Genome GeneChip™ arrays from Affymetrix™ (Santa Clara, Calif.). In some embodiments, any two or more of the markers indicated in any one of Tables 1-9, 11 and 13-15 can be employed as a profile. The term "hybridization" means to form base pairs between complementary regions of two strands of DNA, RNA, or between DNA and RNA, thereby forming a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the sodium concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

The term "isolated" as used in an "isolated" biological component (such as a nucleic acid molecule, protein, or cell) is one that has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. In some embodiments, an isolated cell is a DCIS cell that is substantially separated from other breast cell types, such as non-tumor breast cells.

The term "label" or "probe" denotes an agent capable of detection, for example by ELISA, spectrophotometry, flow cytometry, or microscopy. For example, a label can be attached to a nucleic acid molecule or protein (such as one that can hybridize or bind to any of the markers in any one or more of Tables 1-9, 11 and 13-15), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In some embodiments, a label is conjugated to a binding agent that specifically binds to one or more of the markers disclosed in any one or more of Tables 1-9, 11 and 13-15 to allow for detecting the presence of the marker in a subject or a DCIS sample from the subject.

The term "mammal" includes both human and non-human mammals. Examples of mammals include, but are not limited to: humans, pigs, cows, goats, cats, dogs, rabbits, rats, and mice.

A nucleic acid array is an arrangement of nucleic acids (such as DNA or RNA) in assigned locations on a matrix, such as that found in cDNA arrays, or oligonucleotide arrays.

A "nucleic acid molecules representing genes" is any nucleic acid, for example DNA (intron or exon or both), cDNA, or RNA (such as mRNA), of any length suitable for use as a probe or other indicator molecule, and that is informative about the corresponding gene, such as those listed in Tables 1-9, 11 and 13-15.

"Polymerase chain reaction" (PCR) is an in vitro amplification technique that increases the number of copies of a nucleic acid molecule (for example, a nucleic acid molecule in a sample or specimen), such as amplification of a nucleic acid molecule listed in Tables 1-9, 11 and 13-15. The product of a PCR can be characterized by standard techniques known in the art, such as electrophoresis, restriction endonuclease cleavage patterns, oligonucleotide hybridization or ligation, and/or nucleic acid sequencing. In some examples, PCR utilizes primers, for example, DNA oligonucleotides 10-100 nucleotides in length, such as about 15, 20, 25, 30 or 50 nucleotides or more in length (such as primers that can be annealed to a complementary target DNA strand by nucleic acid hybridization to form a hybrid between the primer and the target DNA strand, such as those listed in Tables 1-9, 11 and 13-15). Primers can be selected that include at least 15, at least 20, at least 25, at least 30, at least 35, at least 40, at least 45, at least 50 or more consecutive nucleotides of a marker provided herein. Methods for preparing and using nucleic acid primers are described, for example, in Sambrook et al. (In Molecular Cloning: A Laboratory Manual, CSHL, New York, 1989), Ausubel et al. (ed.) (In Current Protocols in Molecular Biology, John Wiley & Sons, New York, 1998), and Innis et al. (PCR Protocols, A Guide to Methods and Applications, Academic Press, Inc., San Diego, Calif., 1990).

The term "prognosis" denotes a prediction of the course of a disease. In some embodiments provided herein, the phrase, when used in the context of a person already having DCIS, denotes the likelihood that a subject having the DCIS will go on (within a following ten, fifteen, or twenty year period) to have a subsequent a) ipsilateral DCIS event after surgical removal of the primary DCIS, b) ipsilateral invasive breast cancer, c) both events, or d) neither a) nor b). The prediction can include determining a) the likelihood of an ipsilateral breast event, b) the likelihood of an ipsilateral breast event in a particular amount of time (e.g., 1, 2, 3 or 5 years), c) the likelihood that a particular therapy (e.g., radiation) will prevent an ipsilateral breast event, d) an optimal treatment to help prevent an ipsilateral event that matches the severity of the most likely event, or e) combinations thereof.

The phrase "specific binding agent" denotes an agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of the disclosed markers (such as those listed in Tables 1-9, 11 and 13-15). In some embodiments, the specific binding agent is capable of binding to a downstream factor regulated by at least one of the disclosed markers (such as those listed in Tables 1-9, 11 and 13-15). Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A "protein-specific binding agent" binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Cyclooxygenase-2 ("prostaglandin-endoperoxide synthase 2," "PTGS2," and "COX-2"; HGNC:9605), referenced herein as COX-2, is an enzyme that is encoded by the PTGS2 gene. Unless denoted otherwise, the term can encompass DNA, RNA, and/or protein versions. Thus, a level of the indicated marker can denote, for example, RNA levels or protein levels. The use of the generic term herein (such as a "level of COX-2"), denotes all of the above options together and individually (e.g., COX-2 protein level and COX-2 RNA level, or COX-2 protein level, or COX-2 RNA level).

Marker of proliferation Ki-67 ("MKI67" and "MIB-1"; HGNC:7107), referenced herein as Ki-67, is a protein that is encoded by the MKI67 gene. Unless denoted otherwise, the term can encompass DNA, RNA, and/or protein versions. Thus, a level of the indicated marker can denote, for example, RNA levels or protein levels. The use of the generic term herein (such as a "level of p16"), denotes all of the above options together and individually (e.g., Ki-67 protein level and Ki-67 RNA level, or Ki-67 protein level, or Ki-67 RNA level).

p16 isoform of cyclin-dependent kinase inhibitor 2A ("cyclin-dependent kinase inhibitor 2A," "p16/INK4A," "CDKN2A," and "MTS1"; HGNC:1787), referenced herein as "p16", is a tumor suppressor protein that is encoded by the CDKN2A gene. Unless denoted otherwise, the term can encompass DNA, RNA, and/or protein versions. Thus, a level of the indicated marker can denote, for example, RNA levels or protein levels. The use of the generic term herein (such as a "level of p16"), denotes all of the above options together and individually (e.g., p16 protein level and p16 RNA level, or p16 protein level, or p16 RNA level).

Progesterone receptor ("NR3C3," "PR," and "PGR"; HGNC:8910), referenced herein as "PR", is a protein that is encoded by the PGR gene. Unless denoted otherwise, the term can encompass DNA, RNA, and/or protein versions. Thus, a level of the indicated marker can denote, for example, RNA levels or protein levels. The use of the generic term herein (such as a "level of PR"), denotes all of the above options together and individually (e.g., PR protein level and PR RNA level, or PR protein level, or PR RNA level).

Estrogen receptor 1 ("ESR1," "ER," "ESR," "Era," "ESRA," "ESTRR," and "NR3A1"; HGNC:3467), referenced herein as "ER", is a protein that is encoded by the ESR1 gene. Unless denoted otherwise, the term can encompass DNA, RNA, and/or protein versions. Thus, a level of the indicated marker can denote, for example, RNA levels or protein levels. The use of the generic term herein (such as a "level of ER"), denotes all of the above options together and individually (e.g., ER protein level and ER RNA level, or ER protein level, or ER RNA level).

SIAH2 E3 ubiquitin protein ligase 2 ("SIAH2" and "seven in absentia [*Drosophila*] homolog 2"; HGNC: 10858), referenced herein as SIAH2, is an enzyme that is encoded by the SIAH2 gene. Unless denoted otherwise, the term can encompass DNA, RNA, and/or protein versions. Thus, a level of the indicated marker can denote, for example, RNA levels or protein levels. The use of the generic term herein (such as a "level" of SIAH2"), denotes all of the above options together and individually (e.g., SIAH2 protein level and SIAH2 RNA level, or SIAH2 protein level, or SIAH2 RNA level).

forkhead box A1 ("FOXA1"; HGNC:5021), referenced herein as FOXA1, is a protein that is encoded by the FOXA1 gene. Unless denoted otherwise, the term can encompass DNA, RNA, and/or protein versions. Thus, a level of the indicated marker can denote, for example, RNA levels or protein levels. The use of the generic term herein (such as a "level of FOXA1"), denotes all of the above options together and individually (e.g., FOXA1 protein level and FOXA1 RNA level, or FOXA1 protein level, or FOXA1 RNA level).

v-erb-b2 avian erythroblastic leukemia viral oncogene homolog 2" ("ERBB2," "HER2" [human epidermal growth factor receptor 2], "NEU", and "CD340"; HGNC:3430), referenced herein as "HER2", is a protein that is encoded by the ERBB2 gene. Unless denoted otherwise, the term can encompass DNA, RNA, and/or protein versions. Thus, a level of the indicated marker can denote, for example, RNA levels or protein levels. The use of the generic term herein (such as a "level of HER2"), denotes all of the above options together and individually (e.g., HER2 protein level and HER2 RNA level, or HER2 protein level, or HER2 RNA level).

A subject having "post menopausal" status can be identified by menstrual cessation (if known) or by age (if menstrual status not known) for example, greater than 50, such as greater than 55.

The term "radiation therapy" denotes a therapy that involves or includes some form of radiation in an amount that is therapeutic to the subject.

The term "non-radiation therapy" denotes a therapy that is adequate for addressing or reducing the risk of invasive breast cancer in a subject, and that does not derive its therapeutic effect by radiation. Examples of such therapy include, chemo therapeutics, targeted and non targeted, immune and non-immune modulated, monoclonal, other targeted and non-targeted, genomic therapies, antibody therapeutics, including, HER2 antibodies, including Trastuzumab. Often, in the present application, "non-radiation therapy" is denoted as "other therapy".

The term "aggressive" as used herein denotes that treatment is appropriate for a subject who is at a high risk of developing the denoted event. Thus, an aggressive breast cancer therapy is a therapy for a subject who, it is understood, will most likely develop breast cancer. Such therapies are generally more extensive in nature than other therapies. Examples of such therapies include: aggressive radiation therapy, and aggressive non-radiation therapy.

General Description of Various Embodiments

Provided herein are methods for identifying and treating various subjects with an appropriate form of therapy, both for the risk to the subject and for the likelihood that the subject will be responsive to the therapy. It has been appreciated that not all subjects, even those at elevated risk of invasive breast cancer, will respond to various forms of therapy, and radiation therapy in particular. Thus, various embodiments provided herein allow one to determine if the subject at elevated risk of invasive breast cancer should receive radiation therapy or some other therapy instead.

In some embodiments, a method of treating a subject is provided. The method comprises identifying a subject with DCIS. The subject also has an elevated level of activity in a k-ras pathway. The subject is then treated with (or receives) an aggressive breast cancer therapy. In some embodiments, the k-ras pathway is elevated if there is an elevated level of at least one of: K-ras, RAF, MAPK, MEK, ETS or SIAH2. In some embodiments, elevated denotes at least 10% or more of an increase in the protein or RNA levels of one or more of K-ras, RAF, MAPK, MEK, ETS or SIAH2. In some embodiments, it is at least 20, 30, 40, 50, 60, 70, 80, 90, 100, 200, 300, 400, 500% or more than the level in a subject who is not at elevated risk of developing invasive breast cancer. In some embodiments, the subject is further treated with a non-radiation, aggressive, therapy, if there is an elevated level of at least one of the following: K-ras, RAF, MAPK, MEK, ETS or SIAH. In some embodiments, the subject also has DCIS. In some embodiments, the subject has DCIS, is HER2 positive and has elevated levels in 2, 3, 4, 5, or all 6 of: K-ras, RAF, MAPK, MEK, ETS, and SIAH. In some embodiments, the subject has DCIS and is HER2 positive and has elevated levels in 1, 2, 3, 4, 5, or all 6 of: K-ras, RAF, MAPK, MEK, ETS, and SIAH2, and is then treated with a non-radiation therapy, for example a HER2 antibody, such as trastuzumab.

In some embodiments, a method of treating a subject is provided. The method comprises identifying a subject with DCIS, that is HER2 positive and SIAH2 positive and administering an aggressive breast cancer therapy to the subject. In some embodiments, the treatment is not a radiation therapy. In some embodiments, the aggressive breast cancer therapy is chemotherapy, such as a Her2 Ab, such as trastuzumab.

In some embodiments, a method of identifying a subject who will not be responsive to radiation therapy is provided. The method comprises: identifying a subject with DCIS at an elevated risk of invasive breast cancer, and determining if the subject is HER2 (or EGFR) and SIAH2 positive. If the subject is HER2 and SIAH2 positive, one then administers an aggressive therapy to the subject (or if one is the patient, one receives the aggressive therapy). The aggressive therapy is not radiation therapy, and can be selected from one or more of the group consisting of: an antibody to HER2 or Trastuzumab.

In some embodiments, a method of identifying a subject for an aggressive cancer therapy is provided. The method comprises identifying a subject with DCIS at an elevated risk of invasive breast cancer and determining if the subject is HER2 and SIAH2 positive. In some embodiments, if the subject is HER2 and SIAH2 positive, one administers (or instructs the administration of) an aggressive therapy to the subject. The aggressive therapy is not radiation therapy. In some embodiments, the aggressive therapy is selected from one or more of the group consisting of: an antibody to HER2, Trastuzumab, cytotoxic drugs, and ERBB2 directed compounds (such as antibodies to ERBB2).

In some embodiments, a method for treating a subject is provided. The method comprises providing a DCIS sample from a subject, analyzing the DCIS sample for a level of at least PR, and at least either: a) analyzing the sample for at least HER2 and SIAH2, or b) analyzing the sample for at least FOXA1, and providing a prognosis based upon at least PR, HER2 and SIAH2 or based upon at least PR and FOXA1. If the sample is PR positive, further analyzing the sample for a level of COX2, wherein COX2 positive with at least FOXA1 positive indicates a high risk of invasive breast cancer. The method further comprises determining if the subject is HER2 positive, and administering an aggressive therapy to the subject if the subject is HER2 positive. The aggressive therapy is not radiation therapy. In some embodiments, the aggressive therapy is selected from one or more of the group consisting of: an antibody to HER2 and Trastuzumab.

In some embodiments, a method for decreasing a risk of an invasive breast cancer event in a subject is provided. The method comprises providing a DCIS sample from a subject, analyzing the DCIS sample for a level of at least PR, and at least either: a) analyzing the sample for at least HER2 and SIAH2, or b) analyzing the sample for at least FOXA1; and then providing a prognosis based upon at least PR, HER2 and SIAH2 or based upon at least PR and FOXA1. One then further analyzes the sample for a level of Ki67, size, or a level of Ki67 and size, if the sample is PR positive and FOXA1 negative. If the sample is Ki67 positive, a size larger than 5 mm of DCIS, or both, it indicates an elevated risk of invasive breast cancer. The method further comprises administering an aggressive therapy to the subject if the subject is both: a) HER2 positive, and b) FOXA1 negative, when Ki67 positive, when a size larger than 5 mm of DCIS, or a combination thereof. The aggressive therapy is not radiation therapy. In some embodiments, the aggressive therapy is selected from one or more of the group consisting of: an antibody to HER2 and Trastuzumab.

In some embodiments, a method of providing a benefit of radiation therapy to a subject is provided. The method comprises identifying a subject with DCIS at elevated risk of invasive breast cancer and administering radiation therapy to the subject if the subject is HER2 negative. In some embodiments, one does not administer radiation therapy to the subject if the subject tis HER2 positive.

In some embodiments, a method of determining which method of treatment to recommend to a subject is provided. The method comprises identifying a subject with DCIS at elevated risk of invasive breast cancer and determining if the subject is HER2 and SIAH2 positive. If the subject is HER2 and SIAH2 positive, one recommends an aggressive therapy to the subject, wherein the aggressive therapy is not radiation therapy. In some embodiments, the aggressive therapy for breast cancer is selected from the group consisting of: an antibody to HER2 or Trastuzumab or any of the other options noted herein. If the subject is HER2 or SIAH2 negative, and still at elevated risk of invasive breast cancer, one recommends radiation therapy.

In some embodiments, recommending is done by a physician to the subject. In some embodiments, this is done separately, following an analysis of the markers, by a healthcare provider or via an insurance company. In some embodiments, the recommending process is provided via the selection and/or administration of the particular therapy to the subject. In some embodiments, the recommending process is done via the approval of reimbursement and/or payment of a non-radiation therapy for the subject.

In some embodiments, a method of selecting a therapy for a subject is provided. The method comprises identifying a subject with DCIS at an elevated risk of invasive breast cancer and determining if the subject is HER2 positive or HER2 negative. If the subject is HER2 positive, one can then administer an aggressive therapy to the subject. In some embodiments, the aggressive therapy is not radiation therapy. In some embodiments, the aggressive therapy is selected from the group consisting of at least one of: an antibody to HER2 or Trastuzumab or other options disclosed herein. If the subject is HER2 negative, one does not administer an aggressive therapy to the subject. This combination allows one to reduce that subject's risk of a cardiovascular event, while retaining a benefit of treatment for those in need and that will benefit from the particular therapy.

In some embodiments, a method of providing a treatment to a subject who would not otherwise be treated under a current (2018, in the United States) standard of care is provided. The method comprises identifying a subject having DCIS. The subject also has an elevated risk of developing invasive breast cancer. The method further comprises administering to the subject chemotherapy. The chemotherapy can include, for example, an antibody to HER2, and/or Trastuzumab. This is done if the subject is HER2+ and SIAH+.

In some embodiments, a method of treating a subject who will be refractory to radiotherapy is provided. The method comprises identifying a subject that has DCIS, that is HER2 positive and SIAH2 positive and administering to the subject a therapy other than radiotherapy. In some embodiments, the therapy other than radiotherapy is an antibody to HER2 and/or trastuzumab and/or cytotoxic drugs, and ERBB2 directed compounds (such as antibodies to ERBB2).

In some embodiments, a method for reducing a risk of a stage 1A invasive breast cancer event in a subject is provided. The method comprises providing a DCIS sample from a subject, analyzing the DCIS sample for a level of at least PR, and at least either: a) analyzing the sample for at least HER2 and SIAH2, or b) analyzing the sample for at least FOXA1. The method further comprises providing a prognosis based upon at least PR, HER2 and SIAH2 or based upon at least PR and FOXA1. If the sample is PR positive, further analyzing the sample for a level of COX2. If the sample is COX2 positive with at least FOXA1 positive, it indicates a high risk of invasive breast cancer. If the risk of the invasive breast cancer is high, providing the subject a more aggressive therapy than the standard of care for treating DCIS as of 2018 in the United States (e.g., 1A DCIS only).

In some embodiments, a method of determining if insurance will cover the cost of radiation therapy is provided. The method comprises identifying a subject at elevated risk of invasive breast cancer and that has DCIS, determining if the subject is HER2 positive, and not covering a cost of radiation therapy to the subject if the subject is HER2 positive, and covering the cost of radiation therapy to the subject if the subject is HER2 negative.

In some embodiments, a method of determining if insurance will cover the cost of radiation therapy is provided. The method comprises identifying a subject at elevated risk of invasive breast cancer and that has DCIS, determining if the subject is HER2 positive and SIAH2 positive, and not covering a cost of radiation therapy to the subject if the subject is HER2 positive and SIAH2 positive, and covering the cost of radiation therapy to the subject if the subject is HER2 negative and/or SIAH2 negative.

In some embodiments, a method of paying for radiation therapy is provided. The method comprises identifying a subject at elevated risk of invasive breast cancer and that has DCIS, determining if the subject is HER2 positive, and not paying for radiation therapy for the subject if the subject is HER2 positive, and paying (at least in part) for radiation therapy for the subject if the subject is HER2 negative.

In some embodiments, a method of paying for radiation therapy is provided. The method comprises identifying a subject at elevated risk of invasive breast cancer and that has DCIS, determining if the subject is HER2 positive and SIAH2 positive, and not paying for radiation therapy for the subject if the subject is HER2 positive and SIAH2 positive, and paying (at least in part) for radiation therapy for the subject if the subject is HER2 negative and/or SIAH2 negative.

In some embodiments, a method of providing reimbursement for a radiation therapy is provided. The method comprises identifying a subject that has DCIS and that is further at elevated risk of invasive breast cancer, determining if the subject is HER2 positive and SIAH2 positive, and providing reimbursement of a cost of radiation therapy to the subject if the subject is HER2 negative or SIAH2 negative.

In some embodiments, a method of providing reimbursement for non-radiation therapy is provided. The method comprises identifying a subject that has DCIS and that is further at elevated risk of invasive breast cancer, determining if the subject is HER2 positive and SIAH2 positive, and providing reimbursement of a cost of non-radiation therapy to the subject if the subject is HER2 positive and SIAH2 positive.

In some embodiments, the aggressive therapy employed herein is a therapy that is appropriate for a subject who is at an elevated risk of developing invasive breast cancer, and the therapy is adequate to address and meaningfully reduce the risk of invasive breast cancer. In some embodiments, the therapy is a chemotherapy. In some embodiments, the chemotherapy is selected from the group consisting of: an antibody to HER2 and/or trastuzumab and/or cytotoxic drugs, and ERBB2 directed compounds (such as antibodies to ERBB2). In some embodiments, the therapy is a therapy that comprises an anti-HER2 antibody, such as, for example: trastuzumab. In some embodiments, the therapy comprises trastuzumab.

In some embodiments, the analysis of each marker is carried out in parallel with each other. In some embodiments, the analysis of each marker is carried out at overlapping times. In some embodiments, PR analysis occurs first and any further analysis depends upon the result of the PR analysis. In some embodiments, no additional markers are looked at to determine the particular therapy to administer. In some embodiments, the HER2 and/or SIAH2 analysis is done first. In some embodiments, the sample and/or subject is first identified as having DCIS, and only after that, is it determined if they have an elevated risk of invasive cancer, and only after that, is it determined if they will be refractory to radiation therapy (i.e., HER2+ and SIAH+).

In some embodiments, additional factors that can be reviewed to determine the appropriate therapy are those that indicate an elevation in the K-ras pathway. Subjects with elevated levels can be identified as refractory for radiation therapy (if they also have DCIS).

Exemplary Embodiments Regarding "Elevated Risk" Subjects and the Identification Thereof Provided below are exemplary embodiments for identifying subjects at elevated risk of developing invasive breast cancer. While this is not exhaustive, it is representative of how those of skill in the art can identify such individuals. In some embodiments, any of the methods provided herein for identifying a subject at "elevated risk," or "high risk" or that should receive a therapy that is "aggressive" indicates that the subject is at elevated risk of invasive breast cancer and would benefit from the arrangement provided herein regarding subjects with DCIS and the decision of whether they are refractory to radiation therapy or not. Thus, any of the embodiments provided herein (regarding treatment, identification, etc. of subjects at risk of invasive breast cancer, can be used in the embodiments to determine which therapy to administer to the subject. In some embodiments, any subject that is identified as having an elevated risk can also be screened for if they will be responsive to radiation therapy or should instead receive a non-radiation therapy (such as a HER2 antibody). For the prognosis listed in the tables below, only those that indicate an "invasive risk" are relevant for the process provided herein, and only in those that already have DCIS. In some embodiments, other categories of subjects indicate those subjects who would not benefit from the radiation refractory analysis provided herein. Thus, the disclosure provides guidance as to who would, and who would not, benefit from the present analysis. That is, once the elevated risk is established, then further examining the sample to determine the appropriate treatment for the subject, by the options noted herein (e.g., examining HER2 and SIAH2).

| Row | Comment | Prognosis | Pop. Evaluation of Risk Factors w/in the population subset indicated | Higher Risk factors | Lower Risk factors | Hazard Ratio (95% Confid. Interval) | P-value | n # of Patients | Significance |
|---|---|---|---|---|---|---|---|---|---|
| | | | TABLE 1 | | | | | | |
| 1 | PR− is an invasive risk factor in patients younger than 50 | Invasive risk | Age < 50 | PR− | PR+ | 6.0 (2.0-18.1) | 0.00028 | 168 | Strong |
| 2 | The combination of PR− and Age < 50 is an invasive risk factor | Invasive risk | Total | PR− & Age < 50 | PR+ or Age ≥ 50 | 4.1 (2.2-7.4) | 0.000036 | 603 | Strong |
| 3 | Age alone is a low-moderate risk factor for invasive risk | Insufficient for invasive prognosis | Total | Age < 50 | Age ≥ 50 | 1.8 (1.0-3.3) | 0.042 | 603 | Weak |
| 4 | PR status alone is not sufficient to predict invasive risk | Insufficient for invasive prognosis | Total | PR− | PR+ | 1.6 (0.9-2.9) | 0.11 | 603 | None |
| | | | TABLE 2 | | | | | | |
| 1 | Elevated SIAH2 is a DCIS risk factor in HER2+ patients | DCIS risk | Total | HER2+ & SIAH2 ≥ 30 | HER2− & SIAH2 < 30 | 2.8 (1.3-6.1) | 0.015 | 461 | Significant |
| 2 | Elevated SIAH2 is a DCIS risk factor in HER2+ patients | DCIS risk | Total | HER2+ & SIAH2 ≥ 20 | HER2− & SIAH2 < 20 | 2.2 (1.1-4.6) | 0.04 | 461 | Weak |
| 3 | HER2 status alone is not sufficient to predict risk | Insufficient for DCIS prognosis | Total | HER2+ | HER2− | 1.8 (0.9-3.7) | 0.099 | 461 | None |
| 4 | Elevated SIAH2 alone is not sufficient to predict DCIS risk | Insufficient for DCIS prognosis | Total | SIAH2 ≥ 30 | SIAH2 < 30 | 1.9 (1.0-3.9) | 0.062 | 461 | None |
| | | | TABLE 3 | | | | | | |
| 1 | Elevated SIAH2 is a DCIS risk factor in PR− patients | DCIS risk | PR− | SIAH2 ≥ 30; PR− | SIAH2 < 30; PR− | 4.1 (1.3-13.1) | 0.011 | 196 | Strong |
| 2 | Elevated SIAH2 is a DCIS risk factor in PR− patients | DCIS risk | PR− | SIAH2 ≥ 20; PR− | SIAH2 < 20; PR− | 9.2 (1.2-70.2) | 0.0037 | 196 | Strong |
| 3 | PR status alone is not sufficient to predict DCIS risk | Insufficient for DCIS prognosis | Total | PR− | PR+ | 1.0 (0.5-2.0) | 0.94 | 461 | None |
| 4 | Elevated SIAH2 alone is not sufficient to predict DCIS risk | Insufficient for DCIS prognosis | Total | SIAH2 ≥ 20 | SIAH2 < 20 | 1.6 (0.8-3.2) | 0.18 | 461 | None |
| | | | TABLE 4 | | | | | | |
| 1 | Elevated SIAH2 is a DCIS risk factor in PR− or HER2+ patients | DCIS risk | PR− or HER2+ | SIAH2 ≥ 30; (PR− or HER2+) | SIAH2 < 30; (PR− or HER2+) | 3.5 (1.0-12.1) | 0.026 | 220 | Significant |
| 2 | Elevated SIAH2 is a DCIS risk factor in PR− or HER2+ patients | DCIS risk | PR− or HER2+ | SIAH2 ≥ 20; (PR− or HER2+) | SIAH2 < 20; (PR− or HER2+) | 3.3 (1.2-8.9) | 0.013 | 220 | Significant |

| Row | Comment | Prognosis | Pop. Evaluation of Risk Factors w/in the population subset indicated | Higher Risk factors | Lower Risk factors | Hazard Ratio (95% Confid. Interval) | P-value | n # of Patients | Significance |
|---|---|---|---|---|---|---|---|---|---|
| 3 | PR− or HER2+ alone is not sufficient to predict DCIS risk | Insufficient for DCIS prognosis | Total | PR− or HER2+ | PR+ and HER2− | 1.3 (0.6-2.5) | 0.49 | 457 | None |

TABLE 5

| Row | Comment | Prognosis | Pop. Evaluation of Risk Factors w/in the population subset indicated | Higher Risk factors | Lower Risk factors | Hazard Ratio (95% Confid. Interval) | P-value | n # of Patients | Significance |
|---|---|---|---|---|---|---|---|---|---|
| 1 | Elevated SIAH2 is a DCIS risk factor in patients older than 55 | DCIS risk | Age > 55 | SIAH2 ≥ 30; AGE > 55 | SIAH2 < 30; AGE > 55 | 4.4 (1.8-11.0) | 0.0014 | 258 | Strong |
| 2 | Elevated SIAH2 is a DCIS risk factor in patients older than 55 | DCIS risk | Age > 55 | SIAH2 ≥ 40; AGE > 55 | SIAH2 < 40; AGE > 55 | 4.0 (1.6-9.9) | 0.0054 | 258 | Strong |
| 3 | Age alone not sufficient to predict DCIS risk | Insufficient for DCIS prognosis | Total | Age > 55 | Age ≤ 55 | 1.1 (0.5-2.1) | 0.85 | 461 | None |
| 4 | Elevated SIAH2 alone is not sufficient to predict DCIS risk | Insufficient for DCIS prognosis | Total | SIAH2 ≥ 30 | SIAH2 < 30 | 1.9 (1.0-3.9) | 0.063 | 461 | None |
| 5 | Elevated SIAH2 alone is not sufficient to predict DCIS risk | Insufficient for DCIS prognosis | Total | SIAH2 ≥ 20 | SIAH2 < 20 | 1.6 (0.8-3.2) | 0.18 | 461 | None |
| 6 | Elevated SIAH2 alone is not sufficient to predict DCIS risk | Insufficient for DCIS prognosis | Total | SIAH2 ≥ 40 | SIAH2 < 40 | 1.9 (0.9-4.0) | 0.10 | 461 | None |

TABLE 6

| Row | Comment | Prognosis | Pop. Evaluation of Risk Factors w/in the population subset indicated | Higher Risk factors | Lower Risk factors | Hazard Ratio (95% Confid. Interval) | P-value | n # of Patients | Significance |
|---|---|---|---|---|---|---|---|---|---|
| 1 | Low FOXA1 is a DCIS risk factor within PR+ patients | DCIS risk | PR+ | FOXA1 ≤ 150; PR+ | FOXA1 > 150; PR+ | 2.2 (1.0-4.8) | 0.049 | 301 | Weak |
| 2 | Low FOXA1 is a DCIS risk factor within PR− patients | DCIS risk | PR+ | FOXA1 ≤ 100; PR+ | FOXA1 > 100; PR+ | 2.7 (1.2-5.8) | 0.018 | 301 | Significant |
| 3 | PR status alone is not sufficient to predict DCIS risk | Insufficient for DCIS prognosis | Total | PR+ | PR− | 1.1 (0.6-2.1) | 0.68 | 518 | None |
| 4 | Low FOXA1 alone is not sufficient to predict DCIS risk | Insufficient for DCIS prognosis | Total | FOXA1 ≤ 100 | FOXA1 > 100 | 1.6 (0.8-2.9) | 0.16 | 518 | None |
| 5 | Low FOXA1 alone is not sufficient to predict DCIS risk | Insufficient for DCIS prognosis | Total | FOXA1 ≤ 150 | FOXA1 > 150 | 1.5 (0.8-2.8) | 0.18 | 518 | None |

TABLE 7

| Row | Comment | Prognosis | Pop. Evaluation of Risk Factors w/in the population subset indicated | Higher Risk factors | Lower Risk factors | Hazard Ratio (95% Confid. Interval) | P-value | n # of Patients | Significance |
|---|---|---|---|---|---|---|---|---|---|
| 1 | Low FOXA1 defined as ≤150 is a DCIS risk factor in PR+ patients younger than 60 | DCIS risk | PR+ & Age < 60 | FOXA1 ≤ 150; PR+ and AGE < 60 | FOXA1 > 150; PR+ and AGE < 60 | 3.6 (1.4-9.6) | 0.0091 | 175 | Strong |
| 2 | Low FOXA1 defined as ≤150 is a DCIS risk factor in PR+ patients younger than 60 | DCIS risk | PR+ & Age < 60 | FOXA1 ≤ 100; PR+ and AGE < 60 | FOXA1 > 100; PR+ and AGE < 60 | 3.9 (1.5-10.2) | 0.0064 | 175 | Strong |
| 3 | Low FOXA1 status defined as ≤100 is not sufficient to predict DCIS risk in patients younger than 60 | Insufficient for DCIS prognosis | Age < 60 | FOXA1 ≤ 100; AGE < 60 | FOXA1 > 100; AGE < 60 | 2.1 (1.0-4.4) | 0.065 | 300 | None |
| 4 | PR status alone is not sufficient to predict DCIS risk in patients younger than 60 | Insufficient for DCIS prognosis | Age < 60 | PR+; AGE < 60 | PR+; AGE < 60 | 1.2 (0.6-2.7) | 0.62 | 300 | None |

| Row | Comment | Prognosis | Pop. Evaluation of Risk Factors w/in the population subset indicated | Higher Risk factors | Lower Risk factors | Hazard Ratio (95% Confid. Interval) | P-value | n # of Patients | Significance |
|---|---|---|---|---|---|---|---|---|---|
| TABLE 8 | | | | | | | | | |
| 1 | Elevated SIAH2 defined as ≥30 is a DCIS risk factor in PR− patients with elevated FOXA1 defined as >100 | DCIS risk | PR− & FOXA1 > 100 | SIAH2 ≥ 30; PR− & FOXA1 > 100 | SIAH2 < 30; PR− & FOXA1 > 100 | 6.5 (1.4–30.6) | 0.0069 | 122 | Strong |
| 2 | The combination of PR− and elevated SIAH2 defined as ≥30 is a DCIS risk factor in the elevated FOXA1 category | DCIS risk | FOXA1 > 100 | PR− & SIAH2 ≥ 30; FOXA1 > 100 | (PR+ or SIAH2 < 30); FOXA1 > 100 | 3.9 (1.6–9.6) | 0.0055 | 328 | Strong |
| TABLE 9 | | | | | | | | | |
| 1 | Combined SIAH2, FOXA1 PR HER2 and KI67 and margin status form a significant risk prognosis for DCIS | DCIS risk | TOTAL | (FOXA1−, PR+) or ((PR− |HER2+), SIAH2+) or ((PR+ |HER2+), KI67+) or margin positive | OTHER = (FOXA1+, or PR−) AND [(PR+ AND HER2−)|SIAH2−] AND [(PR− AND HER2−)|KI67−)] AND MARGIN STATUS NEGATIVE | 4.4 (2.1–9.0) | 9.09E−06 | 497 | Very Strong |
| 2 | Combined SIAH2, FOXA1 PR HER2 and KI67 form a significant risk prognosis for DCIS | DCIS risk | TOTAL | (FOXA1−, PR+) or ((PR− |HER2+), SIAH2+) or ((PR+ |HER2+), KI67+) | OTHER = (FOXA1+, or PR−) AND [(PR+ AND HER2−)|SIAH2−] AND [(PR− AND HER2−)|KI67−)] | 3.0 (1.6–5.7) | 5.50E−04 | 497 | Strong |
| 3 | Combined SIAH2, FOXA1 PR HER2 form a significant risk prognosis for DCIS | DCIS risk | TOTAL | (FOXA1−, PR+) or ((PR− |HER2+), SIAH2+) | OTHER = (FOXA1+, or PR−) AND [(PR+ AND HER2−) or SIAH2−] | 2.6 (1.4–4.9) | 2.70E−03 | 497 | Significant |
| 4 | Combined SIAH2, FOXA1 PR HER2 form a significant risk prognosis for DCIS in RT− | DCIS risk | RT− | (FOXA1−, PR+) or ((PR− |HER2+), SIAH2+); RT− | OTHER = (FOXA1+, or PR−) AND [(PR+ AND HER2−) or SIAH2−] AND RT− | 4.4 (1.9–10) | 2.70E−04 | 497 | Very Strong |

Table 9 provides a summary of the marker combinations that indicate a high risk (as used in this table only) of a subject diagnosed with DCIS experiencing an ipsilateral DCIS event after surgical removal of the primary DCIS.

In some embodiments, Table 11 provides a summary of the combinations that indicate a high risk of a subject diagnosed with DCIS experiencing an ipsilateral DCIS and/or invasive breast cancer after surgical removal of the primary DCIS.

TABLE 11

| Combination of Markers | High Risk of DCIS ipsilateral event | High Risk of Invasive ipsilateral event |
|---|---|---|
| PR+, FOXA1+ | | INVASIVE |
| (PR+, FOXA1+) or ( KI67+, SIZE > 5) | | INVASIVE |

TABLE 11-continued

| Combination of Markers | High Risk of DCIS ipsilateral event | High Risk of Invasive ipsilateral event |
|---|---|---|
| PR+ FOXA1+ COX-2+, KI67+ | | INVASIVE |
| (PR+ FOXA1+ COX-2+, KI67+) or (KI67+, SIZE+) | | INVASIVE |
| PR-, HER2-, and SIAH2- | | INVASIVE |
| PR-, HER2-, and SIAH2-, premenopausal | | INVASIVE |
| (PR-, HER2-, and SIAH2-) or (PR-, P16+, COX-2+) or (PR- P16+ KI67+) | | INVASIVE |
| PR-, FOXA1- | | INVASIVE |
| PR-, FOXA1- HER2- | | INVASIVE |
| PR-, FOXA1-, Pre-menopausal | | INVASIVE |
| (PR-, FOXA1-, and HER2-) or (PR-, P16+, COX-2+) or (PR- P16+ KI67+) | | INVASIVE |
| (PR-, FOXA1-, and HER2-) or (PR-, HER2-, and SIAH2-) or (PR-, P16+, COX-2+) or (PR- P16+ KI67+) | | INVASIVE |
| (PR+ FOXA1+ COX-2+, KI67+) or (PR-, HER2-, and SIAH2-) | | INVASIVE |
| (PR+, FOXA1+) or (PR-, HER2-, and SIAH2-) | | INVASIVE |
| SIAH2+ and PR- | DCIS | |
| SIAH2+ and FOXA1+ | DCIS | |
| SIAH2+ and HER2+ | DCIS | |
| SIAH2+ and post-menopausal | DCIS | |
| PR+ and FOXA1- | DCIS | |
| SIAH2+ PR- FOXA1+ | DCIS | |
| PR- FOXA1+ | DCIS | |
| PR+ and FOXA1- premenopausal | DCIS | |
| PR+ and FOXA1- or (KI67+ HER2-) or (KI67+ PR+) | DCIS | |
| (SIAH2+, PR- FOXA1+) or (KI67+ HER2-) or (KI67+ PR+) | DCIS | |
| (SIAH2+, PR-) or(SIAH2+ HER2+) or (KI67+ HER2-) or (KI67+ PR+) or (PR+ and FOXA1-) | DCIS | |
| (SIAH2+, PR- FOXA1+) or (SIAH2+ HER2+) or (KI67+ HER2-) or (KI67+ PR+) or (PR+ and FOXA1-) | DCIS | |
| SIAH2+ and PR- postmenopausal | DCIS | |

Table 11 outlines the relevant markers for identifying the level of risk that a subject with DCIS has for experiencing invasive breast cancer. Table 11 provides a summary of the combinations that indicate a high risk to a subject who already has DCIS experiencing invasive breast cancer and/or a recurrence of DCIS. The above results (Tables 1-9, 11, 13-15) are expressly contemplated for all embodiments of the various methods provided herein, as well as kits and compositions, etc.) As noted above, in some embodiments, only those who meet the elevated risk of invasive breast cancer are analyzed for HER2 and SIAH2 levels.

In some embodiments, any noted combination of the above markers or variables can be used for compositions or methods relating to DCIS recurrence and/or a risk of invasive breast cancer (as indicated). As noted herein, various combinations denote that the subject is at a relatively higher (or lower) risk of experiencing DCIS recurrence and/or a risk of invasive breast cancer. Thus, in some embodiments, this can be practically employed in terms of, for example, proper prognosis for the subject, advanced methods of treatment for the subject (for example, taking an approach that not only resolves DCIS that the subject currently has, but also addresses the risk level of DCIS recurrence and/or invasive breast cancer appropriately), methods for analyzing a sample (for example, a DCIS sample for various markers), compositions and kits that allow for the above noted methods, etc. In some embodiments, in a PR-background, low FOXA1 correlates with invasive events, while in a PR+ background, high FOXA1 correlates with invasive recurrence. Both correlations are reversed for DCIS events. In some embodiments, separate biomarker-based risk models (algorithms) can be used to predict invasive and DCIS events, and at least some biomarkers can be assessed differently in the context of other markers, rather than being assigned a single weighting in a linear algorithm. In some embodiments, the PR/FOXA1 combination identifies a subset of patients who experience a remarkable benefit from RT relative to the remaining patients. As shown, the studies indicate that the present approach to risk stratification modeling can accurately identify patients at risk for DCIS or invasive events after a primary DCIS diagnosis. In some embodiments, the models presented here (such as in the Examples below) are the basis of a comprehensive multi-marker panel. It should be noted that in certain embodiments, the risk models can be performed on a computing device while in other embodiments, the risk models can be performed manually.

In some embodiments, a method of analyzing a sample is provided. The method comprises analyzing a human DCIS tissue sample for PR, and either or both of: analyzing the sample for at least HER2 and SIAH2, and/or analyzing the sample for at least FOXA1. In some embodiments, depending upon the nature of the results, this indicates that the subject that provided the sample is at a high or elevated risk of invasive breast cancer (see, e.g., Tables 1-9, 11, 13, and 15).

In some embodiments, a method of analyzing a sample is provided. The method comprises analyzing a human DCIS tissue sample for a level of at least SIAH2 and FOXA1. In some embodiments, depending upon the nature of the results, this indicates that the subject that provided the sample is at a high or elevated risk of invasive breast cancer (see, e.g., Tables 1-9, 11, 13, and 15).

In some embodiments, a method of analyzing a sample is provided. The method comprises providing a DCIS sample from a subject having DCIS; 1) analyzing the DCIS sample for SIAH2, and analyzing the DCIS sample for at least one of HER2, PR, FOXA1, or any combination thereof; or 2) analyzing the DCIS sample for FOXA1 and PR. In some embodiments, depending upon the nature of the results, this indicates that the subject that provided the sample is at a high or elevated risk of invasive breast cancer (see, e.g., Tables 1-9, 11, 13, and 15).

In some embodiments, a method for prognosing a risk of an invasive breast cancer event in a subject is provided. The method comprises providing a DCIS sample from a subject, analyzing the DCIS sample for a level of at least PR, and at least either analyzing the sample for at least HER2 and SIAH2, or analyzing the sample for at least FOXA1. The method further comprises providing a prognosis based upon at least PR, HER2 and SIAH2 or based upon at least PR and FOXA1. In some embodiments, depending upon the nature of the results, this indicates that the subject that provided the sample is at a high or elevated risk of invasive breast cancer (see, e.g., Tables 1-9, 11).

In some embodiments, a method for prognosing a risk of an invasive breast cancer event in a subject is provided. The method comprises providing a DCIS sample from a subject, analyzing the sample for a level of at least SIAH2 and FOXA1, and prognosing the subject as having an elevated risk of an invasive breast cancer based upon the level of at least SIAH2 and FOXA1. In some embodiments, depending upon the nature of the results, this indicates that the subject that provided the sample is at a high or elevated risk of invasive breast cancer (see, e.g., Tables 1-9, 11).

In some embodiments, a method for prognosing a risk of an invasive breast cancer event in a subject is provided. The method comprises providing a DCIS sample from a subject, analyzing the sample for: a) PR, HER2, and SIAH2, or b) PR and FOXA1; and prognosing the subject as having an elevated risk of an invasive breast cancer event when at least one of: a) PR−, HER2−, and SIAH2−, b) PR+, FOXA1+, or c) PR+, FOXA1−, and Ki67+.

In some embodiments, a method for treating a subject at risk of having an invasive breast cancer is provided. The method comprises providing a subject having DCIS, wherein the subject has a DCIS that is at least one of: a) PR−, HER2−, and SIAH2−, b) PR+, FOXA1+, or c) PR+, FOXA1−, and Ki67+; and administering to the subject a therapy that is more aggressive than standard of care for DCIS.

In some embodiments, a method for prognosing a risk of an invasive breast cancer event in a subject is provided. The method can involve applying an algorithm to the protein and/or mRNA expression level as an additional transformative process, to thereby provide a signature for the marker. The method comprises providing a DCIS sample from a subject, analyzing the DCIS sample for a level of at least PR, and at least either analyzing the sample for at least HER2 and SIAH2, or analyzing the sample for at least FOXA1. The method further comprises providing a prognosis based upon at least a PR, HER2 and SIAH2 signature or based upon at least a PR and FOXA1 signature. In some embodiments, depending upon the nature of the results, this indicates that the subject that provided the sample is at a high or elevated risk of invasive breast cancer (see, e.g., Tables 1-9, 11, 13, and 15).

In some embodiments, a method for prognosing a risk of an invasive breast cancer event in a subject is provided. The method comprises providing a DCIS sample from a subject, analyzing the sample for a level of at least SIAH2 and FOXA1, and prognosing the subject as having an elevated risk of an invasive breast cancer based upon the signature of at least SIAH2 and FOXA1. In some embodiments, depending upon the nature of the results, this indicates that the subject that provided the sample is at a high or elevated risk of invasive breast cancer (see, e.g., Tables 1-9, 11, 13, and 15).

In some embodiments, a method for prognosing a risk of an invasive breast cancer event in a subject is provided. The method comprises providing a DCIS sample from a subject, analyzing the sample for: a) PR, HER2, and SIAH2, or b) PR and FOXA1; and prognosing the subject as having an elevated risk of an invasive breast cancer event using a signature comprising at least one of: a) PR−, HER2−, and SIAH2−, b) PR+, FOXA1+, or c) PR+, FOXA1−, and Ki67+. In some embodiments, depending upon the nature of the results, this indicates that the subject that provided the sample is at a high or elevated risk of invasive breast cancer (see, e.g., Tables 1-9, 11, 13, and 15).

In some embodiments, any of the methods, compositions, kits, systems, etc. described herein, can be used employing one or more of the following markers and/or combinations (and/or other noted variable), outlined in Tables 1-9 11, 14, and 15 for markers that are relevant to DCIS (Table 9 for the noted combinations) and Tables 11, 13 and 15 for markers that are relevant to invasive breast cancer. The HER2 and SIAH2 analysis processes noted above to determine the appropriate therapy to administer can be part of or combined with any of these techniques, thereby allowing one to identify a subject at elevated risk of invasive breast cancer (through these techniques, for example, and then determine if they should receive radiation therapy or some non-radiation therapy treatment).

In some embodiments, any of the above methods can be combined with any one or more of the following further aspects as to methods.

In some embodiments, the subject is high risk if they are PR positive and there is a very high level of FOXA1 (e.g., "elevated risk"). In some embodiments, if a sample is PR positive, then one further analyzes the sample for Ki67, size, or both Ki67 and size. In some embodiments, if the sample is PR positive, and FOXA1 negative, then one further analyzes the sample for a level of Ki67, size, or a level of Ki67 and size, wherein Ki67 positive, a size larger than 5 mm of DCIS, or both, which indicates high risk (e.g., "elevated risk"). In some embodiments, the method further comprises analyzing for p16, COX2, and Ki67 in order to determine elevated risk levels.

In some embodiments, any of the methods and/or compositions for determining elevated risk of invasive breast cancer provided in U.S. Pat. Pub. Nos. 20100003189, 20120003639, and 20170350895 can be employed to identify a subject having an elevated risk of invasive breast cancer, the entireties of each of which is hereby incorporated by reference.

In some embodiments, one or more of the denoted markers can be analyzed and/or assayed for. In some embodiments, the markers of HER2 and SIAH2 are assayed for separate from other markers. In some embodiments, HER2 and SIAH2 are assayed as part of the process for determining elevated risk in the subject and/or sample. In some embodiments, HER2 and SIAH2 are assayed for with one or more of ER, PR, COX-2, FOXA1, Ki67, and/or p16. In some embodiments, any of the following assays for markers can be done in combination with HER2 and/or SIAH2, for a subject that has DCIS.

In some embodiments, if the sample is PR positive, one can further analyze the sample for a level of COX-2. In some embodiments, if the sample is PR positive, then one can further analyze the sample for Ki67 or size, or both Ki67 and size. In some embodiments, one can analyze the sample for p16 with Ki-67 or p16 with COX-2. In some embodiments, the method further comprises analyzing at least the following combinations: a) PR, HER2, and SIAH2, b) PR, FOXA1, and COX-2, and c) PR, FOXA1, and Ki67. In some embodiments, one also determines if the subject is HER2 positive and SIAH2 positive and has DCIS to then determine if the subject will be receptive to radiation therapy or if a non-radiation therapy, such as an antibody to HER2, should be employed.

In some embodiments, markers in addition to those disclosed and described herein can be analyzed and/or assayed for. These additional markers are disclosed and described in U.S. patent application Ser. No. 12/373,047, filed May 13, 2009 and U.S. patent application Ser. No. 13/094,729, filed Apr. 26, 2011, the contents of both applications are incorporated herein by reference in their entirety.

In some embodiments, the method further comprises analyzing at least COX-2, Ki67, p16, PR and HER2. In some embodiments, if the sample is PR positive, one can further analyze the sample for a level of COX-2, wherein COX-2+ with at least FOXA1+ indicates a high risk of invasive breast cancer. In some embodiments, if the sample is PR positive and there is a very high level of FOXA1, there is a high risk of invasive breast cancer. In some embodiments, if the sample is PR positive, then one can further analyze the sample for Ki67, size, or both Ki67 and size. In some embodiments, if the sample is PR positive and FOXA1−, one can further analyze the sample for a level of Ki67, size, or a level of Ki67 and size. Ki67+, a size larger than 5 mm of DCIS, or both, indicates an elevated risk of invasive breast cancer. In some embodiments, the method further comprises analyzing the sample for p16, COX-2, and Ki67. In some embodiments, one also determines if the subject is HER2 positive and SIAH2 positive and has DCIS to then determine if the subject will be receptive to radiation therapy or if a non-radiation therapy, such as an antibody to HER2, should be employed.

In some embodiments, analysis of each marker is carried out in parallel with each other. In some embodiments, analysis of each marker is carried out at overlapping times.

In some embodiments, PR analysis occurs first and any further analysis depends upon the result of the PR analysis. In some embodiments, there is no required order for any of the tests and/or analysis for any of the markers provided herein.

In some embodiments, the method further comprises determining a prognosis of the subject with DCIS. At least a level of SIAH2 and FOXA1 relative to the non-DCIS control indicates that the subject has a poor prognosis or wherein no significant difference in the expression of SIAH2 and FOXA1 relative to a non-tumor control indicates that the subject has a good prognosis.

In some embodiments, the DCIS sample is further analyzed for COX-2. In some embodiments, the DCIS sample is further analyzed for p16. In some embodiments, the DCIS sample is analyzed for at least SIAH2, FOXA1, and PR. In some embodiments, the DCIS sample is further analyzed for HER2. In some embodiments, the DCIS sample is further analyzed for COX-2. In some embodiments, the DCIS sample is further analyzed for Ki67. In some embodiments, the DCIS sample is further analyzed for p16. In some embodiments, one also determines if the subject is HER2 positive and SIAH2 positive and has DCIS to then determine if the subject will be receptive to radiation therapy or if a non-radiation therapy, such as an antibody to HER2, should be employed.

In some embodiments, the analysis (staining and/or scoring) includes SIAH2 and FOXA1. In some embodiments, the analysis further includes at least one of the following further combinations: 1) p16, 2) Ki67, 3) PR, 4) COX-2, 5) HER2, 6) p16 and Ki67, 7) p16 and PR, 8) p16 and COX-2, 9) p16 and HER2, 10) HER2 and Ki67, 11) HER2 and PR, 12) HER2 and COX-2, 13) p16, COX-2, and HER2, 14) HER2, COX-2, and Ki67, 15) HER2, COX-2, and PR, 16) HER2 and COX-2, 17) p16, Ki-67, COX-2, and HER2, 18) Ki-67, HER2, COX-2, and PR, and/or 19) Ki-67, HER2, COX-2, PR, and p16. In some embodiments, one also determines if the subject is HER2 positive and SIAH2 positive and has DCIS to then determine if the subject will be receptive to radiation therapy or if a non-radiation therapy, such as an antibody to HER2, should be employed.

In some embodiments, the DCIS lesion is further analyzed for grade, necrosis, size, and/or margin status.

In some embodiments, the method further comprises prognosis of a risk by including age, menopausal status, mammographic density, tumor palpability of the subject.

In some embodiments, any of the "PR" steps, methods, compostions, etc. provided herein can be interchanged with an ER step (where ER staining and/or scoring is performed).

Reports/Recommendations

In some embodiments, any of the present methods can further comprise preparing a report regarding the risk associated with the human DCIS tissue sample. In some embodiments, the report is a written report providing the risk of invasive breast cancer. In some embodiments, the report is generated from and/or includes one or more of the marker combinations provided in Tables 1-9, 11 and 13-15. In some embodiments, the report also details if the subject will be receptive to radiation therapy or if a non-radiation therapy, such as an antibody to HER2, should be employed.

In some embodiments, any of the present methods further comprise providing a report regarding a level of risk of a subsequent DCIS event. In some embodiments, the report is a written report providing the risk of a subsequent DCIS event. In some embodiments, the report is generated from and/or includes one or more of the marker combinations provided in Tables 1-9, 11 and 13-15.

In some embodiments, the method further comprises recommending a treatment given a result from analyzing the DCIS sample for SIAH2 and at least one of HER2, PR, FOXA1, or any combination thereof. In some embodiments, the treatment is less aggressive than would have otherwise been recommended, without the method predicting a low likelihood of invasive breast cancer. In some embodiments, the treatment is more aggressive than would have otherwise been recommended, without the method predicting a high likelihood of invasive breast cancer. In some embodiments, the treatment is less aggressive than would have otherwise been recommended, without the method predicting a low likelihood of a recurrence of DCIS. In some embodiments, the treatment is more aggressive than would have otherwise been recommended, without the method predicting a high likelihood of a recurrence of DCIS. In some embodiments, the report also details if the subject will be receptive to radiation therapy or if a non-radiation therapy, such as an antibody to HER2, should be employed (e.g., depending upon the HER2 and SIAH2 results).

In some embodiments, the method further comprises determining a risk of DCIS, invasive breast cancer, or both. In some embodiments, the method further comprises providing a written report regarding a risk of DCIS, invasive breast cancer, or both (e.g., in line with Tables 1-9, 11 and 13-15) as well as whether or not the subject should receive a non-radiation therapy (such as an antibody to HER2) or a radiation therapy.

Treatment

In some embodiments, any of the above noted methods can include and/or be followed by an appropriate therapy for the subject, given the subject's reclassified risk of subsequent DCIS and/or invasive breast cancer and/or responsiveness to radiation therapy (for those in the elevated risk of invasive breast cancer category). In some embodiments, such therapies can be appropriate to reduce a risk of invasive breast cancer, if that is the risk. In some embodiments, for those at an elevated risk of invasive breast cancer, the appropriate treatment of non-radiation (for those that are HER2+ and SIAH+) or radiation therapy (for those that are not both HER2+ and SIAH+) can be provided to the subject or received by the subject. In some embodiments, the non-radiation therapy is an antibody to HER2, such as trastuzumab.

In some embodiments, a therapy appropriate to reduce a risk of DCIS recurrence comprises at least one of surgical resection, radiation therapy, anti-hormone therapy. In some embodiments, a therapy can be appropriate if one knows that the subject has a low likelihood of an invasive event, but would not be appropriate if one knows that the subject has a high likelihood of an invasive breast cancer event and how likely the subject is refractory to radiation therapy.

In some embodiments, a therapy appropriate to reduce a risk of invasive breast cancer comprises at least one of mastectomy, targeted HERs therapy, receptor-targeted chemotherapy. In some embodiments, such a therapy can be appropriate if one knows that the subject has a high likelihood of an invasive event, but would not be appropriate if one knows that the subject has a low likelihood of an invasive breast cancer event. In some embodiments, the therapy is appropriate if the subject is not, non-responsive to the therapy. In some embodiments, a subject who is predicted to be refractory to radiation therapy will not receive or be administered a radiation therapy.

In some embodiments, any of the above methods can be followed by "watchful waiting" or other relatively minimal/intrusive therapies. For example, when none of the high risk categories are met for invasive breast cancer, and if the subject has no DCIS risk (or is okay with having a DCIS risk), then the approach to treating the DCIS can be to take no immediate action, which can include more frequent breast imaging to provide an early identification of an ipsilateral breast event.

Additional aspects and approaches regarding possible therapeutic actions that are specific for the present DCIS subjects are provided below.

Kit

In some embodiments, a kit is provided. The kit can include a FOXA1 probe, and a SIAH2 probe. In some embodiments, the kit further comprises a COX-2 probe, a Ki67 probe, a p16 probe, a PR probe, and a HER2 probe. In some embodiments, the probe is an isolated antibody. In some embodiments, the probe is a nucleic acid that selectively hybridizes to FOXA1, SIAH2, COX-2, Ki67, p16, PR or HER2 as appropriate. In some embodiments, the kit contains enough of the probe and/or the probe is sensitive and/or selective enough such that the "+" and "−" states of one or more of the markers in Tables 1-9, 11 and 13-15 can be adequately distinguished from one another. In some embodiments, any of the kits provided herein will include at least probes sufficient for HER2 and SIAH. In some embodiments, the HER2 and SIAH2 probes can be part of their own kit or performed separately.

In some embodiments, an antibody composition is provided that includes an isolated FOXA1 antibody, and an isolated SIAH2 antibody. In some embodiments, the antibody composition further comprises an isolated COX-2 antibody, an isolated Ki67 antibody, an isolated p16 antibody, an isolated PR antibody, and an isolated HER2 antibody. In some embodiments, a HER2 antibody and a SIAH2 antibody are provided in combination with one or more of the other antibodies.

In some embodiments, a solid support comprising probes or antibodies specific for at least SIAH2 and FOXA1 is provided. In some embodiments, the probes or antibodies consists essentially of probes or antibodies specific for the prediction of DCIS or invasive breast cancer in a subject who has DCIS, including at least HER2 and SIAH. In some embodiments, a solid support comprising probes or antibodies specific for at least SIAH2 and HER2 is provided.

In some embodiments, the subject and/or sample to be analyzed can be a patient (or from a patient). In some embodiments, the subject has, or had, DCIS. In some embodiments, the sample came from the DCIS of the subject in question. There are a variety of ways in which such a subject can be identified.

Sample

In some embodiments, the DCIS sample itself can be processed in any number of ways to prepare it for screening for the markers. In some embodiments, the DCIS sample has been surgically removed from a patient and preserved. In some embodiments, the DCIS sample is obtained by surgical removal. In some embodiments, the DCIS sample is cut into one or more blocks, such as 2, 3, 4, 5 or more blocks.

In some embodiments, a level of SIAH2 and HER2, and/or at least one of PR, FOXA1, or any combination thereof is at least one of: a RNA level, a DNA level, a protein level. In some embodiments, a level of SIAH2 and HER2 and/or at least one of PR, FOXA1, or any combination thereof is at least one of: a RNA level, a DNA level, a protein level. In some embodiments, a level of SIAH2 and HER2 and FOXA1 is at least one of: a RNA level, a DNA level, a protein level.

In some embodiments, a signature comprising a level of SIAH2 and HER2, PR, FOXA1, or any combination thereof is at least one of: a RNA level, a DNA level, a protein level. In some embodiments, a signature comprising a level of SIAH2 and HER2, and at least one of PR or FOXA1 is at least one of: a RNA level, a DNA level, a protein level. In some embodiments, a signature comprising a level of SIAH2 and HER2 and FOXA1 is at least one of: a RNA level, a DNA level, a protein level.

In some embodiments, a method of preparing a sample is provided. The method comprises obtaining a DCIS sample from a subject and preparing it so that its DNA, RNA, and/or protein can be analyzed for at least SIAH2 and HER2 and/or FOXA1.

In some embodiments, the sample is preserved. In some embodiments, the sample is preserved via freezing. In some embodiments, the sample goes through (or does not go through) embedding in a chemical such as Optimal Cutting Temperature (OCT) compound, or fixation with a chemical(s), including, without limitation, formalin, formaldehyde, quaternary ammonium salts, alcohol, acetone, or other chemicals that preserve or extract DNA, RNA, and/or protein. In some embodiments, the technique used is one that allows SIAH2 and HER2 and/or FOXA1 DNA, RNA, and/or protein to be preserved in an adequate amount and state so that SIAH2 and HER2 and/or FOXA1 can be analyzed as provided herein.

In some embodiments, the DCIS sample is processed to allow for immunohistochemistry of at least SIAH2 and HER2 and/or FOXA1. In some embodiments, at least three such samples (such as in the form of slices) can be prepared).

In some embodiments, analyzing the sample comprises determining an amount of a specified RNA in the sample. The amount of RNA for each marker can be determined by any number of techniques, some of which are discussed elsewhere in the present application. In some embodiments, the RNA level is determined by at least one of: an assay involving nucleic acid microarray, reverse transcriptase-polymerase chain reaction, in situ nucleic acid detection, or a next generation sequencing method. In some embodiments, expression of at least one of SIAH2 and HER2 and FOXA1 is measured by real time quantitative polymerase chain reaction or microarray analysis.

In some embodiments, the RNA level is determined by: an assay involving nucleic acid microarray, reverse transcriptase-polymerase chain reaction, in situ nucleic acid detection, or a next generation sequencing method.

In some embodiments, analyzing the DCIS sample comprises determining an amount of a specified protein in the sample. The amount of protein for each marker can be determined by any number of techniques, some of which are discussed elsewhere in the present application. In some embodiments, the protein level is determined by immunohistochemistry, immunofluorescence, or mass spectrometry.

In some embodiments, patient specimens used for the detection of the biomarkers can be surgically removed breast tissues that are cut into small blocks and submerged in fixative. In some embodiments, following fixation, the blocks can be dehydrated and then embedded in paraffin wax. In some embodiments, the small blocks are no more than 20 mm in length and 5 mm in thickness to allow complete penetration of the fixative. In some embodiments, the fixation occurs in 10% neutral-buffered formalin for 24 to 48 hours at room temperature to preserve tissue structure and compartmentalization of the various markers. However, other fixatives and fixation times (e.g., 6 to 72 hours) can also be compatible with the marker assays. In some embodiments, assays are optimized to use specimens that have been flash frozen (e.g., in liquid nitrogen), rather than being fixed and embedded.

In some embodiments, the process of sample processing can include dehydration and embedding, which can be done manually or automated with a tissue processing instrument. In either case, the aqueous portion of the tissue and the fixation solution can be replaced by passing the block through a series of increasingly concentrated alcohol solutions. After reaching 100% alcohol, the alcohol is replaced using a chemical like xylene (or a xylene-free equivalent), followed by introduction of molten, low-melting-temperature (e.g., approximately 45° C.) paraffin wax for embedding. The FFPE blocks can be stored for many years prior to analysis. In some embodiments, "cores" of DCIS tissue can be cut from these blocks using a hollow needle and then inserted in an array format in a separate block of paraffin. Such "tissue microarrays" (TMAs) allow assessment of multiple tissues on a single section/microscope slide.

In some embodiments, ultrathin sections, approximately three to five micrometers in thickness, can be cut off the formalin-fixed paraffin-embedded (FFPE) tumor blocks using a microtome. The sections can be mounted onto glass microscope slides, ensuring that the tissue does not become folded or fragmented, which could interfere with the assays. The glass microscope slides can contain a positively charged surface in order bind to the negatively charged tissue sections, although other methods of tissue binding, including adhesives, can also be compatible.

In some embodiments, wax removal and rehydration of the tissue sections can then be carried out. These processes can be done manually or automated with certain staining instruments. Wax can be removed from the tissue sections on the slides through heating and/or immersion in a solution of xylene (or an equivalent xylene-free solution, such as Novocastra Bond Dewaxing Solution). Rehydration can be accomplished by passing the slides through a series of decreasingly concentrated alcohol solutions until a concentration of 0% is reached (pure water). Following wax removal and rehydration, the tissue sections can be stained with hematoxylin and eosin (H&E) and for a variety of molecular markers using immunohistochemistry (IHC) and/or in situ hybridization (ISH) assays and then assessed by pathologists or histotechnologists, as described below. The above processing steps can be performed for any of the methods provided herein in regard to the various markers (HER2 and SIAH2 and at least one of COX-2, Ki-67, PR, p16, and FOXA1).

DCIS Diagnosis and Assessment of Pathological Factors—Hematoxylin and Eosin Staining In some embodiments, the subject and/or sample is confirmed as a DCIS sample or a subject having DCIS by any of a variety of ways known to one of skill in the art. This can occur before any of the other method steps provided herein (in some embodiments). Provided herein is a set of non-exhaustive options for identifying someone with DCIS.

In some embodiments, hematoxylin and eosin (H&E) can be used to stain at least one tissue section from each patient (or set of arrayed patients) in order to confirm the DCIS diagnosis, assess certain pathological features (nuclear grade, architectural pattern[s], and the presence or absence of necrosis), and as a reference for the interpretation of the molecular marker assays. This histological stain allows the differentiation of nuclei and cytoplasm in individual cells, as well as various cell types and stromal tissue components, based on the color of the staining. The staining can be done manually or automated with a special staining instrument. In either case, the section can be submerged in hematoxylin solution for approximately four minutes to stain the nuclei blue, and then rinsed with tap water (alkaline). In some embodiments, next, the section can be exposed briefly (typically only a few seconds) to an acid alcohol solution to remove hematoxylin background staining, and then rinsed with tap water (alkaline). A "bluing" solution (e.g., lithium carbonate for 30 to 60 seconds) next may be applied to enhance the blue color of the hematoxylin in the nuclei, followed by rinsing with water. Eosin solution is then applied for approximately two minutes to stain other (eosinophilic) cellular components, followed by rinsing with water. The tissue is dehydrated with an alcohol series and cleared with xylene (or equivalent), and a cover slip is attached using mounting medium. Other options are also known to those of skill in the art. In some embodiments, any method for confirming the current presence of DCIS can be used on the sample. In some embodiments, no confirmation process is required. The above variables can be altered as appropriate by one of skill in the art.

DCIS itself can be identified in a sample or a subject in a variety of ways. Intraductal proliferative lesions include a group of cytologically and architecturally diverse epithelial proliferations originating in the terminal duct lobular unit (TDLU) and can be associated with an increased risk (of varying magnitude) for the subsequent development of invasive breast cancer. DCIS can be regarded as a possible true precursor lesion of invasive breast cancer. However, as demonstrated, not all DCIS events go on to form invasive breast cancer. There are various grades of DCIS (which, unless otherwise denoted, are all encompassed within the term "DCIS").

"Low grade DCIS" is composed of small, monomorphic cells, growing in a variety of patterns, including arcades, micropapillae, cribriform or solid patterns. The nuclei are generally of uniform size and have a regular chromatin pattern with inconspicuous nucleoli with rare mitotic figures. Low-grade DCIS requires either involvement of two spaces or one or more duct cross sections exceeding 2 mm in diameter. Although desquamated cells within the ductal lumen may be present, frank necrosis/comedo-type histologic features are not typical for low grade DCIS. In some embodiments, the definition is the CAP definition.

Cytologic features of DCIS can include: monotonous, uniform rounded cell population; subtle increase in nuclear-cytoplasmic ratio; equidistant or highly organized nuclear distribution; round nuclei; and hyperchromasia may or may not be present. Architectural features can include arcades, cribriform, solid and/or micropapillary.

"Intermediate grade DCIS" is often composed of cells cytologically similar to those of low grade DCIS, forming solid, cribriform or micropapillary patterns, but with some ducts containing intraluminal necrosis. Others display nuclei of intermediate grade with occasional nucleoli and coarse chromatin; necrosis may or may not be present.

"High grade DCIS" is usually larger than 5 mm, but even a single <1 mm duct with the typical morphological features is sufficient for diagnosis. It is composed of highly atypical cells proliferating as one layer, forming micropapillae, cribriform or solid patterns. Nuclei are high grade, markedly pleomorphic, poorly polarized, with irregular contour and distribution, coarse, clumped chromatin and prominent nucleoli. Mitotic figures are usually common but their presence is not required. Comedonecrosis is frequently associated with high grade DCIS, but not necessary for diagnosis. Even a single layer of highly anaplastic cells lining the duct in a flat fashion is sufficient.

"Atypical Ductal Hyperplasia" is distinct from DCIS. The morphological features of atypical ductal hyperplasia are identical to those of low-grade DCIS, but ADH is limited in size. There are two quantitative criteria that distinguish ADH from low-grade DCIS: the presence of homogeneous involvement of not more than 2 membrane-bound spaces; or a size of ≤2 mm. The use of one or both criteria is considered appropriate by the authors of the WHO classification. In some embodiments, the definition is the CAP definition.

Histologic Confirmation of DCIS

In some embodiments, the subject is one who has at least one form of DCIS. In some embodiments, the presence of DCIS can be confirmed by any of a variety of techniques, including, for example, using slide-mounted tissue sections stained with hematoxylin and eosin (H&E) or an equivalent histology stain (noted above). In some embodiments, the assessment can be done consistent with WHO classification of tumors of the breast (Lakhani S R. WHO classification of tumours of the breast. Lyon: International Agency for Research on Cancer, 2012, and Tavassoli F A, Devilee P. Pathology and genetics of tumours of the breast and female genital organs. Lyon: IARC Press, 2003)—see definition of DCIS section. These references contain sample images and review characteristic features of DCIS and differential diagnosis with other breast disease entities, such as invasive breast cancer (including microinvasion defined as invasion ≤1 mm), lobular carcinoma in situ (LCIS), in situ Paget's, atypical ductal hyperplasia (ADH), sclerosing adenosis, etc., the entireties of which are incorporated herein by reference).

In some embodiments, when histological features are not sufficient for the diagnosis of DCIS, the diagnosis can be confirmed by a second pathologist. Additional tissue blocks can be employed for morphologic review.

Cases Suspected to have Invasive (or Microinvasive) Carcinoma Based Upon Morphologic Features:

Normal breast ducts and lobules as well as intraductal epithelial proliferations are composed of two epithelial layers. Loss of the outer myoepithelial layer is the hallmark of infiltrating carcinoma of the breast. The outer myoepithelial layer is retained in all benign proliferative processes as well as ductal carcinoma in situ. Consequently identification of the presence or loss of myoepitheilium using antibodies to the myoepithelial-specific proteins can be helpful in distinguishing in situ from infiltrating carcinoma in circumstances where morphology may be equivocal (Kalof A N et al., Kalof A N, Tam D, Beatty B, Cooper K. Immunostaining patterns of myoepithelial cells in breast lesions: a comparison of CD10 and smooth muscle myosin heavy chain. J Clin Pathol 2004; 57, 625-629; Barbareschi M et al., Barbareschi M, Pecciarini L, Cangi M G et al. p63, a p53 homologue, is a selective nuclear marker of myoepithelial cells of the human breast. Am J Surg Pathol; 25, 1054-1060, 2001).

In some embodiments, if there is unequivocal morphologic evidence of invasion, including microinvasion, the patient can be considered to be ineligible for the prognostic DCIS testing (and will not be tested, or can be excluded from the assay). In some embodiments, if, upon morphologic examination of the tumor focus, there is a question of invasion of microinvasion, additional myoepithelial marker immunostudies (p63 and/or smooth muscle myosin heavy chain (SMMHC) immunostains) can be performed to examine the continuity of the myoepithelial cell layers and confirm and/or exclude the presence of (micro)invasive carcinoma. In some embodiments, other follow procedures can be performed for confirmation, where appropriate.

Cases Suspected to be of Lobular Origin Based Upon Morphologic Features:

It has been demonstrated that in histologic settings where ductal and lobular neoplasia might be confused, particularly in the setting of in situ carcinoma, where there can be significant differences in patient management, loss of expression of E-cadherin by immunohistochemistry can confirm the diagnosis of lobular carcinoma, even in the setting of non-classical morphologic findings (Acs G et al., Acs G, Lawton T J, Rebbeck T R, LiVolsi V A, Zhang P J. Differential expression of E-cadherin in lobular and ductal neoplasms of the breast and its biologic and diagnostic implications. Am J Clin Pathol 2001; 115, 85-98, 2001). In lobular neoplasia, mutations in the E-cadherin gene result in loss of expression of E-cadherin, a cell surface adhesion molecule present in normal breast epithelium and ductal carcinoma. The role of E-cadherin in homotypic cell-cell binding, loss of expression of this cell surface protein accounts for the characteristic non-cohesive growth pattern of lobular carcinoma.

In some embodiments, if, upon examination of an intraductal epithelial proliferation, it is unclear whether the intraductal tumor is ductal or lobular in nature, an E-cadherin immunostain can be performed to confirm ductal or lobular differentiation. In some embodiments, if lobular carcinoma in situ (LCIS) is confirmed histologically or by loss of e-cadherin by immunohistochemistry, the patient could be ineligible for further prognostic testing (e.g., will not be tested, or can be excluded from the assay). In some embodiments, if the subject currently has LCIS and not DCIS, the subject is not treated with the method. In some embodiments, if there is no evidence of DCIS or invasive carcinoma, additional tissue blocks can be requested for morphologic review.

In some embodiments, a sample or subject is excluded from the method if one or more of the following applies: a) no DCIS identified, b) invasive or microinvasive carcinoma identified, c) LCIS, not DCIS identified, c) quantitative criteria for low/intermediate DCIS not met: 1) the presence of homogeneous involvement of more than 2 membrane-bound spaces and/or a size of <2 mm. (No quantitative criteria required for high grade DCIS), or 2) tissue folded over in area of interest—not possible to score adequately.

Nuclear Grade Determination

In some embodiments, DCIS nuclear grade can be determined by using slide-mounted tissue sections stained with hematoxylin and eosin (H&E) or an equivalent histology stain. In some embodiments, the assessment can be consistent with the College of American Pathologists "Protocol for the Examination of Specimens from Patients with Ductal Carcinoma in Situ (DCIS) of the Breast" (Lester S C, Bose S, Chen Y Y et al. Arch Pathol Lab Med 2009; 133, 15-25.), based on references therein. Nuclear grades of I (low), II (intermediate), and/or III (high) will be noted based on Table 12:

TABLE 12

| Feature | Grade I (Low) | Grade II (Intermediate) | Grade III (High) |
|---|---|---|---|
| Pleomorphism | Monotonous (monomorphic) | Intermediate | Markedly pleomorphic |
| Size | 1.5 × to 2 × the size of a normal RBC or a normal duct epithelial cell nucleus | Intermediate | >2.5 × the size of a normal RBC or a normal duct epithelial cell nucleus |
| Chromatin | Usually diffuse, finely dispersed chromatin | Intermediate | Usually vesicular with irregular chromatin distribution |
| Nucleoli | Only occasional | Intermediate | Prominent, often multiple |
| Mitoses | Only occasional | Intermediate | May be frequent |
| Orientation | Polarized toward luminal spaces | Intermediate | Usually not polarized toward the luminal space |

\* RBC indicates red blood cell.

Adapted from Lester S et al. Arch Pathol Lab Med 133:15-25 2009.

It is not uncommon to find admixture of various grades of DCIS within the same biopsy. In some embodiments, when more than one grade of DCIS is present, the proportion (percentage in deciles) of each grade will be noted. In some embodiments subjects with extensive disease and high grade DCIS will not be considered to be low risk for a subsequent ipsilateral breast event. In some embodiments, any of the methods provided herein can start with first determining if the subject has DCIS and/or the DCIS nuclear grade. In some embodiments, the method does not include determining nuclear grade.

Necrosis Determination

In some embodiments, the presence and extent of necrosis in DCIS can be examined using slide-mounted tissue sections stained with hematoxylin and eosin (H&E) or an equivalent histology stain. The assessment can be done consistent with the College of American Pathologists "Protocol for the Examination of Specimens from Patients with Ductal Carcinoma in Situ (DCIS) of the Breast" (June 2012), based on references therein. In some embodiments, necrosis can be classified as follows: A) Not identified: No evidence of necrosis, B) Focal (punctuate): Small foci, indistinct at low magnification, or single cell necrosis, or C) Central (comedo/extensive): The central portion of an involved ductal space is replaced by an area of expansive necrosis that is easily detected at low magnification. Ghost cells and karyorrhectic debris are generally present. Although central necrosis is generally associated with high-grade nuclei (comedo DCIS), it can also occur with DCIS of low or intermediate nuclear grade. In some embodiments, any of the methods provided herein can include determining necrosis.

IHC Markers Staining/Scoring

When a formalin-based fixation method is used, it creates molecular cross-links in proteins, thereby masking epitopes from recognition by antibodies, and other fixation/preservation methods can also mask epitopes. In such embodiments, epitope retrieval can be a pre-treatment step that allows one to unmask the epitopes by reversing, at least in part, the changes introduced by fixation/preservation. Thus, in some embodiments, any of the methods and/or kits provided herein can include a step or ingredient for epitope retrieval.

Epitope retrieval can be done in different ways by varying the chemicals in the solution (e.g., buffers, proteolytic enzymes, chelators, etc.), the pH of the solution, the temperature of the solution (e.g., as applied by a water bath, pressure cooker, autoclave, or microwave oven), and/or the time in the solution, etc. In addition to the specific methods described in the examples below, many of these other methods could be used to achieve substantially equivalent results, depending on the tissue source, primary antibody, and other factors.

Multiple antibodies are commercially available and/or have been reported in the literature for each protein marker described herein (COX-2, Ki67, HER2, p16, PR, SIAH2, and FOXA1, or those products in Table 0.1), and new antibodies can also be created. In some embodiments, the antibodies are raised against and/or recognize different epitopes on the protein markers (COX-2, Ki67, HER2, p16, PR, SIAH2, and FOXA1), and, in other cases, the antibodies are raised against and/or recognize the same (or similar) epitopes. The usefulness of an individual antibody in an assay depends upon its affinity and specificity for the epitope, as well as the accessibility of the epitope in the assay (e.g., after epitope retrieval in and IHC assay). Some antibodies recognize more than one protein marker and are, therefore, not typically suitable for a specific marker assay. Other antibodies have low affinity or recognize an epitope that remains inaccessible in certain samples and are, therefore, not suitable for certain assay types. For example, an antibody that has a use for an immunoblot of fresh protein lysate may not have utility in an IHC assay on FFPE tissue due to the inability to unmask its epitope through epitope retrieval.

The concentrations of primary antibody concentrates commercially available from manufacturers vary based on the production method (e.g., tissue culture supernatant, ascites fluid, or whole antiserum), and whether any purification was done (e.g., affinity purification), but they are typically in the range of about 0.1 to 10 mg/ml. The optimal final primary antibody concentration for incubation on the sections depends on such factors as the binding characteristics of the specific antibody, the incubation time and temperature, and other factors unique to the individual laboratory, but it is typically in the range of 0.1 to 10 µg/ml, and dilutions ranging from about 1:10 to 1:1,000 are typically used. In some embodiments, staining results can be achieved with an antibody over a range of final primary antibody concentrations, as well as incubation times and temperatures.

In some embodiments, a Novocastra Bond Refine Polymer system can be used for detection of the primary antibody. This system includes a polymer backbone to which multiple secondary antibodies (against rabbit IgG) and enzymes are attached, as well as a rabbit anti-mouse IgG linker (when used with mouse primary antibodies). The enzymes catalyze a chemical reaction with DAB to form a brown precipitate that is visualized during marker scoring. In some embodiments one of several other detection methods can produce adequate results, including systems that utilize avidin-biotin complex (ABC), labeled streptavidin-biotin (LSAB), catalyzed signal amplification, and/or other technologies that are available in a variety of formats from a number of different manufacturers. In some embodiments, the ABC and other polymer-based technologies (e.g., Dako EnVision+) can be utilized with similar results (for detection).

In some embodiments, chromogen DAB can be used for final visualization of the marker through an enzymatic reaction of horseradish peroxidase (HRP) that produces a brown precipitate at the site of the antibody binding. In some embodiments, HRP can be used in combination with the chromogen 3-amino-9-ethylcarbazole (AEC) to produce red coloration with substantially equivalent results. Other options include the enzyme alkaline phosphatase in combination with the chromogens nitro blue tetrazolium chloride (NBT) and 5-bromo-4-chloro-3-indolyl phosphate (BCIP), and the enzyme glucose oxidase in conjunction with NBT-both of which produce a bluish-purple coloration. There are a variety of enzyme/chromogen combinations that can produce results.

The following section outlines various representative embodiments for staining and scoring seven markers (PR, HER2, COX-2, Ki-67, SIAH2, FOXA1, and p16). In some embodiments, other markers that serve the same function can be substituted for any one or more of these markers. In some embodiments ER can be substituted for PR. In some embodiments, any one or more of these markers can be used in the combinations suggested in the accompanying tables (Tables 1-9, 11 and 13-15). In some embodiments, one or more of the noted markers can be employed (e.g., for staining and/or scoring) but a corresponding staining technique and/or corresponding score is used instead (as outlined herein). In some embodiments, a method for determining whether or not a person is at elevated risk of DCIS, and that involves HER2 and SIAH2 analysis can then use the same HER2 and SIAH2 data to determine if the subject will be responsive to radiation therapy or should instead receive non-radiation therapy, such as a HER2 antibody, such as trastuzumab.

PR Staining

In some embodiments, any technique for PR staining can be used, as long as it is adequate to observe the degree of PR fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above that above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, to assess progesterone receptor (PR; PGR; HGNC:8910) by IHC, a Leica BOND-MAX automated staining instrument can be used to conduct the following steps with rinsing between each step. Dewaxed and rehydrated tissue sections can be treated with Novocastra Peroxide Block (3-4% hydrogen peroxide) (peroxidase blocking step), followed by Novocastra Bond Epitope Retrieval Solution 1 (based on a 10 mM sodium citrate buffer plus 0.05% Tween 20, pH 6.0 solution) for 30 minutes at 95° C. to 100° C. (epitope retrieval step). The tissue sections are then incubated at room temperature with mouse monoclonal antibody PgR 636 (Dako M3569) diluted 1:50 in Novocastra Primary Antibody Diluent for 30 minutes (primary antibody step), followed by Novocastra Post Primary solution for 15 minutes (rabbit anti-mouse to introduce IgG linkers), followed by Novocastra Bond Refine Polymer for 15 minutes (anti-rabbit poly-HRP-IgG) (secondary detection step), followed by 3,3'-Diaminobenzidine (DAB) for 5 minutes (chromogen visualization step), followed by <0.1% hematoxylin for 7 minutes (nuclear counterstain step). Finally, a cover slip is attached using mounting medium. In other embodiments, other options can be employed.

In some embodiments, PR can be detected by a number of primary antibodies from a number of different manufacturers, and most produce adequate results. In some embodiments, mouse monoclonal 1A6 and rabbit monoclonal SP2 can be used from Novocastra and Lab Vision. Other options include mouse monoclonals PgR1294, 16, 1A6, 1E2, Ab-8, Ab-9, hPRa2, hPRa3, and PR88; rabbit monoclonals SP2, SP42, Y85, and EP2; and rabbit polyclonal A0097 (Dako), as well as many others, from manufacturers like Dako (Agilent), Novocastra (Leica), Ventana Medical Systems (Roche), Cell Marque (Sigma-Aldrich), Lab Vision (Thermo Scientific), BioGenex, Biocare, and Epitomics. In some embodiments, other options can be employed.

In some embodiments, high pH epitope retrieval (pH 9) can be been done in Tris-EDTA buffer with microwave heating. The titer of each lot of Dako PgR 636 antibody can be adjusted to a reference lot by the manufacturer to ensure consistent staining performance at the same dilution factor, and the 1:50 dilution used in the above example is suggested by the manufacturer. However, a range of dilutions can be used (e.g., 1:10 through 1:500) with similar performance. Alternative dilutions can be optimal with other antibody preparations, and for situations, some preparations are provided pre-diluted (ready to use). In some embodiments, other options can be employed.

PR Scoring

In some embodiments, any technique for PR scoring can be used, as long as it is adequate to observe the degree of PR fluctuation provided and described herein.

In some embodiments, PR status is determined from the IHC stained slide based upon the percentage of DCIS tumor cells with nuclear signal. In some embodiments, all areas of the tissue section containing DCIS can be evaluated to arrive at the percentage. In some embodiments, at least three DCIS-containing ducts or 1 mm of DCIS tissue can be employed to score the markers.

In some embodiments, the intensity of the nuclear signal can be reported as weak (1+), moderate (2+), or strong (3+). The intensity is the average intensity of the DCIS tumor cell nuclei with signal over the entire tissue section relative to the intensity of positive controls run with the same staining batch. In some embodiments, selection of the DCIS regions to be scored and/or the scoring are conducted manually by a pathologist and/or automatically using a computer on scanned images of the slide.

In some embodiments, a DCIS with less than 10% of tumor cells with nuclear signal can be considered negative, whereas DCIS with greater than 10% of tumor cells with nuclear signal can be considered positive, when assayed by the system or examples described herein. In some embodiments, the sample is only considered negative in the presence of appropriately stained extrinsic and internal controls. In some embodiments, any specimen lacking internal control elements (normal breast ductal epithelium) that is negative should be reported as uninterpretable (rather than as negative) and repeated using another tumor specimen from the same or an alternative tumor block.

In some embodiments, alternative thresholds can be applied (e.g., 0% vs. >0%, <1% vs. ≥1%, ≤1% vs. >1%, <5% vs. ≥5%, ≤5% vs. >5%, <10% vs. ≥10%, <15% vs. ≥15%, ≤15% vs. >15%, <20% vs. ≥20%, <20% vs. >20%, <25% vs. ≥25%, ≤25% vs. >25%, <30% vs. ≥30%, etc. and other thresholds), based upon the technique employed for staining and/or analysis. In some embodiments, alternative techniques and/or scoring methods can be used for detection, which can result in a corresponding, but different cutoff range for high and/or low risk. For such situations, the ranges provided herein for the present technique can be correlated to the other technique (for the "corresponding value") by analyzing the same sample (or two samples from a same DCIS sample) by the two different techniques and identifying them as being equivalent to one another. Alternative scoring methods, such as the Allred scoring system, immunoscores, and others that combine the percentage and intensity scoring elements also show effectiveness.

In some embodiments, PR scoring can be as follows: negative is less than 5 percent positive by percentage scoring for IHC; positive is greater than 10 percent positive by percentage scoring for IHC. In some embodiments, the difference in percent between positive and negative can be compressed, such that any sample is either positive or negative. In some embodiments, the difference between positive and negative can be dropped or ignored, if the sample falls within the range. In some embodiments, any of the values between positive and negative can be selected as the absolute distinguishing line between positive and negative (e.g., 5, 6, 7, 8, 9, or 10).

In some embodiments, FOXA1 scoring can be as follows: negative is less than a 100 immunoscore by (intensity times percentage) scoring for IHC; positive is greater than a 100 immonoscore by (intensity times percentage) scoring for IHC. In some embodiments, the difference in percent between positive and negative (100) can be compressed, such that any sample is either positive or negative. In some embodiments, the difference between positive and negative can be dropped or ignored, if the sample falls within the range. In some embodiments, any of the values between positive and negative can be selected as the absolute distinguishing line between positive and negative (e.g., 100 or lower is negative vs. 100 or higher is positive).

In some embodiments, SIAH2 scoring can be as follows: negative is less than 10 percent positive by percentage scoring for IHC; positive is greater than 20 percent positive by percentage scoring for IHC. In some embodiments, the difference in percent between positive and negative can be compressed, such that any sample is either positive or negative. In some embodiments, the difference between positive and negative can be dropped or ignored, if the sample falls within the range. In some embodiments, any of the values between positive and negative can be selected as the absolute distinguishing line between positive and negative (e.g., 10, 11, 12, 13, 14, 15, 16, 17, 18, 19, or 20).

In some embodiments, HER2 scoring can be as follows: negative is less than a 3+ score by HercepTest scoring criteria for IHC; positive is 3+ score by HercepTest scoring criteria for IHC.

In some embodiments, Ki67 scoring can be as follows: negative is less than 10 percent positive by percentage scoring for IHC; positive is greater than 15 percent scoring by percentage for IHC. In some embodiments, the difference in percent between positive and negative can be compressed, such that any sample is either positive or negative. In some embodiments, the difference between positive and negative can be dropped or ignored, if the sample falls within the range. In some embodiments, any of the values between positive and negative can be selected as the absolute distinguishing line between positive and negative (e.g., 10, 11, 12, 13, 14, or 15).

In some embodiments, p16 scoring can be as follows: negative is less than 20 percent positive by percentage scoring for IHC; positive is greater than 25 percent positive by percentage scoring for IHC. In some embodiments, the difference in percent between positive and negative can be compressed, such that any sample is either positive or negative. In some embodiments, the difference between positive and negative can be dropped or ignored, if the sample falls within the range. In some embodiments, any of the values between positive and negative can be selected as the absolute distinguishing line between positive and negative (e.g., 20, 21, 22, 23, 24, or 25).

In some embodiments, COX-2 scoring can be as follows: negative is less than 6 by Allred Scoring Criteria for COX-2 for IHC; positive is greater than 6 by Allred Scoring Criteria for COX-2 for IHC.

In some embodiments, the above ranges are for IHC assays. In some embodiments, the above ranges are for FISH assays.

In some embodiments, the positive threshold can be higher depending on marker combinations employed in concert as determined by one skilled in the art for incorporation into a specific test.

In some embodiments, SIAH2, FOXA1, and COX-2 can further be broken into sub categories of high (very high and high) and low (very low and low). This allows for finer lines to be drawn regarding risk combinations. In some embodiments, this is simplified for the analysis by having very high and high fall within the "high" grouping and very low and low fall within the "low" grouping.

HER2 Staining
HER2 IHC

In some embodiments, any technique for HER2 staining can be used, as long as it is adequate to observe the degree of HER2 fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above that above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, to assess v-erb-b2 avian erythroblastic leukemia viral oncogene homolog 2 (ERBB2; HGNC:3430; HER2 [human epidermal growth factor receptor 2]; NEU) by IHC, the following steps can be conducted with rinsing between each step on a Dako Autostainer (through the chromogen visualization step). Dewaxed and rehydrated tissue sections can be treated with Dako Peroxidase Blocking Reagent (peroxidase blocking step), followed by Dako HercepTest Epitope Retrieval Solution (10 mM citrate buffer plus detergent, pH 6) for 40 minutes in a 95° C. to 99° C. water bath (epitope retrieval step). The tissue sections can then be incubated at room temperature with pre-diluted rabbit polyclonal anti-HER2 antibody (Dako K5207) for 30 minutes (primary antibody step), followed by Dako HercepTest Visualization Reagent for 30 minutes (secondary detection step), followed by 3,3'-Diaminobenzidine (DAB) for 10 minutes (chromogen visualization step), followed by hematoxylin (nuclear counterstain step). Finally, a cover slip is attached using mounting medium.

In some embodiments, HER2 can be detected by various antibodies to HER2. In some embodiments, mouse monoclonal TAB250 and rabbit monoclonal SP3 can be used from Invitrogen and Lab Vision. Other options include mouse monoclonals CB-11, TA9145, Ab-17, 3B5, and PN2A, and rabbit monoclonals SP3, 4B5, EP1045Y, and EP3, as well as many others, from manufacturers like Dako (Agilent), Novocastra (Leica), Ventana Medical Systems (Roche), Cell Marque (Sigma-Aldrich), Lab Vision (Thermo Scientific), BioGenex, Biocare, and Epitomics.

In some embodiments, heat-induced epitope retrieval can be performed by microwave oven or water bath. In the above example, the HER2 primary antibody is provided in a pre-diluted (ready to use) format, so no dilution is performed. However, other preparations of HER2 primary antibody are available in concentrated format requiring dilution. For example, a 200 µg/ml Ig concentrate may be diluted 1:400 to 1:800 to a final Ig concentration of 0.25 to 0.50 µg/ml, or an alternative concentrate may have an optimal dilution of 1:100 with similar results achieved in a dilution range of 1:50 to 1:500.

HER2—ISH

In some embodiments, an alternative method to assess HER2 can be ISH. A fluorescent ISH (FISH) assay using a Vysis PathVysion HER-2 DNA Probe Kit (Abbott Molecular) can include the following steps with rinsing between each step. The dewaxed tissue section can be treated with 0.2N HCl for 20 minutes and then Vysis Pretreatment Solution (1 N sodium isothiocyanate) for 30-60 minutes at 80° C. (pretreatment step), followed by Vysis Protease Solution for 10-60 minutes at 37° C. (protease step), followed by 10% neutral buffered formalin (fixation step), followed by a series of increasing concentration alcohol solutions (dehydration step).

In some embodiments, a DNA probe mixture is applied to the tissue section under a sealed coverslip. The mixture contains a Locus Specific Identifier for HER-2 (a 190-Kb Spectrum Orange directly-labeled, fluorescent DNA probe specific for the HER-2 gene locus at 1711.2-q12) and a Chromosome Enumeration Probe for chromosome 17 (CEP17; a 5.4 Kb Spectrum Green directly-labeled, fluorescent DNA probe specific for the alpha satellite DNA sequence at the centromeric region of chromosome 17 at 17p11.1-q11.1), as well as unlabeled blocking DNA to suppress sequences contained within the target loci that are common to other chromosomes. The slide is then placed into a Thermobrite instrument and subjected to a temperature of 73° C. for 5 minutes (DNA denaturation step) followed by an incubation for 14-24 hours at 37° C. (DNA hybridization step).

In some embodiments, the tissue is treated with two washes of 2× saline sodium citrate (SSC) plus 0.3% NP-40, the first for 2-5 minutes at room temperature, and the second for 2 minutes at 71-73° C. (post hybridization wash step). Finally, the nuclei are stained blue with a 4, 6 diamidino-2-phenylindole (DAPI) solution (counterstaining step).

In some embodiments, an alternative ISH method based on silver deposition (SISH; Ventana Medical Systems Inform HER2 kit) can be used according to manufacturer instructions with substantially equivalent results. In some embodiments, other HER2 ISH methods, for example chromogenic ISH (CISH), can also be employed.

HER2 Scoring—HER2 IHC Scoring

In some embodiments, any technique for HER2 scoring can be used, as long as it is adequate to observe the degree of HER2 fluctuation provided and described herein.

In some embodiments, HER2 status is determined from the IHC stained slide according to College of American Pathologists-American Society of Clinical Oncology (CAP-ASCO) guidelines (Wolff et al. J Clin Oncol 31:3997, 2013) with modification for scoring on intraductal tumor cells. HER2 scores of 0-3+ are defined as follows: 0 is defined by no staining observed or membrane staining that is incomplete and is faint/barely perceptible and within ≤10% of the tumor cells. 1+ is defined by incomplete membrane staining that is faint/barely perceptible and within >10% of the tumor cells. 2+ is defined by circumferential membrane staining that is incomplete and/or weak/moderate (observed in a homogeneous and contiguous population) and within >10% of the tumor cells, or complete and circumferential membrane staining that is intense and within ≤10% of the tumor cells. 3+ is defined by circumferential membrane staining that is complete and intense (observed in a homogeneous and contiguous population and within >10% of the tumor cells, readily appreciated using a low power objective).

In some embodiments, selection of the DCIS regions to be scored and/or the scoring are conducted manually by a pathologist and/or automatically using a computer on scanned images of the slide. In some embodiments, results of 0, 1+, or 2+ are considered negative, and 3+ is considered positive. In some embodiments, 2+ results could be considered equivocal, triggering a HER2 ISH assay to determine status through quantitation of HER2 gene amplification (amplified patients are positive). In some embodiments, HER2 IHC could be completely replaced by a HER2 ISH assay. Both of these alternative approaches have shown utility in related studies.

HER2 ISH Scoring

In some embodiments, HER2 status is determined from a FISH stained slide by counting the orange HER2 and green CEP17 signals in a minimum of 20 DCIS cell nuclei and then calculating the ratio. The DCIS is considered HER2 non-amplified (negative) when there is an equal number of orange and green signals or the ratio of Orange to green is less than 2.0 with an average HER2 copy number per cell of less than 4.0. The DCIS is considered HER2 amplified (positive) when the ratio of orange to green signals is greater than 2.0. Cells are also considered amplified (positive) when the ratio of orange to green signals is less than 2.0 with an average HER2 copy number per cell greater than or equal to 6.0. When the ratio of orange to green signals is less than 2.0 with an average HER2 copy number per cell of greater than or equal to 4.0 and less than 6.0, 20 additional cells are counted, and the ratio is re-calculated for all 40 cells, and the threshold of <2.0 (negative) vs. ≥2.0 (positive) is applied.

Ki-67 Staining

In some embodiments, any technique for Ki-67 staining can be used, as long as it is adequate to observe the degree of Ki-67 fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above that above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, Ki-67 (MKI67; MIB-1; HGNC: 7107) levels can be assessed by IHC, a Leica BOND-MAX automated staining instrument is used to conduct the following steps with rinsing between each step. In some embodiments, dewaxed and rehydrated tissue sections are treated with Novocastra Peroxide Block (3-4% hydrogen peroxide) (peroxidase blocking step), followed by Novocastra Bond Epitope Retrieval Solution 2 (based on a 10 mM Tris Base and 1 mM ethylenediaminetetraacetic acid [EDTA] buffer plus 0.05% Tween 20, pH 9.0 solution) for 30 minutes at 95° C. to 100° C. (epitope retrieval step). In some embodiments, the tissue sections are then incubated at room temperature with mouse monoclonal antibody MIB-1 (Dako M7240) diluted 1:50 in Novocastra Primary Antibody Diluent for 30 minutes (primary antibody step), followed by Novocastra Post Primary solution for 15 minutes (rabbit anti-mouse IgG to introduce IgG linkers), followed by Novocastra Bond Refine Polymer for 15 minutes (anti-rabbit poly-HRP-IgG) (secondary detection step), followed by 3,3'-Diaminobenzidine (DAB) for 5 minutes (chromogen visualization step), followed by <0.1% hematoxylin for 7 minutes (nuclear counterstain step). Finally, a cover slip is attached using mounting medium.

In some embodiments, Ki-67 can be detected by any Ki-67 specific antibody. In some embodiments, the antibody can be mouse monoclonals MM1, K-2; 7B11, BGX-297, Ki88, Ki-S5, and DVB-2; rabbit monoclonals SP6, 30-9, EPR3611; and rabbit polyclonal NCL-Ki67p, as well as many others, from manufacturers like Dako (Agilent), Novocastra (Leica), Ventana Medical Systems (Roche), Cell Marque (Sigma-Aldrich), Lab Vision (Thermo Scientific), BioGenex, and Biocare.

In some embodiments, a dilution of 1:50 is used for Dako MIB-1 antibody, although other dilutions, e.g., 1:75 to 1:150, can be used, including dilutions in the range of 1:40 to 1:600. Similarly, other antibody manufacturers report recommended dilutions in the range of 1:100 to 1:200 for their antibody preparations, and some preparations are provided pre-diluted (ready to use).

Ki-67 Scoring

In some embodiments, any technique for Ki-67 scoring can be used, as long as it is adequate to observe the degree of Ki-67 fluctuation provided and described herein.

In some embodiments, Ki-67 status is determined from the IHC stained slide based upon the percentage of DCIS tumor cells with nuclear signal. In some embodiments, all areas of the tissue section containing DCIS are evaluated to arrive at the percentage. In some embodiments, at least three DCIS-containing ducts or 1 mm of DCIS tissue are used to score the markers. In some embodiments, the intensity of the signal is also reported as weak (1+), moderate (2+), or strong (3+). In some embodiments, the intensity is the average intensity of the DCIS tumor cell nuclei with signal over the entire tissue section. In some embodiments, selection of the DCIS regions to be scored and/or the scoring are conducted manually by a pathologist and/or automatically using a computer on scanned images of the slide.

In some embodiments, DCIS with less than 10% of tumor cells with nuclear signal is considered negative, whereas DCIS with greater than 10% of tumor cells with nuclear signal is considered positive. The sample is only considered negative in the presence of an appropriately stained positive control.

In some embodiments, alternative thresholds (e.g., 0% vs. >0%, <1% vs. ≥1%, ≤1% vs. >1%, <5% vs. ≥5%, ≤5% vs. >5%, <10% vs. ≥10%, <15% vs. ≥15%, ≤15% vs. >15%, <20% vs. ≥20%, ≤20% vs. >20%, <25% vs. ≥25%, ≤25% vs. >25%, <30% vs. ≥30%, etc. can be employed based upon the technique employed for staining and/or analysis. In some embodiments, alternative techniques and/or scoring methods can be used for detection, which can result in a corresponding, but different cutoff range for high and/or low risk. For such situations, the ranges provided herein for the present technique can be correlated to the other technique (for the "corresponding value") by analyzing the same sample (or two samples from a same DCIS sample) by the two different techniques and identifying them as being equivalent to one another. Alternative scoring methods, such as the Allred scoring system, immunoscores, and others that combine the percentage and intensity scoring elements also show effectiveness.

p16/INK4A Staining

In some embodiments, any technique for p16 staining can be used, as long as it is adequate to observe the degree of p16 fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above that above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, to assess the p16 isoform of cyclin-dependent kinase inhibitor 2A (p16/INK4A; CDKN2A; MTS1; HGNC:1787) by IHC, a Leica BOND-MAX automated staining instrument can be used to conduct the following steps with rinsing between each step. In some embodiments, it can be dewaxed and rehydrated tissue sections are treated with Novocastra Peroxide Block (3-4% hydrogen peroxide) (peroxidase blocking step), followed by Novocastra Bond Epitope Retrieval Solution 2 (based on a 10 mM Tris Base and 1 mM EDTA buffer plus 0.05% Tween 20, pH 9.0 solution) for 30 minutes at 95° C. to 100° C. (epitope retrieval step). The tissue sections can then be incubated at room temperature with pre-diluted mouse monoclonal antibody E6H4 (Ventana Medical Systems CINtec p16 Histology Kit) for 30 minutes (primary antibody step), followed by Novocastra Post Primary solution for 15 minutes (rabbit anti-mouse IgG to introduce IgG linkers), followed by Novocastra Bond Refine Polymer for 15 minutes (anti-rabbit poly-HRP-IgG) (secondary detection step), followed by 3,3'-Diaminobenzidine (DAB) for 5 minutes (chromogen visualization step), followed by <0.1% hematoxylin for 7 minutes (nuclear counterstain step). In some embodiments, a cover slip is attached using mounting medium.

In some embodiments, p16/INK4A can be detected by a primary antibody. In some embodiments, mouse monoclonal DCS-50.1/A7 (Neomarkers) can be used. In some embodiments, mouse monoclonals 6H12, JC8, 16PO4; 16PO7, and G175-405 and rabbit monoclonal EPR1473, as well as others can be used. In some embodiments, the p16/INK4A primary antibody is provided in a pre-diluted (ready to use) format, so no dilution is performed. However, other preparations of p16/INK4A primary antibody are available in concentrated format, and dilutions are recommended by the manufacturers in a range of 1:75 to 1:500 or even 1:25 to 1:800, depending on the specific protocol.

p16/INK4A Scoring

In some embodiments, any technique for p16 scoring can be used, as long as it is adequate to observe the degree of p16 fluctuation provided and described herein.

In some embodiments, p16/INK4A status is determined from the IHC stained slide based upon the percentage of DCIS tumor cells with nuclear signal, qualified by the intensity of the signal. In some embodiments, the intensity of the signal is reported as weak (1+), moderate (2+), or strong (3+). In some embodiments, the intensity is the average intensity of the DCIS tumor cell nuclei with signal over the entire tissue section relative to the intensity of positive controls run with the same staining batch. In some embodiments, cells with nuclear signal of at least intermediate (2+) intensity are considered positive. In some embodiments, cells with absent or weak (1+) staining are considered negative. In some embodiments, all areas of the tissue section containing DCIS are evaluated to arrive at the percentage. In some embodiments, at least three DCIS-containing ducts or 1 mm of DCIS tissue can be used to score the markers. In some embodiments, selection of the DCIS regions to be scored and/or the scoring are conducted manually by a pathologist and/or automatically using a computer on scanned images of the slide.

In some embodiments, DCIS with less than or equal to 25% of tumor cells with nuclear signal of at least moderate intensity is considered negative, whereas DCIS with greater than 25% of tumor cells with nuclear signal of at least moderate intensity is considered positive. The sample is only considered negative in the presence of an appropriately stained positive control. Alternative thresholds (e.g., <20% vs. ≥20%, ≤20% vs. >20%, <25% vs. ≥25%, <30% vs. ≥30%, ≤30% vs. >30%, <40% vs. ≥40%, etc. and other thresholds) can be employed based upon the technique employed for staining and/or analysis. In some embodiments, alternative techniques and/or scoring methods can be used for detection, which can result in a corresponding, but different cutoff range for high and/or low risk. For such situations, the ranges provided herein for the present techniques can be correlated to the other technique (for the "corresponding value") by analyzing the same sample (or two samples from a same DCIS sample) by the two different techniques and identifying them as being equivalent to one another. Alternative scoring methods, such as the Allred scoring system, immunoscores, and others that combine the percentage and intensity scoring elements also show effectiveness.

The staining pattern of p16/INK4A can be nuclear and cytoplasmic and is often heterogeneous in nature. In addition, p16/INK4A staining can be present in both the DCIS tumor cells and the surrounding stromal cells.

COX-2 Staining

In some embodiments, any technique for COX-2 staining can be used, as long as it is adequate to observe the degree of COX-2 fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above that above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, prostaglandin-endoperoxide synthase 2 (PTGS2; cyclooxygenase-2 [COX-2]; HGNC:9605) can be assessed by IHC; a Leica BOND-MAX automated staining instrument is used to conduct the following steps with rinsing between each step. In some embodiments, dewaxed and rehydrated tissue sections are treated with Novocastra Peroxide Block (3-4% hydrogen peroxide) (peroxidase blocking step), followed by Novocastra Bond Epitope Retrieval Solution 1 (based on a 10 mM sodium citrate buffer plus 0.05% Tween 20, pH 6.0 solution) for 30 minutes at 95° C. to 100° C. (epitope retrieval step). In some embodiments, the tissue sections are then incubated at room temperature with rabbit monoclonal antibody SP21 (Cell Marque 240R-16) diluted 1:50 in Novocastra Primary Antibody Diluent for 30 minutes (primary antibody step), followed by Novocastra Bond Refine Polymer for 15 minutes (anti-rabbit poly-HRP-IgG) (secondary detection step), followed by 3,3'-Diaminobenzidine (DAB) for 5 minutes (chromogen visualization step), followed by <0.1% hematoxylin for 7 minutes (nuclear counterstain step). Finally, a cover slip is attached using mounting medium.

In some embodiments, COX-2 can be detected by primary antibodies. In some embodiments, mouse monoclonal CX-294 (Dako) can be used. In some embodiments, mouse monoclonal 4H12 (Novocastra) and rabbit monoclonal SP21 from manufacturers like Ventana Medical Systems (Roche), Cell Marque (Sigma-Aldrich), Lab Vision (Thermo Scientific), and Biocare can be used.

In some embodiments, a dilution of 1:50 can be used for Cell Marque SP21 antibody. In some embodiments, a dilution of 1:100 to 1:500, or in the range of 1:50 to 1:500, 1:50 to 1:200 can be used. In addition, some preparations are provided in pre-diluted (ready to use) form.

COX-2 Scoring

In some embodiments, any technique for COX-2 scoring can be used, as long as it is adequate to observe the degree of COX-2 fluctuation provided and described herein.

In some embodiments, COX-2 status can be determined from the IHC stained slide based upon the percentage of DCIS tumor cells with cytoplasmic signal and the intensity of the signal, in the form of an Allred score. In some embodiments, the intensity is reported as absent (0), weak (1), intermediate (2), or strong (3) and represents the average signal intensity over the entire tissue section relative to the intensity of positive controls run with the same staining batch. In some embodiments, the percentage is converted to a proportion score as follows: 0, 0% positive; 1, ≤1% positive; 2, >1-10% positive; 3, 11-33% positive; 4, 34-66% positive; 5, 67-100% positive. The Allred score is the sum of the intensity and proportion scores on a scale of 0-8.

In some embodiments, all areas of the tissue section containing DCIS are evaluated. In some embodiments, at least three DCIS-containing ducts or 1 mm of DCIS tissue is employed to score the markers. Selection of the DCIS regions to be scored and/or the scoring can be conducted manually by a pathologist and/or automatically using a computer on scanned images of the slide.

In some embodiments, a DCIS with an Allred score 0 to 6 is considered negative, whereas DCIS with an Allred score of 7 or 8 is considered positive. In some embodiments, the sample is considered negative in the presence of an appropriately stained positive control. In some embodiments, alternative techniques and/or scoring methods can be used for detection, which can result in a corresponding, but different cutoff range for high and/or low risk. For such situations, the ranges provided herein for the present techniques can be correlated to the other technique (for the "corresponding value") by analyzing the same sample (or two samples from a same DCIS sample) by the two different techniques and identifying them as being equivalent to one another. In some embodiments, an alternative scoring method, such as the Allred scoring system, immunoscores, and others that combine the percentage and intensity scoring elements also show effectiveness.

FOXA1 Staining

In some embodiments, any technique for FOXA1 staining can be used, as long as it is adequate to observe the degree of FOXA1 fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above that above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, to assess forkhead box A1 (FOXA1; HGNC:5021) by IHC, a Leica BOND-MAX automated staining instrument can be used to conduct the following processes with rinsing between each step. In some embodiments, dewaxed and rehydrated tissue sections can be treated with Novocastra Peroxide Block (3-4% hydrogen peroxide) (peroxidase blocking step), followed by Novocastra Bond Epitope Retrieval Solution 2 (based on a 10 mM Tris Base and 1 mM ethylenediaminetetraacetic acid [EDTA] buffer plus 0.05% Tween 20, pH 9.0 solution) for 30 minutes at 95° C. to 100° C. (epitope retrieval step). The tissue sections can then be incubated at room temperature with mouse monoclonal antibody 2F83 (Cell Marque 405M-16) diluted 1:25 in Novocastra Primary Antibody Diluent for 30 minutes (primary antibody step), followed by Novocastra Post Primary solution for 15 minutes (rabbit anti-mouse IgG to introduce IgG linkers), followed by Novocastra Refine Polymer for 15 minutes (anti-rabbit poly-HRP-IgG) (secondary detection step), followed by 3,3'-Diaminobenzidine (DAB) for 5 minutes (chromogen visualization step), followed by <0.1% hematoxylin for 7 minutes (nuclear counterstain step). A cover slip can be attached using mounting medium.

In some embodiments, FOXA1 mouse monoclonal antibody 2F83 from Abcam can be used at a dilution of 1:450 (or, for example, 1:2,000) with effective results or used at a dilution of 1:25 (manufacturer recommended starting dilution range of 1:25 to 1:100, based on an initial estimated Ig concentration of 2.5 to 25.0 µg/ml with a final estimated optimal Ig concentration range of 0.1 to 1.0 µg/ml). In some embodiments, mouse monoclonal antibodies can include 2F83, 3A8, 1B1, 2D7, 3C1, and 4F6, and rabbit monoclonals SP88 and EPR10881 from Thermo Scientific, Spring Bioscience, Epitomics, Millipore, and a variety of other manufacturers. Various dilutions can be used with other antibody preparations (e.g., Millipore recommends a 1:500 dilution of their 1 mg/ml version of 2F83, and Thermo Scientific recommends a 1:20 to 1:200 dilution of their 1 mg/ml preparation of clone 3A8). And some FOXA1 antibody preparations are provided pre-diluted (ready to use).

FOXA1 Scoring

In some embodiments, any technique for FOXA1 scoring can be used, as long as it is adequate to observe the degree of FOXA1 fluctuation provided and described herein.

In some embodiments, FOXA1 status can be determined from the IHC stained slide based upon the percentage of DCIS tumor cells with nuclear signal and the intensity of the signal, in the form of an immunoscore. The intensity can be reported as absent (0), weak (1), intermediate (2), or strong (3) and can represent the average signal intensity over the entire tissue section relative to the intensity of positive controls run with the same staining batch. In some embodiments, the immunoscore can be the product of the intensity and percentage scores on a scale of 0-300.

In some embodiments, all areas of the tissue section containing DCIS are evaluated. In some embodiments, three DCIS-containing ducts or 1 mm of DCIS tissue is used to score the markers. Selection of the DCIS regions to be scored and/or the scoring can be conducted manually by a pathologist and/or automatically using a computer on scanned images of the slide.

In some embodiments, DCIS with an immunoscore less than 100 is considered FOXA1 low, DCIS with an immunoscore between 100 and 250 is considered FOXA1 intermediate, and DCIS with an immunoscore greater than 250 is considered FOXA1 high. Alternative lower (e.g., 40 or 150) and/or upper (e.g., 150 or 250) thresholds, as well as alternative scoring methods, also show utility. In addition, the utility can vary based on the outcome being predicted (i.e., a DCIS or invasive event in the ipsilateral breast). In some embodiments, FOXA1 is merely treated as either being "negative" (100 or lower) or positive (greater than 100).

In some embodiments, alternative techniques and/or scoring methods can be used for detection, which can result in a corresponding, but different cutoff range for high and/or low risk. For such situations, the ranges provided herein for the present techniques can be correlated to the other technique (for the "corresponding value") by analyzing the same sample (or two samples from a same DCIS sample) by the two different techniques and identifying them as being equivalent to one another. In some embodiments, an alternative scoring method, such as the Allred scoring system, immunoscores, and others that combine the percentage and intensity scoring elements also show effectiveness.

SIAH2 Staining

In some embodiments, any technique for SIAH2 staining can be used, as long as it is adequate to observe the degree of SIAH2 fluctuation provided and described herein. In some embodiments, protein levels can be checked. In some embodiments, mRNA levels can be checked. In some embodiments, DNA levels can be checked. In some embodiments, both protein and mRNA levels can be checked. An elevated level can be a level above a control or standardized level, for example, a level in a non-DCIS sample. Similarly, a lowered level can be a level below a control or standardized level, for example, a level in a non-DCIS sample. In some embodiments, a "positive" or "elevated" result is one that is above a "negative" or "lowered" result (in the context of scoring).

In some embodiments, to assess SIAH2 E3 ubiquitin protein ligase 2 (SIAH2; seven in absentia [*Drosophila*] homolog 2; HGNC:10858) by IHC, a Leica BOND-MAX automated staining instrument can be used to conduct the following steps with rinsing between each step. In some embodiments, dewaxed and rehydrated tissue sections are treated with Novocastra Peroxide Block (3-4% hydrogen peroxide) (peroxidase blocking step), followed by Novocastra Bond Epitope Retrieval Solution 1 (based on a 10 mM sodium citrate buffer plus 0.05% Tween 20, pH 6.0 solution) for 30 minutes at 95° C. to 100° C. (epitope retrieval step). In some embodiments, the tissue sections are then incubated at room temperature with mouse monoclonal antibody 24E6H3 (Santa Cruz Biotechnology sc-81787) diluted 1:200 in Novocastra Primary Antibody Diluent for 30 minutes (primary antibody step), followed by Novocastra Post Primary solution for 15 minutes (rabbit anti-mouse to introduce IgG linkers), followed by Novocastra Bond Refine Polymer for 15 minutes (anti-rabbit poly-HRP-IgG) (secondary detection step), followed by 3,3'-Diaminobenzidine (DAB) for 5 minutes (chromogen visualization step), followed by <0.1% hematoxylin for 7 minutes (nuclear counterstain step). In some embodiments, a cover slip is attached using mounting medium.

In some embodiments, epitope retrieval can be done at a higher pH (8.0) in EDTA-containing buffer in either a 98° C. water bath or steam chamber with both mouse monoclonal antibody 24E6H3 and its parental clone 24E6 in related studies. In some embodiments, alternative antibodies can be used, including those from Novus Biologicals. Different dilutions can be used with different preparations of these antibody, including dilutions within the range of 1:40 to 1:200. In some embodiments, other primary antibodies can be used, such as mouse monoclonal 35F7I4 (Creative Diagnostics), which works for IHC (recommended dilution of 1:40 to 1:50), and mouse monoclonals 1F5, 2G6, and SIAH2-369 (available from Abnova, Epigentek, US Biologicals, Sigma-Aldrich, and Creative Diagnostics).

SIAH2 Scoring

In some embodiments, any technique for SIAH2 scoring can be used, as long as it is adequate to observe the degree of SIAH2 fluctuation provided and described herein.

In some embodiments, SIAH2 status is determined from the IHC stained slide based upon the percentage of DCIS tumor cells with nuclear signal. In some embodiments, all areas of the tissue section containing DCIS are evaluated to arrive at the percentage. In some embodiments, at least three DCIS-containing ducts or 1 mm of DCIS tissue is used to score the markers. In some embodiments, the intensity of the signal can be reported as weak (1+), moderate (2+), or strong (3+). In some embodiments, the intensity is the average intensity of the DCIS tumor cell nuclei with signal over the entire tissue section. In some embodiments, selection of the DCIS regions to be scored and/or the scoring are conducted manually by a pathologist and/or automatically using a computer on scanned images of the slide.

In some embodiments, DCIS with less than 20% of tumor cells with nuclear signal is considered negative, whereas DCIS with greater than or equal to 20% of tumor cells with nuclear signal is considered positive.

In some embodiments, the sample is only considered negative in the presence of an appropriately stained positive control.

In some embodiments, alternative techniques and/or scoring methods can be used for detection, which can result in a corresponding, but different cutoff range for high and/or low risk. For such situations, the ranges provided herein for the noted techniques can be correlated to the other technique (for the "corresponding value") by analyzing the same sample (or two samples from a same DCIS sample) by the two different techniques and identifying them as being equivalent to one another. In some embodiments, an alternative scoring method, such as the Allred scoring system, immunoscores, and others that combine the percentage and intensity scoring elements also show effectiveness. In some embodiments, alternative thresholds (e.g., ≤20% vs. >20%, <25% vs. ≥25%, ≤25% vs. >25%, <30% vs. ≥30%, ≤30% vs. >30%, <40% vs. ≥40%, ≤40% vs. >40%, etc. and other thresholds) can be used. In some embodiments, alternative scoring methods, such as the Allred scoring system, immunoscores, and others that combine the percentage and intensity scoring elements can also be used.

Figure 3:
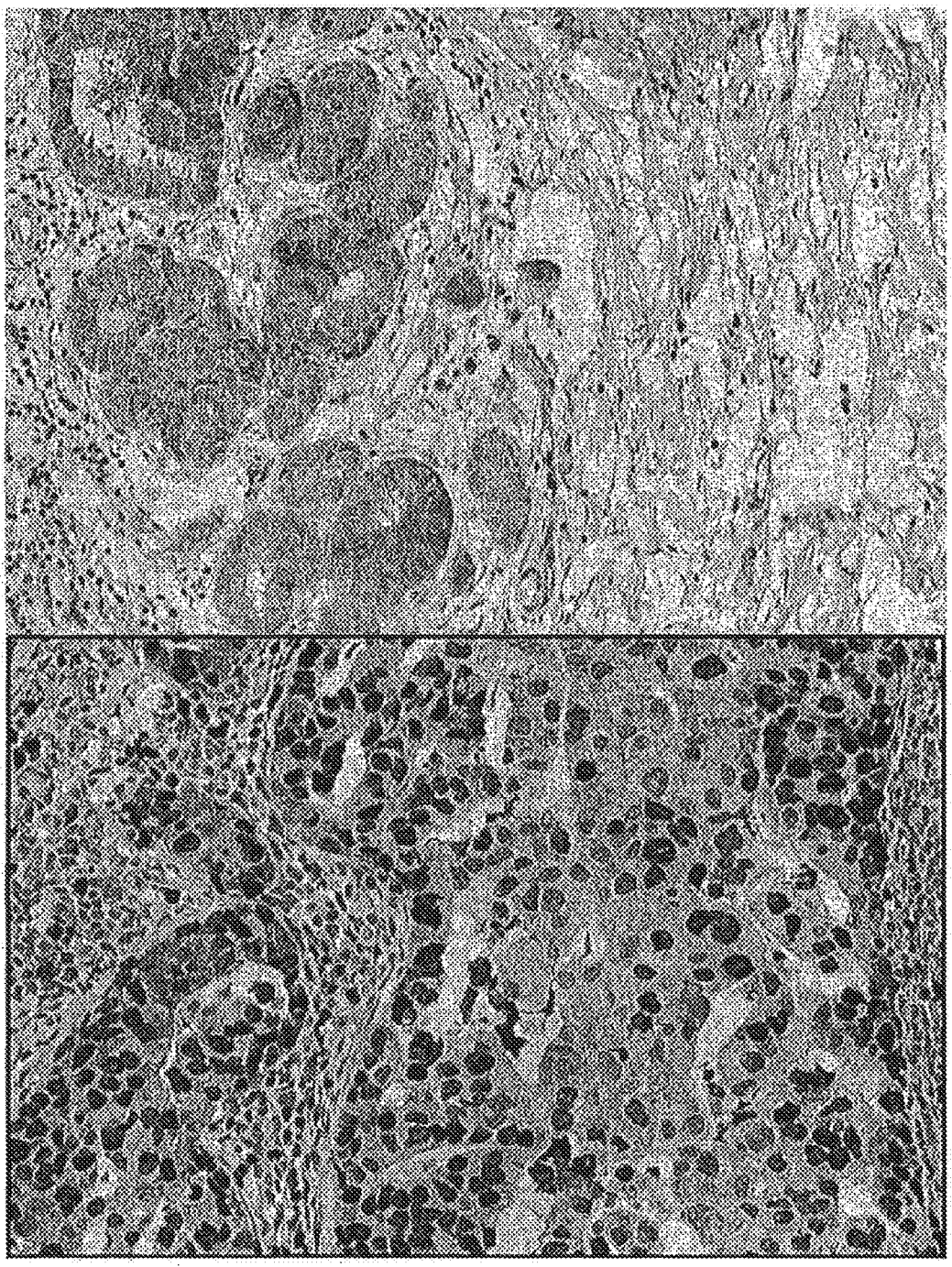
FIG. 3 depicts SIAH2 IHC assays (top, negative, on a UUH TMA; bottom, positive, on a Biomax BR8011 TMA).

An example of SIAH2 staining and scoring is presented in FIG. 3. FIG. 3 depicts SIAH2 IHC assays (top, negative, on a UUH TMA; bottom, positive, on a Biomax BR8011 TMA).

Statistical Analysis

Kaplan-Meier survival analyses can be used to estimate the proportions of patients who experienced first events (DCIS or invasive recurrence) after initial DCIS diagnosis/surgery. Hazard ratios (HR) can be determined using Cox proportional hazards analysis. At the time of first events (DCIS or invasive), patients can be censored for the other event type. Patients can also be censored if an event is detected within 6 months of surgery or on the first post-surgery mammogram, because this can be considered as persistent, rather than recurrent, disease. In some embodiments, subjects with persistent disease are excluded from the various methods provided herein.

Methods of Assessing Markers

While the above noted assaying system and scoring systems have been put forth, in some embodiments, alternative techniques and/or scoring methods can be used for detection, which can result in a corresponding, but different cutoff range for high and/or low risk. For such situations, the ranges provided herein for the present techniques can be correlated to the other technique (for the "corresponding value" of one or more of COX-2, Ki67, p16, SIAH2, FOXA1, PR, and/or HER2) by analyzing the same sample (or two samples from a same DCIS sample) by the two different techniques and identifying them as being matched or equal to one another. In some embodiments, an alternative scoring method, such as the Allred scoring system, immunoscores, and others that combine the percentage and intensity scoring elements also show effectiveness. In some embodiments, there can be a corresponding technique and/or score for one or more of COX-2, Ki67, p16, SIAH2, FOXA1, PR, and/or HER2. In some embodiments, there can be a corresponding technique for one or more of COX-2, Ki67, p16, SIAH2, FOXA1, PR, and/or HER2. In some embodiments, there can be a corresponding score for one or more of COX-2, Ki67, p16, SIAH2, FOXA1, PR, and/or HER2. As will be appreciated by one of skill in the art, these corresponding scores and/or techniques can be used for any of the embodiments provided herein, and are expressly contemplated as alternatives for each and all disclosure regarding the noted markers.

In some embodiments, protein detection assays can be used, including for example, immunohistochemistry, immunofluorescence, mass spectrometry, or others, discussed in more detail below. In some embodiments, mRNA detection assays can be used, including, for example, nucleic acid hybridization-based methods such as Northern blots, gene expression arrays, quantitative real-time polymerase chain reaction (qPCR), nCounter, in situ nucleic acid detection, etc., as well as next-generation RNA sequencing (RNA-Seq)), and others. In some embodiments, techniques to detect changes at the DNA level can be used, including, for example, polymerase chain reaction (PCR), in situ hybridization (ISH), next generation sequencing (NGS), and others as will be readily understood by those of skill in the art.

In some embodiments, while corresponding values (involving alternative scoring or alternative assays to analyze the sample) are used, the relative result (for example, high vs. low or very high vs. medium vs. low) will be maintained between the various techniques for analysis or scoring systems. Thus, scoring "high" in one system will be correlated to scoring "high" in another system, without significant complications or difficulties. Thus, various results can be ported from one system to another, as desired, as long as the levels in terms of relatively high vs low (for example) are maintained. Similarly, in some embodiments, protein levels can be used for one marker, while a second marker can be analyzed via DNA, and, for example, a third marker can be analyzed via mRNA. Thus, the nature of the molecule being tested can be altered within a test, if desired.

In some embodiments, the level of expression is determined by detecting the level of mRNA transcribed from a gene.

In some embodiments, the mRNA in the sample is first transcribed into cDNA using reverse transcriptase.

In some embodiments, the sample is subjected to an amplification reaction (e.g., using methods based on polymerase chain reaction (PCR), nucleic acid sequence-based amplification (NASBA), transcription-mediated amplification (TMA), strand displacement amplification (SDA), etc.), probe amplification (e.g., using methods based on ligase chain reaction (LCR), cleavase invader, etc.), signal amplification (e.g, using methods based on branched DNA probes [bDNA], hybrid capture, etc.), and others as will be readily understood by those of skill in the art.

In some embodiments, the mRNA is detected in the sample by hybridizing a nucleic acid probe or primer capable of selectively hybridizing to a mRNA transcript of interest, or cDNA derived therefrom, and then detecting the hybridization with a detection device or system.

In this context, the term "selective hybridization" means that hybridization of a probe or primer occurs at a higher frequency or rate, or has a higher maximum reaction velocity, than hybridization of the same probe or primer to any other nucleic acid. Preferably, the probe or primer does not hybridize to another nucleic acid at a detectable level under the reaction conditions used.

As transcripts of a gene described herein are detected using mRNA or cDNA derived therefrom, assays that detect changes in mRNA can be employed (for example, Northern hybridization, RT-PCR, NASBA, TMA or ligase chain reaction).

In some embodiments, mRNA quantitation can be carried out on gene expression array platforms, including Agilent's Bioanalyzer® system; Affymetrix' GeneChip®, GeneTitan®, or GeneAtlas® systems; and others as will be readily understood by those of skill in the art.

In some embodiments, mRNA quantitation can be carried out by real-time qPCR. Such reactions can be performed with a variety of reporters, including non-specific DNA-binding fluorochromes (e.g., SYBR® Green) or fluorescent reporter probes that selectively hybridize to the sequence of interest (e.g., TaqMan® probes). In some cases, the reaction is carried out in parallel on multiple partitions of the same sample (digital PCR). Real-time qPCR platforms include ThermoFisher Scientific/Applied Biosystems' FAST, QuantStudio, and related systems; Hologic/Gen-Probe's DTS systems; Roche/Idaho Technology's LightCycler® systems; Qiagen's Rotor-Gene® systems; Bio-Rad's CFX and related systems; and others as will be readily understood by those of skill in the art.

In some embodiments, mRNA quantitation can be carried out without a reverse-transcription or amplification step, such as NanoString's in vitro nCounter® platform, or various in situ hybridization (ISH) approaches, including paired probe ISH (e.g., RNAscope® and Quanti-Gene RNAview), single-tag multi-probe ISH (e.g., Stellaris®), or locked nucleic-acid (LNA) probes.

In some embodiments, mRNA quantitation can be carried out with RNA-Seq next-generation sequencing technologies, including sequencing by synthesis (e.g, Illumina's HiSeq® and NextSeq® systems), single-molecule real-time sequencing (e.g., Pacific Biosciences' RS systems), ion seminconductor sequencing (e.g., ThermoFisher Scientific's Ion Torrent™ systems), sequencing by ligation (e.g., ThermoFisher Scientific's SOLiD™ systems), pyrosequencing (e.g., Roche/454 Life Sciences), and others as will be readily understood by those of skill in the art.

Methods of RT-PCR include, for example, in Dieffenbach (ed) and Dveksler (ed) (In: PCR Primer: A Laboratory Manual, Cold Spring Harbour Laboratories, N Y, 1995). Essentially, this method comprises performing a PCR reaction using cDNA produced by reverse transcribing mRNA from a cell using a reverse transcriptase. Methods of PCR described supra are to be taken to apply mutatis mutandis to this embodiment of the invention.

Similarly PCR can be performed using cDNA. One or more of the probes or primers used in the reaction specifically hybridize to the transcript of interest.

Methods of TMA or self-sustained sequence replication (3SR) use two or more oligonucleotides that flank a target sequence, a RNA polymerase, RNase H and a reverse transcriptase. One oligonucleotide (that also comprises a RNA polymerase binding site) hybridizes to an RNA molecule that comprises the target sequence and the reverse transcriptase produces cDNA copy of this region. RNase H is used to digest the RNA in the RNA-DNA complex, and the second oligonucleotide used to produce a copy of the cDNA. The RNA polymerase is then used to produce a RNA copy of the cDNA, and the process repeated.

NASBA systems relies on the simultaneous activity of three enzymes (a reverse transcriptase, RNase H and RNA polymerase) to selectively amplify target mRNA sequences. The mRNA template is transcribed to cDNA by reverse transcription using an oligonucleotide that hybridizes to the target sequence and comprises a RNA polymerase binding site at its 5' end. The template RNA is digested with RNase H and double stranded DNA is synthesized. The RNA polymerase then produces multiple RNA copies of the cDNA and the process is repeated.

In some embodiments, a microarray can be used to determine the level of expression of one or more nucleic acids described herein. Such a method allows for the detection of a number of different nucleic acids, thereby providing a multi-analyte test and improving the sensitivity and/or accuracy of the diagnostic assay of the invention.

In some embodiments, the level of expression is determined by detecting the level of a protein encoded by a nucleic acid within a gene described herein.

In this respect, the embodiments are not necessarily limited to the detection of a protein comprising the specific amino acid sequence recited herein. Rather, the present invention encompasses the detection of variant sequences (e.g., having at least about 80% or 90% or 95% or 98% amino acid sequence identity) or the detection of an immunogenic fragment or epitope of said protein.

The amount, level and/or presence of a polypeptide can be determined using any of a variety of techniques known to the skilled artisan such as, for example, a technique selected from the group of, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In some embodiments, the assay used to determine the amount or level of a protein is a semi-quantitative assay. In some embodiments, the assay used to determine the amount or level of a protein in a quantitative assay. As will be apparent from the preceding description, such an assay may involve the use of a suitable control, e.g. from a normal individual or matched normal control.

In some embodiments, standard solid-phase ELISA or FLISA formats can be useful in determining the concentration of a protein from a variety of samples.

In one form such an assay involves immobilizing a biological sample onto a solid matrix, such as, for example a polystyrene or polycarbonate microwell or dipstick, a membrane, or a glass support (e.g. a glass slide). An antibody that specifically binds to a protein described herein is brought into direct contact with the immobilized biological sample, and forms a direct bond with any of its target protein present in said sample. This antibody is generally labeled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or beta-galactosidase) in the case of an ELISA, or alternatively a second labeled antibody can be used that binds to the first antibody. Following washing to remove any unbound antibody the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal) in the case of an enzymatic label.

In some embodiments, an ELISA or FLISA comprises immobilizing an antibody or ligand that specifically binds a protein described supra on a solid matrix, such as, for example, a membrane, a polystyrene or polycarbonate microwell, a polystyrene or polycarbonate dipstick or a glass support. A sample is then brought into physical relation with said antibody, and the polypeptide is bound or 'captured'. The bound protein is then detected using a labeled antibody. For example, a labeled antibody that binds to an epitope that is distinct from the first (capture) antibody is used to detect the captured protein. Alternatively, a third labeled antibody can be used that binds the second (detecting) antibody.

In some embodiments, the presence or level of a protein is detected in a body fluid using, for example, a biosensor instrument (e.g., BIAcore™, Pharmacia Biosensor, Piscataway, N.J.). In such an assay, an antibody or ligand that specifically binds a protein is immobilized onto the surface of a receptor chip. For example, the antibody or ligand is covalently attached to dextran fibers that are attached to gold film within the flow cell of the biosensor device. A test sample is passed through the cell. Any antigen present in the body fluid sample, binds to the immobilized antibody or ligand, causing a change in the refractive index of the medium over the gold film, which is detected as a change in surface plasmon resonance of the gold film.

In some embodiments, the presence or level of a protein or a fragment or epitope thereof is detected using a protein and/or antibody chip. To produce such a chip, an antibody or ligand that binds to the antigen of interest is bound to a solid support such as, for example glass, polycarbonate, polytetrafluoroethylene, polystyrene, silicon oxide, gold or silicon nitride. This immobilization is either direct (e.g. by covalent linkage, such as, for example, Schiff's base formation, disulfide linkage, or amide or urea bond formation) or indirect.

To bind a protein to a solid support it is often useful to treat the solid support so as to create chemically reactive groups on the surface, such as, for example, with an aldehyde-containing silane reagent or the calixcrown derivatives described in Lee et al, Proteomics, 3: 2289-2304, 2003. A streptavidin chip is also useful for capturing proteins and/or peptides and/or nucleic acid and/or cells that have been conjugated with biotin (e.g. as described in Pavlickova et al., Biotechniques, 34: 124-130, 2003). Alternatively, a peptide is captured on a microfabricated polyacrylamide gel pad and accelerated into the gel using microelectrophoresis as described in, Arenkov et al. Anal. Biochem. 278:123-131, 2000.

Other assay formats are also contemplated, such as flow-through immunoassays (PCT/AU2002/01684), a lateral flow immunoassay (US20040228761, US20040248322 or US20040265926), a fluorescence polarization immunoassay (FPIA) (U.S. Pat. Nos. 4,593,089, 4,492,762, 4,668,640, and 4,751,190), a homogeneous microparticles immunoassay ("HMI") (e.g., U.S. Pat. Nos. 5,571,728, 4,847,209, 6,514,770, and 6,248,597) or a chemiluminescent microparticle immunoassay ("CMIA"). The contents of all of the patent applications and patents disclosed in this paragraph are incorporated herein by reference in their entirety. In some embodiments, mRNA can be used to assay for HER2. In some embodiments, mRNA is not used for assaying for SIAH2.

In some embodiments, "elevated risk" for DCIS is defined as that detailed in Gorringe and Fox, Ductal Carcinoma In Situ Biology, Biomarkers, and Diagnosis, Frontiers in Oncology, Vol. 71-14, October 2017, the entirety of which is hereby incorporated by reference. In some embodiments, any one or more of the conditions, markers, etc. noted in Gorringe and Fox can be used to define the elevated risk aspect provided and employed herein in initially identifying a subject as one in the elevated risk grouping, and from which one then continues on with the other testing, analysis, and/or treatment options provided herein. In some embodiments, "elevated risk" for DCIS is defined as an elevated risk under a DCISionRT analysis. In some embodiments, the DCISionRT analysis is that described in Bremer et al., "A Biologic Signature for Breast Ductal Carcinoma in situ to Predict Radiation Therapy benefit and Assess Recurrence Risk", American Association of Cancer Research, in Clinical Cancer Research, doi: 10.1158/1078-0432.CCR-18-0842, Jul. 27, 2018, the entirety is incorporated herein by reference. In some embodiments, elevated risk (for DCIS recurrence or invasive breast cancer in a subject with DCIS) is as determined by any one or more of the compositions or techniques in U.S. Pat. Pub. No. 2017/0350895, the entirety of which is hereby incorporated by reference.

Treatments By Test Results

For subjects at risk of a subsequent invasive ipsilateral breast event, then the subject may be treated with at least BCS plus radiation therapy (RT), and may receive further adjuvant therapy of at least hormone therapy (e.g., tamoxifen or an aromase inhibitor), and/or HER2 therapy (e.g., Trastuzumab). The selection of which option will depend upon whether or not the subject will respond to radiation therapy, based on the present disclosure (e.g., elevated k-ras members and/or HER2+ and SIAH+). In some embodiments, if a subject has a high likelihood of both an invasive ipsilateral breast event and a DCIS ipsilateral breast event then the subject can be treated with mastectomy and can receive further adjuvant therapy of at least hormone therapy and/or HER2 therapy, if the subject will not respond to radiation therapy (e.g., elevated k-ras pathway and/or HER2+ and SIAH+).

In some embodiments, rather than relying on standard clinical and pathologic factors to determine treatment or a risk profile to interpret, one can use a signature of biomarkers to direct performance of a therapy. This ability allows one a superior approach to therapy without having to determine therapy after interpreting a risk profile. That is, as compared to current DCIS standard of care (breast-conserving surgery (BCS) with adjuvant radiation therapy), more appropriate treatment may be given to patients according to a signature recommending treatment for patients based on a biological profile detailed and described in Tables 13-15 and included herein by example. In some embodiments, a subject is treated with BCS or frequent breast imaging for early detection of an ipsilateral breast event (watchful waiting) to reduce likelihood of a subsequent ipsilateral breast event. In some embodiments, the guided treatment is at least BCS plus radiation therapy and may include further adjuvant therapy of at least hormone therapy (e.g., tamoxifen or an aromatase inhibitor), and/or HER2 therapy (e.g., Trastuzumab) to reduce the likelihood of an invasive ipsilateral breast event. In some embodiments, if the subject is SIAH+ and HER2+ and/or has an elevated k-ras pathway, then radiation therapy is not employed and instead HER2 therapy can be employed. In some embodiments, the subject can be treated with mastectomy and can receive further adjuvant therapy of at least hormone therapy and/or HER2 therapy to reduce the likelihood that a subject/patient has an invasive ipsilateral breast event and/or a DCIS ipsilateral breast event (especially when the subject is refractory to radiation therapy).

TABLE 13

(INVASIVE RISK)

| EXAMPLE NUMBER | RISK LEVEL | COMPONENTS | TREATMENT | ALTERNATIVE TREATMENT |
|---|---|---|---|---|
| 1) | LOWER RISK | PR is POSITIVE and (AGE is LOW) | LOWER RISK TREATMENT | LOWER RISK TREATMENT |
|  | ELEVATED RISK | PR is NEGATIVE and (AGE is LOW) | MASTECTOMY | BCS + RT + ADJUVANT THERAPY |
| 2) | LOWER RISK | (PR is POSITIVE and HER2 is NEGATIVE) and (AGE is LOW) | LOWER RISK TREATMENT | LOWER RISK TREATMENT |
|  | ELEVATED RISK | (PR is NEGATIVE OR HER2 is POSITIVE) and (AGE is LOW) | MASTECTOMY | BCS + RT + ADJUVANT THERAPY |
| 3) | LOWER RISK | (PR is POSITIVE and HER2 is NEGATIVE) and (AGE is LOW) | LOWER RISK TREATMENT | LOWER RISK TREATMENT |
|  | ELEVATED RISK | (HER2 is POSITIVE) and (AGE is LOW) | BCS + RT, ADJUVANT HER2 TREATMENT | MASTECTOMY |
|  | ELEVATED RISK | (HER2 IS NEGATIVE and PR is NEGATIVE) and (AGE is LOW) | MASTECTOMY | BCS + RT |
| 4) | LOWER RISK | (SIAH2 is HIGH or HER2 is POSITIVE) and (PR is NEGATIVE) | LOWER RISK TREATMENT | LOWER RISK TREATMENT |
|  | ELEVATED RISK | (SIAH2 is LOW and HER2 is NEGATIVE) and (PR is NEGATIVE) | BCS + RT |  |
| 5) | LOWER RISK | (FOXA1 is ELEVATED or HER2 is POSITIVE) and (PR is NEGATIVE) | LOWER RISK TREATMENT | LOWER RISK TREATMENT |
|  | ELEVATED RISK | FOXA1 IS LOW and HER2 is NEGATIVE and (PR is NEGATIVE) | BCS + RT | BCS + RT |
| 6) | LOWER RISK | (SIAH2 is ELEVATED and FOXA1 is ELEVATED and HER2 is NEGATIVE) and (AGE is ELEVATED and HER2 is POSITIVE) and PR is NEGATIVE | LOWER RISK TREATMENT | LOWER RISK TREATMENT |
|  | ELEVATED RISK | (SIAH2 is LOW or FOXA1 is LOW) and HER2 is NEGATIVE and PR is NEGATIVE) or (AGE is LOW and HER2 is POSITIVE and PR is NEGATIVE) | BCS + RT | MASTECTOMY |

TABLE 13-continued

| (INVASIVE RISK) | | | | |
|---|---|---|---|---|
| 7) PR POSITIVE | LOWER RISK | (FOXA1 is LOW or HER2 is POSITIVE) and AGE ELEVATED and PR is POSITIVE | LOWER RISK TREATMENT | LOWER RISK TREATMENT |
| | ELEVATED RISK | FOXA1 is ELEVATED and HER2 is NEGATIVE) and AGE ELEVATED and PR is POSITIVE | BCS + RT | |

TABLE 13 LEGEND:

| | | |
|---|---|---|
| FOXA1 is LOW | FOXA1 ASSESSED BY IMMUNOSCORE (INTENSITY TIMES PERCENTAGE) | <150 IMMUNOSCORE |
| FOXA1 is ELEVATED | FOXA1 ASSESSED BY IMMUNOSCORE (INTENSITY TIMES PERCENTAGE) | >=150 IMMUNOSCORE |
| PR is NEGATIVE | PR ASSESSED BY PERCENTAGE | <15% |
| PR is POSITIVE | PR ASSESSED BY PERCENTAGE | >=15% |
| HER2 is NEGATIVE | HER2 ASSESSED BY IHC AS (EITHER 1+ OR 2+) OR BY FISH AS NEGATIVE OR BY SISH AS NEGATIVE; HOWEVER IF ANY OF THESE ARE POSITIVE THEN THE RESULT IS POSITIVE | HER2 IHC (1+ OR 2+), OR FISH NEG, OR SISH NEG; HOWEVER IF ANY OF THESE ARE POSITIVE THEN THE RESULT IS POSITIVE |
| HER2 is POSITIVE | HER2 ASSESSED BY IHC AS (EITHER 3+) OR BY FISH AS POSITIVE OR BY SISH AS POSITIVE HOWEVER IF ANY OF THESE ARE POSITIVE THEN THE RESULT IS POSITIVE | HER2 IHC (3+), OR FISH POS, OR SISH POS; WHERE IF ANY OF THESE ARE POSITIVE THEN THE RESULT IS POSITIVE |
| AGE is LOW | AGE assessed by patient age at diagnosis of initial DCIS | AGE <50 |
| AGE is ELEVATED | AGE assessed by patient age at diagnosis of initial DCIS | AGE >=50 |
| SIAH2 is LOW | SIAH2 ASSESSED BY IHC AS PERCENTAGE | <20 |
| SIAH2 is ELEVATED | SIAH2 ASSESSED BY IHC AS PERCENTAGE | >=30 |
| PALPABLE | The patient presented following the finding of a palpable mass in the breast or a physical exam found a palpable mass in the breast | IS PALPABLE |
| NOT PALPABLE | The patient was not found to have a palpable mass in the breast | NOT PALPABLE |

TABLE 14

| | | (DCIS RISK) | | | |
|---|---|---|---|---|---|
| EXAMPLE NUMBER | RISK LEVEL | COMPONENTS | TREATMENT | ALTERNATIVE TREATMENT | REFERENCE TABLE IN APPLICATION |
| 1) | LOWER RISK | SIAH2 is LOW and AGE is ELEVATED | LOWER DCIS RISK TREATMENT | LOWER RISK TREATMENT | 5 |
| | ELEVATED RISK | SIAH2 is ELEVATED and AGE is ELEVATED | BCS + RT | | |
| 2) | LOWER RISK | SIAH2 is LOW and AGE is ELEVATED | LOWER DCIS RISK TREATMENT | LOWER RISK TREATMENT | 3, 5 |
| | ELEVATED RISK | SIAH2 is ELEVATED and PR is POSITIVE and AGE is ELEVATED | BCS + RT + ADJUVANT HORMONE TREATMENT | BCS + RT | |
| | ELEVATED RISK | S1AH2 is ELEVATED and PR is NEGATIVE and AGE is ELEVATED | BCS + RT | | |
| 3) | LOWER RISK | SIAH2 is LOW and AGE is ELEVATED | LOWER DCIS RISK TREATMENT | LOWER RISK TREATMENT | 2, 5 |
| | ELEVATED RISK | SIAH2 is ELEVATED and HER2 is POSITIVE and AGE is ELEVATED | BCS + RT | BCS + RT + ADJUVANT TARGETED HER2 TREATMENT | |
| | ELEVATED RISK | SIAH2 is ELEVATED and HER2 is NEGATIVE and AGE is ELEVATED | BCS + RT | | |
| 4) | LOWER RISK | SIAH2 is LOW and (PR is NEGATIVE) | LOWER DCIS RISK TREATMENT | LOWER RISK TREATMENT | 4 |
| | ELEVATED RISK | SIAH2 is ELEVATED and (PR is NEGATIVE or HER2 is POSITIVE) | BCS + RT | | |
| 5) | LOWER RISK | SIAH2 is LOW and (PR is NEGATIVE) | LOWER DCIS RISK TREATMENT | LOWER RISK TREATMENT | 4 |
| | ELEVATED RISK | SIAH2 is ELEVATED and HER2 is POSITIVE | BCS + RT | BCS + RT + ADJUVANT TARGETED HER2 TREATMENT | |
| | ELEVATED RISK | SIAH2 is ELEVATED and PR is NEGATIVE and HER2 is NEGATIVE | BCS + RT | | |
| 6) | LOWER RISK | SIAH2 is LOW and (PR is NEGATIVE) | LOWER DCIS RISK TREATMENT | LOWER RISK TREATMENT | 4, 5 |
| | ELEVATED RISK | SIAH2 is ELEVATED and (PR is NEGATIVE or HER2 is | BCS + RT | | |

TABLE 14-continued

| | | (DCIS RISK) | | | |
|---|---|---|---|---|---|
| | | POSITIVE or AGE is ELEVATED) | | | |
| 7) | LOWER RISK | SIAH2 is LOW and (PR is NEGATIVE) | LOWER DCIS RISK TREATMENT | LOWER RISK TREATMENT | 4, 5 |
| | ELEVATED RISK | SIAH2 is ELEVATED and HER2 is POSITIVE | BCS + RT | BCS + RT + ADJUVANT TARGETED HER2 TREATMENT | |
| | ELEVATED RISK | SIAH2 is ELEVATED and (PR is NEGATIVE or AGE is ELEVATED) and HER2 is NEGATIVE | BCS + RT | | |
| 8) | LOWER RISK | FOXA1 is ELEVATED and (PR is POSITIVE) | LOWER DCIS RISK TREATMENT | LOWER RISK TREATMENT | 6 |
| | ELEVATED RISK | FOXA1 is LOW and PR is POSITIVE | BCS + RT | BCS + RT + ADJUVANT HORMONE TREATMENT | |
| 9) | LOWER RISK | ((FOXA1 is ELEVATED and PR is POSITIVE) or PR is NEGATIVE) and (SIAH2 is LOW and (PR is NEGATIVE or HER2 is POSITIVE)) | LOWER DCIS RISK TREATMENT | LOWER RISK TREATMENT | 9 |
| | ELEVATED RISK | (FOXA1 is LOW and PR is POSITIVE) OR (SIAH2 is ELEVATED AND (PR is NEGATIVE or HER2 is POSITIVE)) | BCS + RT | BCS + RT + (ADJUVANT HORMONE TREATMENT if PR is POS) or (ADJUVANT TARGETED HER2 TREATMENT if HER2 is POS) | |
| 10) | LOW RISK | ((FOXA1 is ELEVATED and PR is POSITIVE) or PR is NEGATIVE) and (SIAH2 is LOW and (PR is NEGATIVE or HER2 is POSITIVE or AGE is ELEVATED)) | LOWER DCIS RISK TREATMENT | LOWER RISK TREATMENT | 4, 5, 8, 9 |
| | ELEVATED RISK | (SIAH2 is ELEVATED and (PR is NEGATIVE or HER2 is POSITIVE or AGE is ELEVATED) ) or (FOXA1 is LOW and PR is POSITIVE) | BCS + RT | | |

TABLE 14-continued

(DCIS RISK)

| | TABLE 14 LEGEND: | "<" means less than<br>"<=" means less than or equal to<br>">" means greater than<br>">=" means greater than or equal to |
|---|---|---|
| FOXA1 is LOW | FOXA1 ASSESSED BY IMMUNOSCORE (INTENSITY TIMES PERCENTAGE) | <150 IMMUNOSCORE |
| FOXA1 is ELEVATED | FOXA1 ASSESSED BY IMMUNOSCORE (INTENSITY TIMES PERCENTAGE) | >=150 IMMUNOSCORE |
| PR is NEGATIVE | PR ASSESSED BY PERCENTAGE | <15% |
| PR is POSITIVE | PR ASSESSED BY PERCENTAGE | >=15% |
| HER2 is NEGATIVE | HER2 ASSESSED BY IHC AS (EITHER 1+ OR 2+) OR BY FISH AS NEGATIVE OR BY SISH AS NEGATIVE; HOWEVER IF ANY OF THESE ARE POSITIVE THEN THE RESULT IS POSITIVE | HER2 IHC (1+ OR 2+), OR FISH NEG, OR SISH NEG; HOWEVER IF ANY OF THESE ARE POSITIVE THEN THE RESULT IS POSITIVE |
| HER2 is POSITIVE | HER2 ASSESSED BY IHC AS (EITHER 3+) OR BY FISH AS POSITIVE OR BY SISH AS POSITIVE HOWEVER IF ANY OF THESE ARE POSITIVE THEN THE RESULT IS POSITIVE | HER2 IHC (3+), OR FISH POS, OR SISH POS; WHERE IF ANY OF THESE ARE POSITIVE THEN THE RESULT IS POSITIVE |
| AGE is LOW | AGE assessed by patient age at diagnosis of initial DCIS | AGE <50 |
| AGE is ELEVATED | AGE assessed by patient age at diagnosis of initial DCIS | AGE >=50 |
| SIAH2 is LOW | SIAH2 ASSESSED BY IHC AS PERCENTAGE | <20 |
| SIAH2 is ELEVATED | SIAH2 ASSESSED BY IHC AS PERCENTAGE | >=30 |
| PALPABLE | The patient presented following the finding of a palpable mass in the breast or a physical exam found a palpable mass in the breast | IS PALPABLE |

TABLE 14-continued (DCIS RISK)

| NOT PALPABLE | The patient was not found to have a palpable mass in the breast | NOT PALPABLE |

LOWER DCIS RISK TREATMENT: Breast conserving surgery (BCS) ONLY, without adjuvant therapy or BCS with adjuvant hormone treatment, in combination with either standard or more frequent than standard surveillance may be selected for patients with LOWER DCIS RISK. However, for patients assessed as having LOWER DCIS RISK of recurrence, the treatment also needs to reflect the risk potential for subsequent invasive breast cancer. Additionally, the patient risk tolerance may be considered in selecting the nature of the treatment. For example, if DCIS recurrence is evaluated as LOWER RISK, but the risk of INVASIVE breast cancer after initial diagnosis of DCIS is ELEVATED RISK, then breast conserving surgery with (adjuvant radiation therapy, adjuvant targeted HER2 treatment, or adjuvant hormone treatment), or mastectomy would be selected. For example, if DCIS recurrence is evaluated as LOWER RISK, but the risk of INVASIVE breast cancer after initial diagnosis of DCIS is UNKNOWN, then breast conserving surgery with (adjuvant radiation therapy, adjuvant targeted HER2 treatment, or adjuvant hormone treatment), or mastectomy would be selected. In the case that the risk of recurrence of DCIS is ELEVATED RISK, then Breast Conserving Surgery with Radiation therapy would be recommended. The patient risk tolerance may be considered in the selection of the therapy for patients with ELEVATED DCIS RISK. Adjuvant treatment consisting of adjuvant hormone treatment or adjuvant targeted treatment for HER2 may be selected as the treatment to augment breast conserving surgery alone.

In some embodiments, the marker signatures disclosed and described herein can be used to comprehensively determine a total recurrence or progression risk and/or the likelihood that a subject will respond or will not respond to radiation therapy and therefore, determine a more appropriate treatment. The (a) markers listed in Table 13 are used to assess risk of an invasive breast cancer and (b) the markers listed in Table 14 are used to assess risk of a DCIS event. In combination, the total risk, which includes risk of an invasive event and risk of a DCIS event, may be determined and used to recommend a more appropriate treatment. For example, if a patient is found to be of low risk for an invasive event according to Table 13 but at a high risk for a DCIS event according to Table 14, the patient would be at a high total risk of recurrence. As disclosed and described herein, the various methods and compositions can allow one to determine the likelihood of (a) a recurrent breast event, (b) progression to invasive or metastatic cancer, or (c) whether or not a subject/patient with DCIS now will experience no further DCIS/invasive breast cancer, experience DCIS and/or experience invasive breast cancer and to thus, treat a patient diagnosed with DCIS in a more appropriate manner. The same can be applied for Table 15, as a combined option. Then, one can further determine, based on for example, the k-ras pathway levels and/or HER2 and SIAH2 state of the sample, if the subject will be responsive to radiation therapy, and thereby determine if the subject should receive radiation therapy or a non-radiation therapy such as a HER2 antibody, such as trastuzumab. Thus, in some embodiments, any option for determining risk level can be combined with a further option (where appropriate) for determining k-ras pathway levels and/or HER2 and SIAH2 state of the sample to determine if the subject will be responsive to radiation therapy, and thereby determine if the subject should receive radiation therapy or a non-radiation therapy such as a HER2 antibody, such as trastuzumab (as detailed herein).

In some embodiments, the marker signatures disclosed and described herein can be used to comprehensively treat a patient in a manner that appropriately reduces the risk of total recurrence or progression, including an invasive event and/or a DCIS event. For example, (a) the marker signatures in Table 13 can be used to identify a treatment that reduces the risk of an invasive event and (b) the marker signatures in Table 14 can be used to identify a treatment that reduces the risk of an DCIS event and/or identify treatment to reduce total risk according to Table 13 and Table 14. The same can be applied for Table 15, as a combined option. The subject at elevated risk of an invasive event can then be treated with either a radiation or non-radiation therapy, as outlined herein.

The following is a non-exhaustive list of examples of treatment alternatives for patients based on their individual risk profiles as set forth in Tables 13-15.

Example 1

A DCIS sample from a subject having DCIS is analyzing for SIAH2 and HER2, and for at least one of PR, FOXA1, or (in the alternative) analyzed for FOXA1 and PR. The results are compared with the matrix in Tables 9 and/or 11 to determine if the subject has an elevated risk of invasive breast cancer, DCIS recurrence, or neither. If the subject has an elevated risk of invasive breast cancer, one reviews the SIAH2 and HER2 levels. A subject that is HER2+ and SIAH2+ will not receive radiation therapy and will instead receive trastuzumab.

Example 2

A DCIS sample from a subject is analyzed for a level of at least PR, HER2 and SIAH2, or (in the alternative) analyzing the sample for at least FOXA1. A prognosis is provided based upon at least PR, HER2 and SIAH2 or based upon at least PR and FOXA1. Depending upon the nature of the results, this indicates that the subject that provided the sample is at a high or elevated risk of invasive breast cancer (see, e.g., Tables 9 and/or 11). If the subject has an elevated risk of invasive breast cancer, one reviews the SIAH2 and HER2 levels. A subject that is HER2+ and SIAH2+ will not receive radiation therapy and will instead receive an anti-HER2 antibody.

Example 3

A DCIS sample from a subject is analyzed for a level of at least SIAH2 and FOXA1. A prognosis is provided with the subject having an elevated risk of an invasive breast cancer based upon the level of at least SIAH2 and FOXA1. If the subject has an elevated risk of invasive breast cancer, one reviews the SIAH2 and HER2 levels. A subject that is HER2+ and SIAH2+ will not receive radiation therapy and will instead receive an anti-HER2 antibody.

Example 4

A DCIS sample from a subject is analyzed for: a) PR, HER2, and SIAH2, or (in the alternative) b) PR and FOXA1. A prognosis is provided for the subject as having an elevated risk of an invasive breast cancer event when at least one of: a) PR−, HER2−, and SIAH2−, b) PR+, FOXA1+, or c) PR+, FOXA1−, and Ki67+. If the subject has an elevated risk of invasive breast cancer, one reviews the SIAH2 and HER2 levels. A subject that is HER2+ and SIAH2+ will not receive radiation therapy and will instead receive an anti-HER2 antibody.

Example 5

A DCIS sample is analyzed for at least one of: a) SIAH2 and FOXA1, b) SIAH2 and at least one of i) PR and ii) HER2, c) SIAH2 and post-menopausal status; or (in the alternative) d) PR and FOXA1. A prognosis is provided that the subject has an elevated risk of a DCIS event when at least one of: a) i) SIAH2+ and FOXA1+, b) SIAH2+ and HER2+ or PR−; SIAH2+ and post-menopausal; or PR+ and FOXA1−, is present in the DCIS sample. If the subject has an elevated risk of invasive breast cancer, one reviews the SIAH2 and HER2 levels. A subject that is HER2+ and SIAH2+ will not receive radiation therapy and will instead receive an anti-HER2 antibody.

Example 6

A DCIS sample is analyzed for at least one of: a) PR−, HER2−, and SIAH2−, b) PR+, FOXA1+, or c) PR+, FOXA1−, and Ki67+. When the analysis indicates a high risk of invasive breast cancer (see, Tables 9 and/or 11) the subject is administered a therapy that is more aggressive than standard of care for DCIS. If the subject has an elevated risk of invasive breast cancer, one reviews SIAH2 and HER2 levels. A subject that is HER2+ and SIAH2+ will not receive radiation therapy and will instead receive an anti-HER2 antibody.

Example 7

A DCIS sample is analyzed for at least one of: a) SIAH2+ and FOXA1+, b) SIAH2+ and HER2+ or PR−, c) SIAH2+ and post-menopausal status, or (in the alternative) d) PR+ and FOXA1−. When the analysis indicates a high likelihood of an invasive breast cancer, one administers to the subject a more aggressive therapy than standard of care for a single DCIS event. If the subject has an elevated risk of invasive breast cancer, one reviews the SIAH2 and HER2 levels. A subject that is HER2+ and SIAH2+ will not receive radiation therapy and will instead receive an anti-HER2 antibody.

Example 8

A subject provides a sample that is analyzed for at least one of the combinations as outlined in any one of Tables 13-15 to provide a risk level for the subject. A corresponding treatment is then administered to the subject, as outlined in the appropriate row in Tables 13-15, based on the indicated risk level for the subject. If the subject has an elevated risk of invasive breast cancer, one reviews the SIAH2 and HER2 levels. A subject that is HER2+ and SIAH2+ will not receive radiation therapy and will instead receive an anti-HER2 antibody.

Example 9

Figure 2:
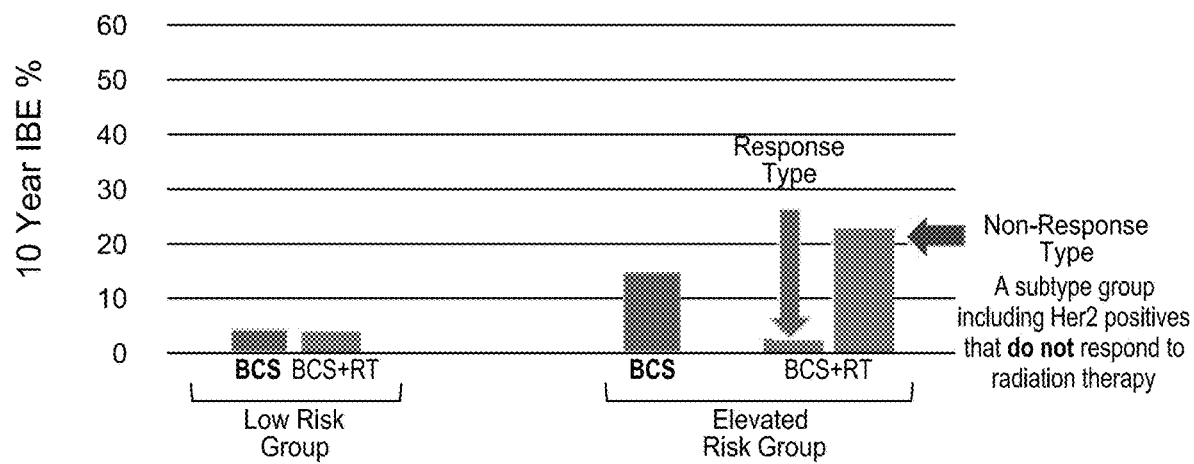
FIG. 2 is a set of graphs depicting that there is a subset of people who do not respond to radiation therapy, who are HER2+ and SIAH2+.

As shown in FIG. 1, the greater majority of subjects that have DCIS, that are at an elevated risk of invasive breast cancer receive a significant benefit from radiation therapy. However, as shown in FIG. 2, there is a non-responsive subgrouping of these people who do not respond to radiation therapy. These individuals are HER2+ and SIAH+.

What is claimed is:

1. A method of identifying a subject for treating with a breast cancer therapy, the method comprising:
    providing a DCIS sample from a subject with a primary DCIS, wherein the subject has an elevated risk of subsequent ipsilateral breast cancer recurrence;
    analyzing the DCIS sample from the subject by measuring expression levels of HER2 and SIAH2;
    identifying and selecting the subject for breast cancer therapy based on positive expression levels of both HER2 and SIAH2; and
    administering to the selected subject:
        (i) surgical removal of the primary DCIS; and
        (ii) one or more of aggressive radiation therapy or a non-radiation therapy, to treat the subject for breast cancer, thereby reducing an elevated risk of subsequent ipsilateral breast cancer recurrence, wherein the DCIS sample is at least Ki67 positive.

2. The method of claim 1, wherein the non-radiation therapy comprises an anti-HER2 antibody.

3. The method of claim 2, wherein the antibody is Trastuzumab.

4. The method of claim 1, wherein the DCIS sample is PR positive and has a very high expression level of FOXA1.

5. The method of claim 1, wherein analyzing the DCIS sample further comprises measuring expression levels of p16 and COX2.

6. The method of claim 5, wherein analysis of each marker is carried out in parallel with each other.

7. The method of claim 5, wherein analysis of each marker is carried out at overlapping times.

8. The method of claim 1, wherein the non-radiation therapy comprises chemotherapy.

9. The method of claim 1, wherein the DCIS sample is at least: i) PR positive and FOXA1 positive; or ii) PR positive, FOXA1 negative, and Ki67 positive.

10. The method of claim 1, wherein the subject with the primary DCIS is identified to have the elevated risk of subsequent ipsilateral breast cancer recurrence based on an analysis of one or more of the following markers in the DCIS sample from the subject: PR, FOXA1, COX2, and p16.

11. The method of claim 10, comprising further analyzing the DCIS sample for one or more of the markers.

12. The method of claim 1, comprising analyzing the DCIS sample for grade, necrosis, size, and/or margin status.

13. The method of claim 1, wherein the administered breast cancer therapy is more aggressive than a standard of care therapy that reduces the risk of subsequent ipsilateral breast cancer recurrence by approximately half when administered without measuring expression levels of both HER2 and SIAH2.

* * * * *